US009056871B2

(12) United States Patent
Ikeda et al.

(10) Patent No.: US 9,056,871 B2
(45) Date of Patent: Jun. 16, 2015

(54) ADDUCT COMPOUND, METHODS FOR PURIFICATION AND PREPARATION OF FUSED POLYCYCLIC AROMATIC COMPOUND, SOLUTION FOR FORMATION OF ORGANIC SEMICONDUCTOR FILM, AND NOVEL ALPHA-DIKETONE COMPOUND

(75) Inventors: Yoshinori Ikeda, Hino (JP); Takashi Shiro, Hino (JP); Kazuo Takimiya, Higashihiroshima (JP)

(73) Assignee: Teijin Limited, Osaka (JP)

( * ) Notice: Subject to any disclaimer, the term of this patent is extended or adjusted under 35 U.S.C. 154(b) by 480 days.

(21) Appl. No.: 13/392,996

(22) PCT Filed: Aug. 24, 2010

(86) PCT No.: PCT/JP2010/064272
§ 371 (c)(1),
(2), (4) Date: May 8, 2012

(87) PCT Pub. No.: WO2011/024804
PCT Pub. Date: Mar. 3, 2011

(65) Prior Publication Data
US 2012/0211731 A1    Aug. 23, 2012

(30) Foreign Application Priority Data

Aug. 28, 2009 (JP) ................. 2009-198753
Jan. 22, 2010 (JP) ................. 2010-012166
Jan. 22, 2010 (JP) ................. 2010-012242
Jan. 22, 2010 (JP) ................. 2010-012269
Feb. 12, 2010 (JP) ................. 2010-029163
Mar. 2, 2010 (JP) ................. 2010-045814

(51) Int. Cl.
C07D 495/04     (2006.01)
C07D 495/22     (2006.01)
C07D 495/08     (2006.01)
C07D 495/18     (2006.01)
C07D 513/18     (2006.01)
H01L 51/00      (2006.01)
H01L 51/05      (2006.01)

(52) U.S. Cl.
CPC ............ *C07D 495/04* (2013.01); *C07D 495/08* (2013.01); *C07D 495/18* (2013.01); *C07D 495/22* (2013.01); *C07D 513/18* (2013.01); *H01L 51/0053* (2013.01); *H01L 51/0074* (2013.01); *H01L 51/0545* (2013.01)

(58) Field of Classification Search
None
See application file for complete search history.

(56) References Cited

U.S. PATENT DOCUMENTS

| 2006/0081880 | A1 | 4/2006  | Miyazaki et al. |
| 2007/0085072 | A1 | 4/2007  | Masumoto et al. |
| 2008/0171403 | A1 | 7/2008  | Masumoto et al. |
| 2008/0249309 | A1 | 10/2008 | Facchetti et al. |
| 2009/0001357 | A1 | 1/2009  | Takimiya et al. |
| 2009/0043113 | A1 | 2/2009  | Park et al. |
| 2010/0065826 | A1 | 3/2010  | Takimiya et al. |

FOREIGN PATENT DOCUMENTS

| JP | 2004-266157 A | 9/2004 |
| JP | 2006-032914 A | 2/2006 |
| JP | 2006-089413 A | 4/2006 |
| JP | 2006-248982 A | 9/2006 |
| JP | 2007-273938 A | 10/2007 |
| JP | 2008-10541 A  | 1/2008 |
| JP | 2008-290963 A | 12/2008 |
| JP | 2009-081408 A | 4/2009 |
| JP | 2009-152355 A | 7/2009 |
| WO | 2006/077888 A1 | 7/2006 |
| WO | 2008/050726 A1 | 5/2008 |
| WO | 2008/091670 A2 | 7/2008 |
| WO | 2009/009790 A1 | 1/2009 |

OTHER PUBLICATIONS

Mondal et al.; Photodecarbonylation of α-Diketones: A Mechanistic Study of Reactions Leading to Acenes; Journal of Physical Chemistry B, 2008, vol. 12, No. 1, pp. 11-15.
Iwata, M. et al.; Pyridoxal model compounds. II. The Diels-Alder reaction of 9-substituted 2-methoxyanthracenes, Bulletin of the Chemical Society of Japan, 1976, vol. 49, No. 4, pp. 1163-1164.
International Search Report of PCT/JP2010/064272 dated Sep. 21, 2010.
Hidemitsu Uno, et al., "Photo precursor for pentacene", Tetrahedron Letters, 2005, pp. 1981-1983, vol. 46.
Yu-Man Wang, et al., "Synthesis, characterization, and reactions of 6,13-disubstituted 2,3,9,10-tetrakis(trimethylsilyl)pentacene derivatives", Tetrahedron, 2007, pp. 8586-8597, vol. 63.
Tatsuya Yamamoto, et al., "Facile Synthesis of Highly π-Extended Heteroarenes Dinaphtho[2,3-b:2',3'-f]chalcogenopheno[3,2-b]chalcogenophenes, and Their Application to Field-Effect Transistors", J. Am. Chem. Soc., 2007, pp. 2224-2225, vol. 129.

(Continued)

*Primary Examiner* — Sun Jae Yoo
(74) *Attorney, Agent, or Firm* — Sughrue Mion, PLLC

(57) ABSTRACT

Provided are a novel adduct compound and a novel α-diketone compound, from which organic semiconductor layers consisting of a fused polycyclic aromatic compound can be formed by a solution method, said solution method being generally easier than a deposition method. Also provided are a method for the purification of the adduct compound, and a solution for the formation of organic semiconductor film, which contains the adduct compound. The adduct compound has a structure wherein a compound having a double bond is added in an eliminable state to a fused polycyclic aromatic compound of general formula (I): $Ar_1 Ar_2 Ar_3$ (I), while the α-diketone compound has a structure wherein a compound having a double bond is added in an eliminable state to a fused polycyclic aromatic compound. The fused polycyclic aromatic compound is dinaphthothienothiophene or the like, while the compound having a double bond is hexachlorocyclopentadiene or the like. In general formula (I), $Ar_1$, $Ar_2$ and $Ar_3$ are each as defined in the description.

30 Claims, 16 Drawing Sheets

(56) References Cited

OTHER PUBLICATIONS

A. A. Danish, et al., "Dienophilic Reactions of Aromatic Double Bonds in the Synthesis of β-Substituted Naphthalenes", Research Department of Hyman Laboratories, Inc., Feb. 23, 1954, J. Am. Chem. Soc., pp. 6144-6150, vol. 76 (23).

Claire Lacourcelle, et al., "Tandem Diels-Alder-Diels-Alder Reaction Displaying High Stereoselectivity: Reaction of Hexachlorocyclopentadiene with Naphthalene", Acta Chemica Scandinavica, 1993, pp. 92-94, vol. 47.

Iwata, M. et al.; Pyridoxal model compounds. II. The Diels-Alder reaction of 9-substituted 2- methoxyanthracenes, Bulletin of the Chemical Society of Japan, 1976, vol. 49, No. 4, pp. 1163-1164.

Iwata, M. et al.; Pyridoxal model compounds. I. Regioselective formylation of methoxy-substituted aromatic compounds, Bulletin of the Chemical Society of Japan, 1974, vol. 47, No. 7, pp. 1687-1692.

Fig. 17
(a) 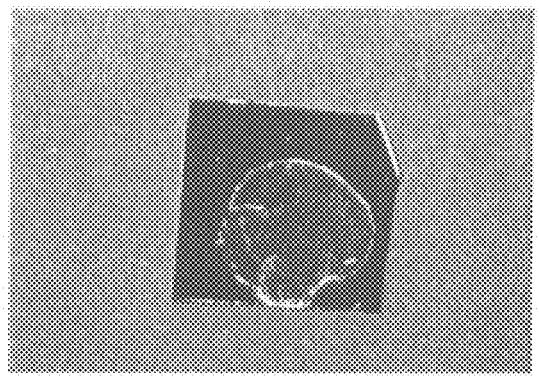
(b) 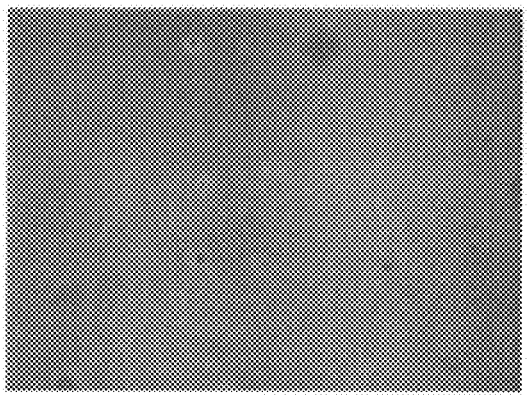

Fig.18
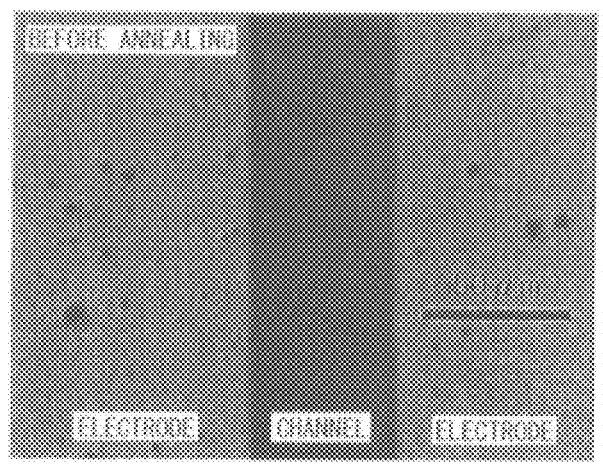
(a)
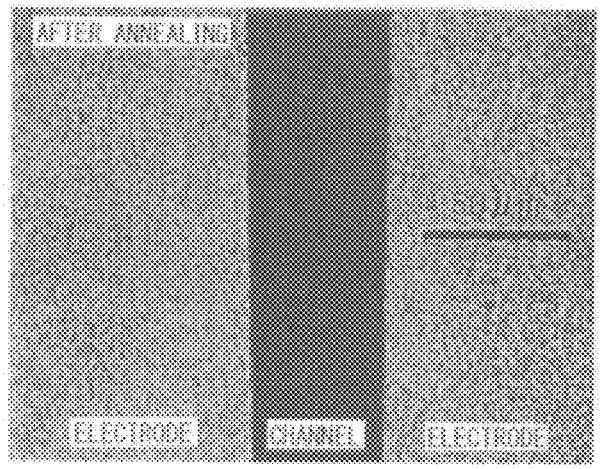
(b)

US 9,056,871 B2

ADDUCT COMPOUND, METHODS FOR PURIFICATION AND PREPARATION OF FUSED POLYCYCLIC AROMATIC COMPOUND, SOLUTION FOR FORMATION OF ORGANIC SEMICONDUCTOR FILM, AND NOVEL ALPHA-DIKETONE COMPOUND

CROSS REFERENCE TO RELATED APPLICATIONS

This application is a National Stage of International Application No. PCT/JP2010/064272 filed Aug. 24, 2010, the contents of which are incorporated herein by reference in their entirety.

TECHNICAL FIELD

The first present invention relates to a novel adduct compound, an organic semiconductor device, and their production methods. The first present invention also relates to an intermediate for such a novel adduct compound, a solution containing the novel adduct compound, and a method for using the same. The second present invention relates to methods for purification and production of a fused polycyclic aromatic compound, and in particular methods for purification and production of a fused polycyclic aromatic compound suitably used as an organic semiconductor compound. The third present invention relates to a novel organic semiconductor film-forming solution, and a method for using the solution to form an organic semiconductor film. The third present invention also relates to an organic semiconductor device obtained by using such an organic semiconductor film-forming solution. The fourth present invention relates to a novel α-diketone compound, an organic semiconductor device and their production methods. The fourth present invention also relates to an intermediate for such a novel α-diketone compound, a solution containing the novel α-diketone compound, and a method for using the same.

BACKGROUND ART

Various studies regarding an organic semiconductor compound have been made in order to use it to form an organic semiconductor layer for organic thin-film transistors (TFT), organic carrier transport layers, organic light-emitting devices and the like. In particular, a thin-film transistor having an organic semiconductor layer formed of an organic semiconductor compound is expected to work as a low-cost and lightweight device, and thereby substitute for the current silicon-based transistor. Also, applying an organic semiconductor layer to a smart tag, a lightweight display and the like, and utilizing the advantages peculiar to an organic material, such as lightweight and flexible properties is being persuaded.

Accordingly, many studies have been made on the organic semiconductor compound for forming the organic semiconductor layer (Patent Documents 1 to 4 and Non-Patent Documents 1 and 4). Among these organic semiconductor compounds, fused polycyclic aromatic compounds are noted as being preferred in terms of stability of the material, mobility of the carrier, and the like.

Incidentally, a reaction referred to as a Diels-Alder reaction is known in the field of organic synthesis. In this reaction, a compound having a double bond or a triple bond is added to the 1-position and 4-position of a compound having conjugated double bonds to produce a 6-membered cyclic compound. Adding hexachlorocyclopentadiene to naphthalene by using the Diels-Alder reaction has also been proposed (Non-Patent Documents 2 and 3).

Furthermore, it is known to use a precursor which is a soluble precursor of pentacene as an example of the organic semiconductor compound and which can be decomposed by light irradiation to generate pentacene (Non-Patent Document 4).

RELATED ART

Patent Documents

Patent Document 1: Japanese Unexamined Patent Publication No. 2006-89413
Patent Document 2: Japanese Unexamined Patent Publication No. 2008-290963
Patent Document 3: International Patent Publication No. WO2006/077888
Patent Document 4: International Patent Publication No. 2008/050726

Non-Patent Documents

Non-Patent Document 1: "Facile Synthesis of Highly π-Extended Heteroarenes, Dinaphtho[2,3-b:2',3'-f]chalcogenopheno[3,2-b]chalcogenophenes, and Their Application to Field-Effect Transistors", Tatsuya Yamamoto, and Kazuo Takimiya, J. Am. Chem. Soc., 2007, 129 (8), pp. 2224-2225
Non-Patent Document 2: "Dienophilic Reactions of Aromatic Double Bonds in the Synthesis of β-Substituted Naphthalenes", A. A. Danish, M. Silverman, Y. A. Tajima, J. Am. Chem. Soc., 1954, 76 (23), pp. 6144-6150
Non-Patent Document 3: "Tandem Diels-Alder-Diels-Alder Reaction Displaying High Stereoselectivity: Reaction of Hexachlorocyclopentadiene with Naphthalene", Lacourcelle, Claire; Poite, Jean Claude; Baldy, Andre; Jaud, Joel; Negrel, Jean Claude; Chanon, Michel, Acta Chemica Scandinavica 47, 0092-0094
Non-Patent Document 4: "Photo Precursor for Pentacene", Hidemitsu Uno, et al., Elsevier, Tetrahedron Letters 46 (2005) 1981-1983

SUMMARY OF THE INVENTION

Problems to be Solved by the Invention (First Present Invention)

Regarding the formation of an organic semiconductor layer, using a solution method (e.g., casting, spin coating, printing) to coat an organic semiconductor compound-containing solution onto a substrate and then removing the solvent, and a vapor deposition method of vapor depositing an organic semiconductor compound on a substrate is known. The solution method is generally acknowledged as being preferred in terms of production cost, production speed and the like.

However, the fused polycyclic aromatic compound, which is known to be preferred as an organic semiconductor compound, is nonpolar and highly crystalline, and therefore can be hardly dissolved in a solution. For this reason, in the formation of an organic semiconductor layer from a fused polycyclic aromatic compound, and particularly in the formation of an organic semiconductor layer from a low-molecular fused polycyclic aromatic compound, a vapor deposition method is generally employed.

Accordingly, the first present invention provides a novel adduct compound which makes it possible to form, by a solution method, an organic semiconductor layer formed of a fused polycyclic aromatic compound, and a solution containing the novel adduct compound. The present invention also provides an organic semiconductor film (organic semiconductor layer) and an organic semiconductor device, which are obtained by using such a novel adduct compound. The present invention further provides a synthesis method of the novel adduct compound.

(Second Present Invention)

As described above, a fused polycyclic aromatic compound is preferred as an organic semiconductor compound for the formation of an organic semiconductor. Very high purity is required for the fused polycyclic aromatic compound used for such application.

Many methods have been proposed to produce a fused polycyclic aromatic compound, and as a matter of course, a substance working as an impurity in the final fused polycyclic aromatic compound is used in the synthesis reaction. For removing such an impurity, solvent washing, vacuum sublimation purification or the like is performed. However, the fused polycyclic aromatic compound has high crystallinity, and sometimes captures an impurity in its crystal structure. Therefore, the impurity captured in the crystal may not be sufficiently removed by the conventional purification method, such as solvent washing.

Accordingly, the second present invention provides methods for purification and production of a fused polycyclic aromatic compound, and in particular methods for purification and production of a fused polycyclic aromatic compound suitably used as an organic semiconductor compound, and thereby overcome the above-described problem.

(Third Present Invention)

In the formation of an organic semiconductor layer, using a solution method (e.g., casting, spin coating, printing) of coating an organic semiconductor compound-containing solution on a substrate and then removing the solvent, and a vapor deposition method of vapor depositing an organic semiconductor compound on a substrate is known. The solution method is generally acknowledged as being preferred in terms of production cost, production speed and the like.

However, the fused polycyclic aromatic compound, which is preferable as an organic semiconductor compound, is nonpolar and highly crystalline, and therefore does not readily dissolve in a solution. For this reason, in the formation of an organic semiconductor layer from a fused polycyclic aromatic compound, and in particular in the formation of an organic semiconductor layer from a low-molecular fused polycyclic aromatic compound, a vapor deposition method is generally employed.

Accordingly, the third present invention provides a novel organic semiconductor film-forming solution, which makes it possible to stably form, by a solution method, an organic semiconductor layer (organic semiconductor film) formed of a fused polycyclic aromatic compound, and a method of using this organic semiconductor film-forming solution. The present invention also provides an organic semiconductor device obtained using such an organic semiconductor film-forming solution.

(Fourth Present Invention)

In the formation of an organic semiconductor layer, using a solution method (e.g., casting, spin coating, printing) of coating an organic semiconductor compound-containing solution on a substrate and then removing the solvent, and a vapor deposition method of vapor depositing an organic semiconductor compound on a substrate is known. The solution method is generally acknowledged as being preferred in terms of production cost, production speed and the like.

However, the fused polycyclic aromatic compound which is preferable as an organic semiconductor compound is nonpolar and highly crystalline, and therefore does not readily dissolve in a solution. For this reason, in the formation of an organic semiconductor layer from a fused polycyclic aromatic compound, and particularly in the formation of an organic semiconductor layer from a low-molecular fused polycyclic aromatic compound, a vapor deposition method is generally employed.

Accordingly, the fourth present invention provides a novel α-diketone compound which makes it possible to form, by a solution method, an organic semiconductor layer formed of a fused polycyclic aromatic compound, and a solution containing the novel α-diketone compound. The present invention also provides an organic semiconductor film (organic semiconductor layer) and an organic semiconductor device, which are obtained by using such a novel α-diketone compound. The present invention further provides a synthesis method of the novel α-diketone compound.

Means to Solve the Problems (First Present Invention)

The present inventors have found that an adduct compound having a structure, wherein a specific compound is added to a compound such as dinaphthothienothiophene, can solve the above-described problems, and thereby achieved the first present invention.

The adduct compound of the present invention has a structure wherein a double bond-containing compound (II), such as hexachlorocyclopentadiene, is added in an eliminatable state to a fused polycyclic aromatic compound of the following formula (I), such as dinaphthothienothiophene, through the double bond:

$$Ar_1Ar_2Ar_3 \qquad (I)$$

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms).

The adduct compound-containing solution of the present invention is a solution comprising the adduct compound of the present invention dissolved in an organic solvent.

The method of the present invention for producing an organic semiconductor film comprises coating the adduct compound-containing solution of the present invention on a substrate to form a film, and eliminating the double bond-containing compound (II) from the adduct compound and removing the double bond-containing compound (II) by depressurizing and/or heating the film to obtain an organic semiconductor film formed of the fused polycyclic aromatic compound of formula (I).

The method of the present invention for producing an organic semiconductor device comprises producing an organic semiconductor film by the method for producing an organic semiconductor film of the present invention.

The organic semiconductor device of the present invention has an organic semiconductor film, the organic semiconductor film is formed of a fused polycyclic aromatic compound of formula (I) having a structure wherein the double bond-containing compound (II) is eliminated from the adduct compound of the present invention, and the organic semiconductor film contains the adduct compound of the present invention. Also, the organic semiconductor device has an organic semiconductor film, and the organic semiconductor film has a crystal with a long axis diameter of more than 5 μm of the fused polycyclic aromatic compound of formula (I).

Other novel adduct compound (intermediate adduct compounds) of the present invention is a compound which can be used as an intermediate for synthesizing the adduct compound of the present invention and to which a double bond-containing compound (II) is added.

The method of the present invention for synthesizing the adduct compound of the present invention comprises mixing the fused polycyclic aromatic compound of formula (I) with the double bond-containing compound (II). Also, another method of the present invention for synthesizing the adduct compound of the present invention comprises reacting two molecules of the intermediate adduct compound of the present invention.

Incidentally, the "adduct compound" of the present invention means any compound having a structure wherein a double bond-containing compound (II) is added in an eliminatable state to the fused polycyclic aromatic compound of formula (I) through the double bond, and is not limited by its specific synthesis method. Also, the adduct compound of the present invention may be not only an adduct compound having a structure wherein one molecule of the double bond-containing compound (II) is added to the fused polycyclic aromatic compound of formula (I), but also an adduct compound having a structure wherein two molecules, three molecules, four molecules or a greater number of molecules of the double bond-containing compound (II) are added to the fused polycyclic aromatic compound of formula (I).

The term "aromatic ring" as used in the present invention means a conjugated ring similar to a benzene ring, and includes, for example, a heteroaromatic ring such as furan ring, thiophene ring, pyrrole ring and imidazole ring, as well as a benzene ring. Also, the term "stereoisomer" as used in the present invention means anisotropy caused by the difference in the steric configuration of atoms or atomic groups in compounds having the same structural formula, and includes an optical isomer, a geometric isomer, a rotational isomer and the like.

(Second Present Invention)

The present inventors have found that a fused polycyclic aromatic compound can be purified and produced by using an addition-elimination reaction, and thereby achieved the second present invention.

The method of the present invention for purifying a fused polycyclic aromatic compound of the following formula (I) comprises the following steps (a) to (d):

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms);

(a) providing a crude product of the fused polycyclic aromatic compound of formula (I), (b) providing a double bond-containing compound (II) capable of being added in an eliminatable state to the fused polycyclic aromatic compound of formula (I), (c) mixing the fused polycyclic aromatic compound of formula (I) with the double bond-containing compound (II) to obtain a mixed solution containing an adduct compound of these compounds which is at least partially dissolved in the mixed solution, and (d) separating and obtaining the purified fused polycyclic aromatic compound of formula (I) from the mixed solution.

The method of the present invention for producing a fused polycyclic aromatic compound comprises purifying a crude product of the fused polycyclic aromatic compound by the method of the present invention. Also, another method of the present invention for producing the fused polycyclic aromatic compound of the present invention comprises obtaining the fused polycyclic aromatic compound from an adduct compound of the fused polycyclic aromatic compound.

Incidentally, the term "adduct compound" as used herein means any compound having a structure wherein a double bond-containing compound (II) is added in an eliminatable state to the fused polycyclic aromatic compound of formula (I) through the double bond, and is not limited by its specific synthesis method. Also, the adduct compound may be not only an adduct compound having a structure wherein one molecule of the double bond-containing compound (II) is added to the fused polycyclic aromatic compound of formula (I), but also an adduct compound having a structure wherein two molecules, three molecules, four molecules or a greater number of molecules of the double bond-containing compound (II) are added to the fused polycyclic aromatic compound of formula (I).

The term "aromatic ring" as used in the present invention means a conjugated ring similarly to a benzene ring, and includes, for example, a heteroaromatic ring such as furan ring, thiophene ring, pyrrole ring and imidazole ring, as well as a benzene ring. Also, the term "stereoisomer" as used in the present invention means anisotropy caused by the difference in the steric configuration of atoms or atomic groups in compounds having the same structural formula, and includes an optical isomer, a geometric isomer, a rotational isomer and the like.

(Third Present Invention)

The present inventors have found that the above-described problems can be solved by an organic semiconductor film-forming solution containing an adduct compound having a structure wherein a specific compound is added to a compound such as dinaphthothienothiophene, and thereby achieved the third present invention.

The organic semiconductor film-forming solution of the present invention contains an organic solvent, a first adduct compound dissolved in the organic solvent, and a crystallization inhibitor dissolved in the organic solvent and capable of inhibiting crystallization of the first adduct compound.

The first adduct compound has a structure wherein a double bond-containing first compound (II') is added in an eliminatable state to a fused polycyclic aromatic compound of the following formula (I) through the double bond:

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms).

The crystallization inhibitor is at least one compound selected from the group consisting of the following (a) to (c):

(a) a second adduct compound having a structure wherein a second double bond-containing compound (II") is added in an eliminatable state to the fused polycyclic aromatic compound of formula (I) through the double bond, (b) the first double bond-containing compound (II'), which is capable of being added in an eliminatable state to the fused polycyclic aromatic compound of formula (I) through the double bond, and (c) the second double bond-containing compound (II"), which is capable of being added in an eliminatable state to the fused polycyclic aromatic compound of formula (I) through the double bond.

The method of the present invention for producing an organic semiconductor film comprises coating the solution of the present invention on a substrate to form a film, and eliminating the double bond-containing first compound (II') from the first adduct compound and removing the double bond-containing compound (II) by depressurizing and/or heating the film to obtain an organic semiconductor film formed of the fused polycyclic aromatic compound of formula (I). The method of the present invention for producing an organic semiconductor device comprises producing an organic semiconductor film by the method of the present invention for producing an organic semiconductor film.

The organic semiconductor device of the present invention has an organic semiconductor film, wherein the organic semiconductor film is formed of an organic semiconductor compound of the following formula (I), the organic semiconductor film contains a first adduct compound having a structure wherein a first double bond-containing compound (II') is added in an eliminatable state to a fused polycyclic aromatic compound of the following formula (I) through the double bond; and the organic semiconductor film contains a first adduct compound a first double bond-containing compound (II') is added in an eliminatable state to a fused polycyclic aromatic compound of the following formula (I) through the double bond, and at least one compound selected from the group consisting of the following (a) to (c):

(wherein $Ar_1$ to $Ar_3$ are as described below).

Incidentally, in the present invention, the first and second "adduct compounds" mean any compounds having structures wherein a first double bond-containing compound (II') and a second double bond-containing compounds (II"), respectively, are added in an eliminatable state to the fused polycyclic aromatic compound of formula (I) through the double bond, and are not limited in the specific synthesis method. Also, the adduct compounds may be not only adduct compounds having structures wherein one molecule of the first and/or second double bond-containing compounds (II') and/or (II") is added to the fused polycyclic aromatic compound of formula (I), but also adduct compounds having a structure wherein two molecules, three molecules, four molecules or a greater number of molecules of the first and/or second double bond-containing compound (II') and/or compound (II') are added to the fused polycyclic aromatic compound of formula (I).

The term "aromatic ring" as used in the present invention means a conjugated ring similar to a benzene ring, and includes, for example, a heteroaromatic ring such as furan ring, thiophene ring, pyrrole ring and imidazole ring, as well as a benzene ring. Also, the term "stereoisomer" as used in the present invention means anisotropy caused by the difference in the steric configuration of atoms or atomic groups in the compounds having the same structural formula, and includes an optical isomer, a geometric isomer, a rotational isomer and the like.

In the following, for the sake of simplicity, the "first adduct compound" and the "second adduct compound" are sometimes collectively referred to as an "adduct compound". Similarly, for the sake of simplicity, the "first double bond-containing compound (II')" and the "second double bond-containing compound (II")" are sometimes collectively referred to as a "double bond-containing compound (II)".

(Fourth Present Invention)

The present inventors have found that the above-described problems can be solved by an α-diketone compound having a specific structure, and thereby achieved the fourth present invention.

The α-diketone compound of the present invention has the following formula (I(a)-X):

(wherein each of $Ar_{1X}$ and $Ar_{3X}$ is independently selected from the group consisting of substituted or unsubstituted fused aromatic ring moieties each formed of 2 to 5 aromatic rings fused together, and at least one of the aromatic rings is substituted by a bicyclo α-diketone moiety of the following formula (X):

[Chem. 1]

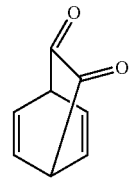

$Ar_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5 heteroaromatic rings fused together, $Ar_{1X}$ and $Ar_{2(a)}$ form a fused ring by sharing at least two carbon atoms, and $Ar_{2(a)}$ and $Ar_{3X}$ form a fused ring by sharing at least two carbon atoms}.

The α-diketone compound-containing solution of the present invention is a solution comprising the α-diketone compound of the present invention dissolved in an organic solvent.

The method of the present invention for producing an organic semiconductor film comprises coating the α-diketone compound-containing solution of the present invention on a substrate to produce a film, and irradiating the film with light to decompose the bicyclo α-diketone moiety of the α-diketone compound into a benzene ring moiety, thereby obtaining an organic semiconductor film formed of a fused polycyclic aromatic compound.

The method of the present invention for producing an organic semiconductor device comprises producing an organic semiconductor film by the method of the present invention for producing an organic semiconductor film.

The organic semiconductor device of the present invention has an organic semiconductor film, wherein the organic semiconductor film is formed of a fused polycyclic aromatic compound, and at the same time, the organic semiconductor film further contains the α-diketone compound of the present invention.

Other novel α-diketone compounds (intermediate α-diketone compounds) of the present invention are a compound which can be used as an intermediate for synthesizing the α-diketone compound of the present invention.

The method of the present invention for synthesizing the α-diketone compound of the present invention comprises hydrolyzing and oxidizing a vinylene carbonate-added fused polycyclic aromatic compound. Also, another method of the present invention for synthesizing the α-diketone compound of the present invention comprises reacting two molecules of the intermediate α-diketone compound of the present invention, or reacting one molecule of the intermediate α-diketone compound of the present invention and one molecule of a compound having a structure wherein the bicyclo α-diketone moiety of the intermediate α-diketone compound is decomposed.

The α-diketone compound of the present invention is not limited to a compound wherein one aromatic ring is substituted by a bicyclo α-diketone moiety, but may be a compound wherein two or more aromatic rings are substituted by bicyclo α-diketone moieties.

The term "aromatic ring" as used in the present invention means a conjugated ring similar to a benzene ring, and includes, for example, a heteroaromatic ring such as furan ring, thiophene ring, pyrrole ring and imidazole ring, as well as a benzene ring. Also, the term "stereoisomer" as used in the present invention means anisotropy caused by the difference in the steric configuration of atoms or atomic groups in the compounds having the same structural formula, and includes an optical isomer, a geometric isomer, a rotational isomer and the like. Furthermore, the term "substituted or unsubstituted" as used in the present invention regarding an aromatic ring or the like means that the aromatic ring or the like is or is not substituted a substituent.

Effects of the Invention (First Present Invention)

The novel adduct compound of the present invention is obtained by using a Diels-Alder reaction to add in an eliminatable state a double bond-containing compound (II) such as hexachlorocyclopentadiene to a fused polycyclic aromatic compound of formula (I) such as dinaphthothienothiophene, through the double bond. The addition of the double bond-containing compound (II) increases the polarity and/or decreases the crystallinity, and thereby this novel adduct compound of the present invention can have an increased solubility in a solvent. Therefore, according to this novel adduct compound of the present invention, an organic semiconductor layer formed of a fused polycyclic aromatic compound can be formed by using the solution method which is generally easier than the vapor deposition method.

(Second Present Invention)

When the method of the present invention for purifying a fused polycyclic aromatic compound is employed in place of the conventional purification method such as solvent washing, vacuum sublimation purification or the like, or in addition to such a conventional purification method, conventionally unattainable purification can be achieved. It is believed that, in the method of the present invention for purifying a fused polycyclic aromatic compound of formula (I), a double bond-containing compound (II) is added to the fused polycyclic aromatic compound of formula (I), and thereby increase the polarity and/or decrease the crystallinity of the fused polycyclic aromatic compound of formula (I), and in turn, the solubility of the fused polycyclic aromatic compound of formula (I) in the double bond-containing compound (II) and an optional solvent is increased.

Also, according to the method of the present invention for producing a fused polycyclic aromatic compound of formula (I), a fused polycyclic aromatic compound of formula (I) having a conventionally unattainable purity and/or being deprived of impurities that have been difficult to remove, can be produced.

(Third Present Invention)

The first and second adduct compounds are obtained by using a Diels-Alder reaction to add in an eliminatable state a double bond-containing compound (II) such as hexachlorocyclopentadiene to a fused polycyclic aromatic compound of formula (I) such as dinaphthothienothiophene, through the double bond. The addition of the double bond-containing compound (II) increases the polarity and/or decreases the crystallinity of the compound, and thereby these adduct compounds can have a increased solubility in a solvent. Therefore, according to the semiconductor film-forming solution of the present invention containing these adduct compounds, an organic semiconductor layer formed of a fused polycyclic aromatic compound can be formed by using the solution method which is generally easier than the vapor deposition method.

Also, the semiconductor film-forming solution of the present invention contains a specific compound as the crystallization inhibitor, and therefore crystallization of the first adduct compound can be suppressed at the time of forming an organic semiconductor film by the solution method, and thereby an excellent organic semiconductor film can be provided and/or an organic semiconductor film can be efficiently provided.

(Fourth Present Invention)

The bicyclo α-diketone moiety of the novel α-diketone compound of the present invention increases the polarity and/or decreases the crystallinity of the compound, and thereby the compound can have relatively high solubility in a solvent. Also, in the novel α-diketone compound of the present invention, the bicyclo α-diketone moiety is decomposed into a benzene ring moiety by light irradiation, and particularly the bicyclo α-diketone moiety is decomposed into a benzene ring moiety and carbon monoxide in order to obtain the benzene ring moiety, and thereby a fused polycyclic aromatic compound, and particularly a fused polycyclic aromatic compound usable as an organic semiconductor compound, can be obtained.

Therefore, according to this novel α-diketone compound of the present invention, an organic semiconductor layer formed of a fused polycyclic aromatic compound can be formed by using the solution method which is generally easier than the vapor deposition method. Also, according to the novel α-diketone compound of the present invention, the necessity of heating to obtain a fused polycyclic aromatic compound by decomposition can be reduced or eliminated, so that an organic semiconductor layer can be formed on an organic substrate at a relatively low temperature.

BRIEF DESCRIPTION OF THE DRAWINGS

FIG. 17 is a photograph showing the solid matter obtained from the organic semiconductor film-forming solution of Example 3-1.

FIG. 18 is a photograph showing the organic semiconductor film of FET obtained from the organic semiconductor film-forming solution of Example 3-1.

MODE FOR CARRYING OUT THE INVENTION

Figure 1:
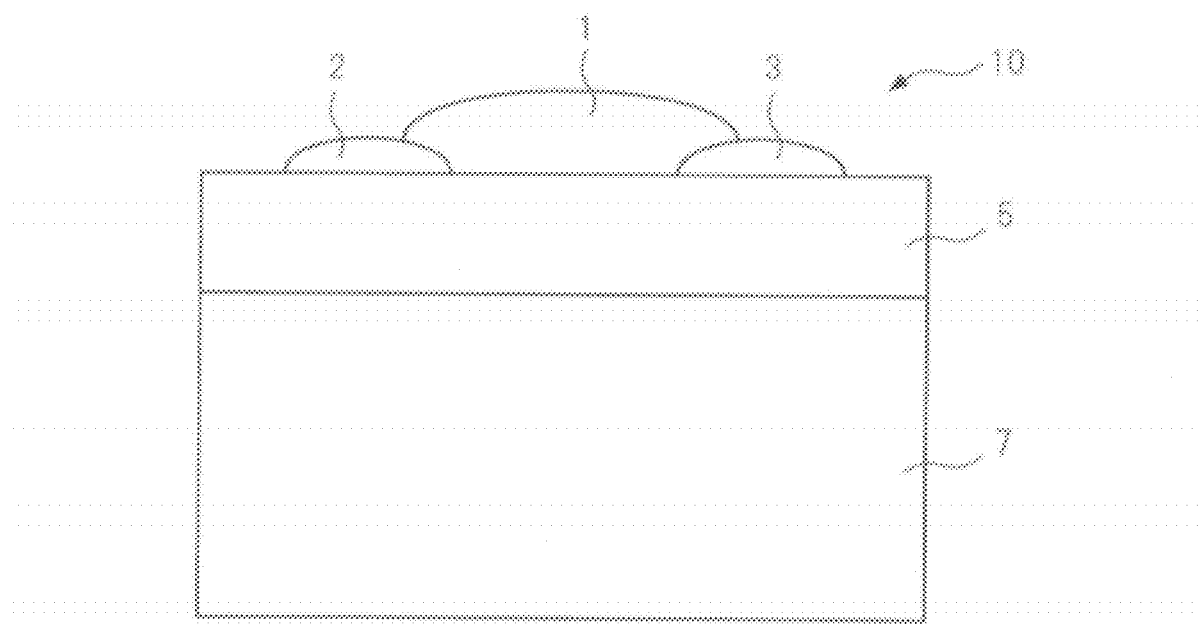
FIG. 1 is a schematic view of the structure of the field effect transistor (FET) used in Example 1-1A and Comparative Example 1-1A.

<<<<First Present Invention>>>>
<<Adduct Compound>>

The adduct compound of the present invention has a structure wherein a double bond-containing compound (II) is added in an eliminatable state to a fused polycyclic aromatic compound of the following formula (I) through the double bond:

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms).

In the adduct compound of the present invention, a double bond-containing compound (II) being added "in an eliminatable state" to a fused polycyclic aromatic compound of formula (I) means that the adduct compound of the present invention can eliminate the double bond-containing compound (II), and particularly eliminate the double bond-containing compound (II), for example, by depressurization and/or heating without decomposing the fused polycyclic aromatic compound of formula (I).

For example, the adduct compound of the present invention has a structure wherein a compound of the following formula (II-1) as an example of the double bond-containing compound (II) is added to a compound of the following formula (I-4) as an example of the fused polycyclic aromatic compound of formula (I), and therefore is a compound having the following formula (III-1) or a stereoisomer thereof:

[Chem. 2]

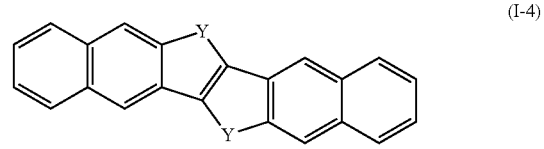

(wherein each Y is independently an element selected from the group consisting of chalcogens, and the fused benzene ring moiety is substituted or unsubstituted);

[Chem. 3]

(wherein each R is independently selected from the group consisting of hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms);

[Chem. 4]

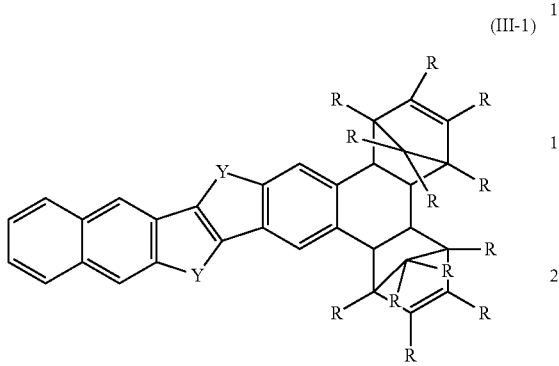

(III-1)

(wherein Y, R and the fused benzene ring moiety are as described above).

Also, for example, the adduct compound of the present invention has a structure wherein a compound of the following formula (II-6) as an example of the double bond-containing compound (II) is added to a compound of the following formula (I-4) as an example of the fused polycyclic aromatic compound of formula (I), and therefore is a compound having the following formula (III-6) or a stereoisomer thereof:

[Chem. 5]

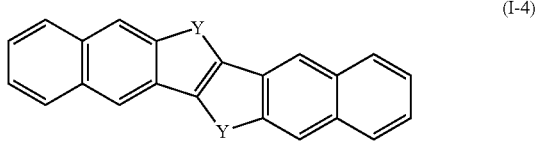

(I-4)

(wherein each Y is independently an element selected from the group consisting of chalcogens, and the fused benzene ring moiety is substituted or unsubstituted);

[Chem. 6]

(II-6)

(wherein each of R and $R_{r'}$ is independently selected from the group consisting of hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms);

[Chem. 7]

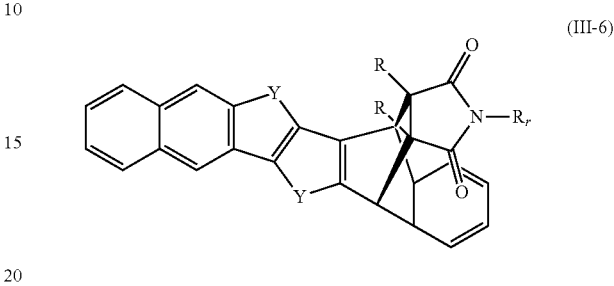

(III-6)

(wherein Y, R, $R_{r'}$ and the fused benzene ring moiety are as described above).

<<First Synthesis Method of Adduct Compound>>

The adduct compound of the present invention can be produced by a method of mixing a fused polycyclic aromatic compound of formula (I) with a double bond-containing compound (II). At this time, the double bond-containing compound (II) may be used by dissolving it in a solvent, but may also be used by itself. As the solvent, any solvent capable of dissolving the double bond-containing compound (II) can be used. For example, the usable solvent includes an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane.

In the synthesis of the adduct compound of the present invention, the reaction may be also accelerated by heating and/or light irradiation when the fused polycyclic aromatic compound of formula (I) and the double bond-containing compound (II) are mixed. The reaction temperature at the synthesis of the adduct compound of the present invention may be determined by taking into consideration the production rate, the stability of component, the boiling point of component, and the like. The temperature may be 20° C. or more, 50° C. or more, or 100° C. or more, and 180° C. or less, 200° C. or less, or 220° C. or less. Also, the reaction time may be, for example, 1 minute or more, 10 minutes or more, 30 minutes or more, or 1 hour or more, and 1 day or less, 3 days or less, 5 days or less, or 10 days or less.

<<Intermediate Adduct Compound and Second Synthesis Method of Adduct Compound>>

The intermediate adduct compound of the present invention has a structure wherein a double bond-containing compound (II) is added to a compound of the following formula (I') through the double bond:

$$Ar_1Q \qquad (I')$$

{wherein $Ar_1$ is selected from the group consisting of substituted or unsubstituted fused aromatic ring moieties each formed of 2 to 5 aromatic rings fused together, and Q has the following formula and constitutes a part of the fused aromatic ring of $Ar_1$:

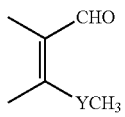

(wherein Y is an element selected from the group consisting of chalcogens)}.

Specifically, for example, the compound of formula (I') may be a compound of the following formula:

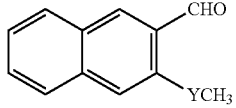

This intermediate adduct compound of the present invention can be obtained by adding the double bond-containing compound (II) to the compound of formula (I'). As for the reaction conditions of this addition reaction, the descriptions related to the reaction of adding the double bond-containing compound (II) to the compound of formula (I) can be referred to.

The method for synthesizing the above-described adduct compound of the present invention from this intermediate adduct compound includes the following steps (a) and (b):

(a) reacting two molecules of the intermediate adduct compound of the present invention to obtain a compound of the following formula:

$Ar_1Q=QAr_1$ (wherein Q=Q represents the following structure:

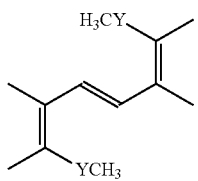

and (b) reacting the obtained compound of formula $Ar_1Q=QAr_1$ with iodine.

According to this method, the adduct compound of the present invention having a structure wherein a double bond-containing compound (II) is added in an eliminatable state to a fused polycyclic aromatic compound of the following formula (I(a1)) through the double bond can be produced:

$Ar_1Ar_{2(a1)}Ar_1$ (I(a1))

(wherein $Ar_1$ is selected from the group consisting of substituted or unsubstituted fused aromatic ring moieties each formed of 2 to 5 aromatic rings fused together, $Ar_{2(a1)}$ is a fused aromatic ring moiety of the following formula (a1):

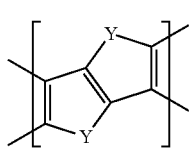

and $Ar_1$ and $Ar_{2(a1)}$ form a fused aromatic ring by sharing at least two carbon atoms).

As for the conditions and the like of the method to synthesize the adduct compound of the present invention from the intermediate adduct compound above, the descriptions in Non-Patent Document 1 can be referred to. That is, for example, the reaction of two molecules of the intermediate adduct compound in the step (a) can be performed in tetrahydrofuran by using a tetrachlorotitanium/zinc (TiCl$_4$/Zn) catalyst. Also, the reaction of formula $Ar_1(Q=Q)Ar_1$ and iodine in the step (b) can be performed in trichloromethane (i.e., chloroform) (CHCl$_3$).

<<Fused Polycyclic Aromatic Compound of Formula (I)>>

With respect to the fused polycyclic aromatic compound of formula (I), each of $Ar_1$ and $Ar_3$ is independently selected from the group consisting of substituted or unsubstituted fused aromatic ring moieties each formed of 2 to 5 aromatic rings fused together, and particularly those formed of 2 to 4 aromatic rings fused together. $Ar_1$ and $Ar_3$ can be selected so that, when the Diels-Alder reaction is performed, they can work as a diene moiety or a dienophilic moiety in order for the double bond-containing compound (II) to add to the moiety in an eliminatable state. The aromatic ring is particularly a substituted or unsubstituted benzene ring. $Ar_1$ and $Ar_3$ may be the same as or different from each other.

Accordingly, each of $Ar_1$ and $Ar_3$ may be independently a substituted or unsubstituted benzene ring moiety selected from the group consisting of the following (b1) to (b4):

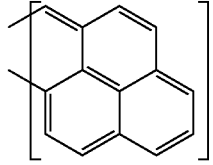 (b1)

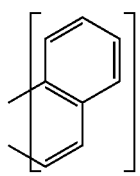 (b2)

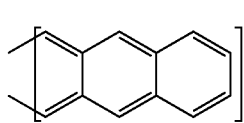 (b3)

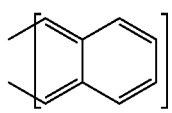 (b4)

Also, with respect to the fused polycyclic aromatic compound of formula (I), $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, and particularly formed of 2 to 3 aromatic rings fused together.

Accordingly, $Ar_2$ may be a substituted or unsubstituted aromatic ring moiety or fused aromatic ring moiety selected from the group consisting of the following (a1) to (a4):

[Chem. 13]

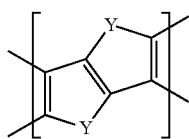
(a1)

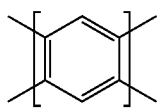
(a2)

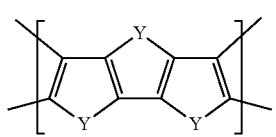
(a3)

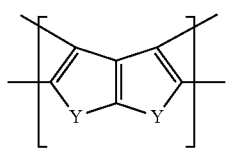
(a4)

(wherein each Y is independently an element selected from the group consisting of chalcogens, particularly an element selected from the group consisting of oxygen (O), sulfur (S), selenium (Se) and tellurium (Te), more particularly sulfur, and all Y may be the same or a part thereof may be different).

The fused polycyclic aromatic compound of formula (I) is preferably an organic semiconductor compound, i.e., an organic compound exhibiting properties as a semiconductor. Also, the fused polycyclic aromatic compound of formula (I) can be selected from the group consisting of substituted or unsubstituted fused polycyclic aromatic compounds of the following formulae (I-1) to (I-5). These fused polycyclic aromatic compounds have high stability, and therefore can be maintained stably at the elimination of the double bond-containing compound (II) form the adduct compound of the present invention, particularly at the elimination by heating, more particularly at the elimination by heating at a relatively high temperature and/or for a long time. Accordingly, when such a compound is used, the elimination of the double bond-containing compound (II) from the adduct compound of the present invention can be performed at a high rate.

[Chem. 14]

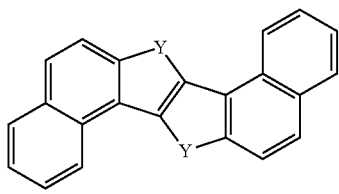
(I-1)

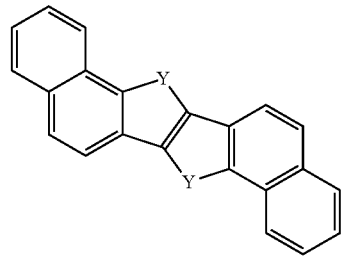
(I-2)

-continued

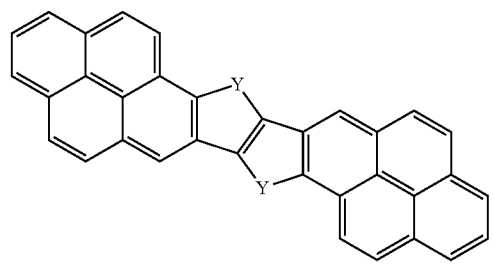
(I-3)

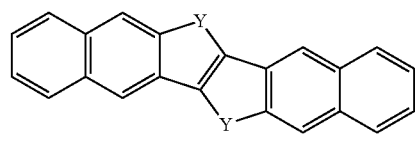
(I-4)

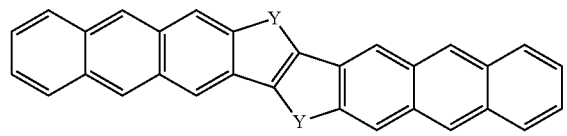
(I-5)

(wherein each Y is independently an element selected from the group consisting of chalcogens, particularly an element selected from the group consisting of oxygen (O), sulfur (S), selenium (Se) and tellurium (Te), more particularly sulfur, and all Y may be the same or a part thereof may be different).

Although the fused polycyclic aromatic compound of formula (I) and its synthesis method are not particularly limited, Patent Documents 1 to 5 and Non-Patent Document 1 can be referred to.

Incidentally, the substitution on the aromatic ring moiety and/or fused aromatic ring moiety of the fused polycyclic aromatic compound of formula (I) is made, for example, with a substituent selected from the group consisting of halogens, alkyl groups having from 1 to 20 carbon atoms, alkenyl groups having from 2 to 20 carbon atoms, alkynyl groups having from 2 to 20 carbon atoms, substituted or unsubstituted aromatic groups having from 4 to 20 carbon atoms, ester groups having from 2 to 10 carbon atoms, ether groups having from 1 to 20 carbon atoms, ketone groups having from 1 to 20 carbon atoms, amino groups having from 1 to 20 carbon atoms, amide groups having from 1 to 20 carbon atoms, imide groups having from 1 to 20 carbon atoms, and sulfide groups having from 1 to 20 carbon atoms.

<<Double Bond-Containing Compound (II)>>

The double bond-containing compound (II) may be any compound capable of being added in an eliminatable state to the fused polycyclic aromatic compound of formula (I). Accordingly, for example, the double bond-containing compound (II) may be any compound capable of being added in an eliminatable state as a dienophile or a conjugated diene to the fused polycyclic aromatic compound of formula (I), particularly by the Diels-Alder reaction. Also, the double bond-containing compound (II) may be any compound capable of being added in an eliminatable state to at least one of aromatic ring moiety or fused aromatic ring moiety out of $Ar_1$, $Ar_2$ and $Ar_3$ of the fused polycyclic aromatic compound of formula (I), more particularly at least one of fused aromatic ring moiety out of $Ar_1$ and $Ar_3$ of the fused polycyclic aromatic compound of formula (I).

In the case where the double bond-containing compound (II) is a dienophile, the double bond-containing compound (II) may be either one compound of the following formulae (II-A1) or (II-B1):

[Chem. 15]

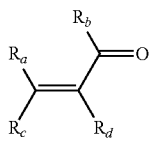
(II-A1)

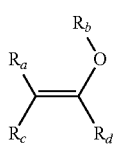
(II-B1)

(wherein each of $R_a$, $R_b$, $R_c$ and $R_d$ is independently selected from the group consisting of bonds, hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms, $R_a$ and $R_b$ may combine with each other to form a ring, and $R_c$ and $R_d$ may combine with each other to form a ring).

The compound of formula (II-A1) may be preferred, because, due to the presence of the carbon-oxygen double bond moiety, the carbon-carbon double bond moiety adjacent to the carbon atom of the moiety above is relatively electrophilic, and thereby accelerates as a dienophile the Diels-Alder reaction. Similarly, the compound of formula (II-B1) may be preferred, because, due to the presence of oxygen, the carbon-carbon double bond moiety adjacent to the oxygen atom is relatively electrophilic, and thereby accelerates as a dienophile the Diels-Alder reaction.

Also, in the case where the double bond-containing compound (II) is a dienophile, the double bond-containing compound (II) may be either one of the following formulae (II-A2) and (II-B2):

[Chem. 16]

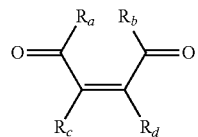
(II-A2)

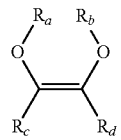
(II-B2)

(wherein each of $R_b$, $R_c$, $R_d$ and $R_e$ is independently selected from the group consisting of bonds, hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms, $R_e$ and $R_b$ may combine with each other to form a ring, and $R_c$ and $R_d$ may combine with each other to form a ring).

The compound of formula (II-A2) may be preferred, because due to the presence of two carbon-oxygen double bond moieties, the carbon-carbon double bond moiety between their carbon atoms is relatively electrophilic, and thereby accelerates as a dienophile the Diels-Alder reaction. Similarly, the compound of formula (II-B2) may be preferred, because, due to the presence of two oxygens, the carbon-carbon double bond moiety between those oxygen atoms is relatively electrophilic, and thereby accelerates as a dienophile the Diels-Alder reaction.

Furthermore, in the case where the double bond-containing compound (II) is a dienophile, the double bond-containing compound (II) may be either one of the following formulae (II-A3) and (II-B3):

[Chem. 17]

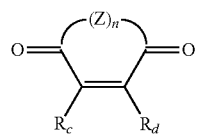
(II-A3)

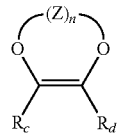
(II-B3)

(wherein each of $R_c$ and $R_d$ is independently selected from the group consisting of bonds, hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms, $R_c$ and $R_d$ may combine with each other to form a ring, n is an integer of 1 to 5, and Z is selected from the group consisting of bonds (—), oxygen (—O—), a methylenic carbon (—C($R_r$)$_2$—), an ethylenic carbon (—C($R_r$)=), a carbonyl group (—C(=O)—), nitrogen (—N($R_r$)—), and sulfur (—S—), and when n is 2 or greater, each may be the same or different from each other (each $R_r$ is independently selected from the group consisting of hydrogen, halogens, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms)).

The compound of formula (II-A3) may be preferred, because, due to the presence of two carbon-oxygen double bond moieties, the carbon-carbon double bond moiety between their carbon atoms is relatively electrophilic, and thereby accelerates as a dienophile the Diels-Alder reaction. Similarly, the compound of formula (II-B3) may be preferred, because, due to the presence of two oxygens, the carbon-carbon double bond moiety between those oxygen atoms is relatively electrophilic, and thereby accelerates as a dienophile the Diels-Alder reaction. Also, the compound of formula (II-A3) or (II-B3) may be preferred in order to be added in an eliminatable state to the fused polycyclic aromatic compound of formula (I), because a double bond forms a part of a cyclic structure, and this makes such a compound to be structurally stable.

Incidentally, the conjugated diene-type double bond-containing compound (II) is added as a dienophile and/or a conjugated diene to the fused polycyclic aromatic compound of formula (I) in the Diels-Alder reaction, depending on the combination with the fused polycyclic aromatic compound of formula (I).

The double bond-containing compound (II) may be a compound having a cyclic moiety. The double bond preferably form a part of a cyclic structure, and thereby the double bond-containing compound (II) is structurally stabilized, in order for the double bond-containing compound (II) to be added in an eliminatable state to the fused polycyclic aromatic compound of formula (I).

Accordingly, for example, the double bond-containing compound (II) may be any one of the following formulae (II-1) to (II-12):

[Chem. 18]

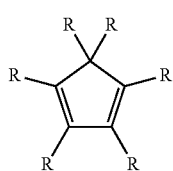

(II-1)

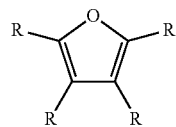

(II-2)

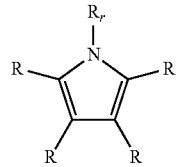

(II-3)

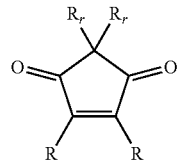

(II-4)

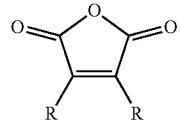

(II-5)

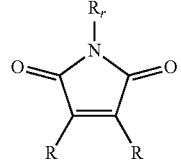

(II-6)

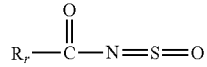

(II-7)

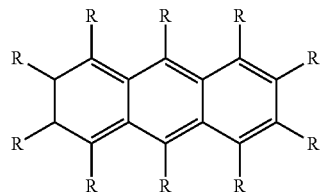

(II-8)

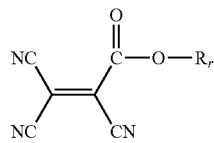

(II-9)

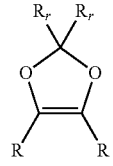

(II-10)

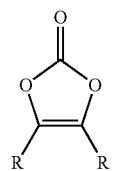

(II-11)

-continued

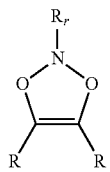

(II-12)

(wherein each of R and $R_r$ is independently selected from the group consisting of hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms).

The double bond-containing compound (II) may be a conjugated diene-type compound, for example, any one compound of formulae (II-1) to (II-3) and (II-8). Also, the double bond-containing compound (II) may be a dienophile-type compound, for example, any one compound of formulae (II-4) to (II-6), (II-9) and (II-10) to (II-12). Furthermore, the double bond-containing compound (II) may be a compound having a cyclic moiety, for example, any one compound of formulae (II-1) to (II-6), (II-8) and (II-10) to (II-12).

Incidentally, regarding R and $R_r$ of any one compound of formulae (II-1) to (II-12), the substituent of the aromatic group having from 4 to 10 carbon atoms can be the substituent which may be substituted on the aromatic ring moiety or fused aromatic ring moiety of the fused polycyclic aromatic compound of formula (I).

In the following, each compound of formulae (II-1) to (II-12) is described in more detail.

<<Compound of Formula (II-1)>>

[Chem. 19]

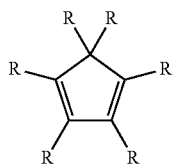

(II-1)

(wherein R is as described above).

Particularly, in the compound of formula (II-1), each R is independently selected from the group consisting of hydrogen and halogens. When R is a halogen, each R may be independently an element selected from the group consisting of fluorine (F), chlorine (Cl), bromine (Br), iodine (I) and a combination thereof, particularly an element selected from the group consisting of fluorine (F), chlorine (Cl) and a combination thereof, more particularly chlorine. Accordingly, the compound of formula (II-1) may be, for example, hexafluorocyclopentadiene, hexachlorocyclopentadiene, hexabromocyclopentadiene, 5,5-difluorotetrachlorocyclopentadiene or 5,5-dibromotetrachlorocyclopentadiene, particularly hexachlorocyclopentadiene. Also, in the case where all R are hydrogen, the compound of formula (II-1) is cyclopentadiene.

<<Compound of Formula (II-2)>>

[Chem. 20]

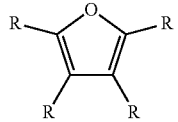

(II-2)

(wherein R is as described above).

In particular, in the compound of formula (II-2), each R is independently selected from the group consisting of hydrogen and halogens. When all R are hydrogen, the compound of formula (II-2) is furan.

<<Compound of Formula (II-3)>>

[Chem. 21]

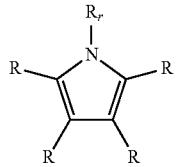

(II-3)

(wherein R and $R_r$ are as described above).

In particular, in the compound of formula (II-3), each R is independently selected from the group consisting of hydrogen and halogens. Also, particularly, $R_r$ is an ester group having from 1 to 10 carbon atoms, for example, a methyl ester. Accordingly, in particular, the compound of formula (II-3) may be a compound wherein R is hydrogen and $R_r$ is an alkyl ester group having from 1 to 10 carbon atoms, i.e., an alkyl pyrrolecarboxylate, for example, methylpyrrolecarboxylate wherein R is hydrogen and $R_r$ is a methyl ester group.

<<Compound of Formula (II-4)>>

[Chem. 22]

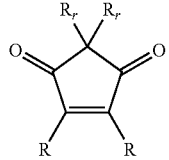

(II-4)

(wherein R and $R_r$ are as described above).

In particular, in the compound of formula (II-4), $R_r$ is preferably a group other than hydrogen, i.e., a relatively bulky group in order to expedite elimination of the compound of formula (II-4) from the adduct compound made of the fused polycyclic aromatic compound of formula (I) and the compound of formula (II-4) by heating or the like.

<<Compound of Formula (II-5)>>

[Chem. 23]

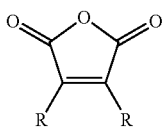
(II-5)

(wherein R is as described above).

In particular, when both R are hydrogen in the compound of formula (II-5), the compound is a maleic anhydride. Accordingly, the compound of formula (II-5) can be considered as a maleic anhydride or a compound wherein a hydrogen group of the maleic anhydride is substituted.

<<Compound of Formula (II-6)>>

[Chem. 24]

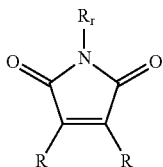
(II-6)

(wherein R and $R_r$ are as described above).

In particular, in the compound of formula (II-6), each R is independently selected from the group consisting of hydrogen and halogens. Also, particularly, $R_r$ is alkyl groups having from 1 to 10 carbon atoms, or substituted or unsubstituted aromatic groups having from 4 to 10 carbon atoms, for example, a hydroxyphenyl group.

Accordingly, for example, the compound of formula (II-6) may be N-methylmaleimide wherein R is hydrogen and $R_r$ is a methyl group, or N-ethylmaleimide wherein R is hydrogen and $R_r$ is an ethyl group. Also, for example, the compound of formula (II-6) may be a compound wherein R is hydrogen and $R_r$ is substituted or unsubstituted aromatic groups having from 4 to 10 carbon atoms, i.e., an aromatic maleimide, particularly N-phenylmaleimide wherein R is hydrogen and $R_r$ is a phenyl group, or hydroxyphenylmaleimide wherein R is hydrogen and $R_r$ is a hydroxyphenyl group.

<<Compound of Formula (II-7)>>

[Chem. 25]

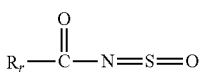
(II-7)

(wherein $R_r$ is as described above).

In particular, in the compound of formula (II-7), $R_r$ is selected from the group consisting of alkyl groups having from 1 to 10 carbon atoms. Accordingly, the compound of formula (II-7) may be a compound wherein $R_r$ is an alkyl group, i.e., N-sulfonylacylamide, for example, N-sulfonylacetamide wherein $R_r$ is a methyl group.

<<Compound of Formula (II-8)>>

[Chem. 26]

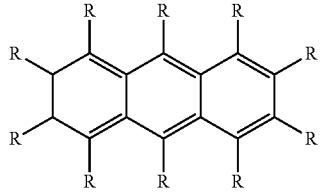
(II-8)

(wherein R is as described above).

In particular, in the compound of formula (II-8), each R is independently selected from the group consisting of hydrogen and halogens. When R is a halogen, each R is independently an element selected from the group consisting of fluorine (F), chlorine (Cl), bromine (Br), iodine (I) and a combination thereof. Also, in the case where all R are hydrogen, the compound of formula (II-8) is anthracene.

<<Compound of Formula (II-9)>>

[Chem. 27]

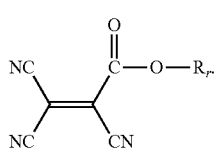
(II-9)

(wherein $R_r$ is as described above).

In particular, in the compound of formula (II-9), $R_r$ is selected from the group consisting of alkyl groups having from 1 to 10 carbon atoms. Accordingly, the compound of formula (II-9) may be a compound wherein $R_r$ is an alkyl group, i.e., tricyano alkyl carboxylate-ethylene, for example, tricyano methyl carboxylate-ethylene wherein $R_r$ is a methyl group.

<<Compound of Formula (II-10)>>

[Chem. 28]

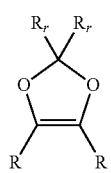
(II-10)

(wherein R and $R_r$ are as described above).

<<Compound of Formula (II-11)>>

[Chem. 29]

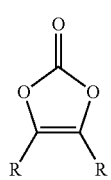
(II-11)

(wherein R is as described above).

In particular, in the compound of formula (II-11), each R is independently selected from the group consisting of hydrogen and halogens. When all R are hydrogen, the compound of formula (II-11) is vinylene carbonate.

<<Compound of Formula (II-12)>>

[Chem. 30]

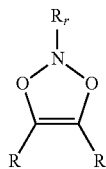

(II-12)

(wherein R and $R_r$ are as described above).

<<Adduct Compound-Containing Solution>>

The adduct compound-containing solution of the present invention comprises the adduct compound of the present invention dissolved in a solvent, particularly in an organic solvent.

The adduct compound-containing solution may contain the adduct compound of the present invention in any concentration, and, for example, may contain the adduct compound of the present invention in a concentration of 0.01 to 20 mass %, from 0.05 to 10 mass %, or from 0.1 to 5 mass %.

The solvent which can be used in the adduct compound-containing solution can be any solvent capable of dissolving the adduct compound of the present invention. For example, the usable solvent includes an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane.

In the case where the adduct compound of the present invention has a stereoisomer, the solution of the present invention may comprise, for example, the adduct compound of the present invention and at least one stereoisomer thereof dissolved in a solvent, and the proportion of a stereoisomer having a lowest thermal elimination temperature based on the total amount of the adduct compound and a stereoisomer thereof [stereoisomer having a lowest thermal elimination temperature out of the adduct compound and a stereoisomer thereof/the adduct compound and a stereoisomer thereof] may be more than 50 mol %, more than 70 mol %, more than 90 mol %, or more than 95 mol %.

Also, in the case where the adduct compound of the present invention has Exo and Endo forms as the stereoisomer, the solution of the present invention may comprise the Exo and Endo forms of the adduct compound of the present invention in a solvent, and the proportion of a stereoisomer having a lower thermal elimination temperature based on the total amount of the Exo and Endo forms of the adduct compound of the present invention [stereoisomer having a lower thermal elimination temperature out of the Exo and Endo forms/(Exo form+Endo form)] may be more than 50 mol %, more than 70 mol %, more than 90 mol %, or more than 95 mol %. Accordingly, the solution of the present invention may comprises Exo and Endo forms of the adduct compound of formula (III-6) dissolved in a solvent, and the proportion of the Exo form based on the total amount of the Exo and Endo forms of the adduct compound above [Exo form/(Exo form+Endo form)] may be more than 50 mol %, more than 70 mol %, more than 90 mol %, more than 95 mol %, or more than 99 mol %.

In the case where the adduct compound-containing solution of the present invention contains a stereoisomer having a relatively low thermal elimination temperature in a relatively large ratio, at the time of eliminating the double bond-containing compound (II) from the solution and removing the double bond-containing compound (II) by heating to obtain an organic semiconductor film formed of the fused polycyclic aromatic compound of formula (I), the elimination can be started at a relatively low temperature. Accordingly, in this case, an organic semiconductor film can be produced at a relatively low temperature.

Incidentally, in the Diels-Alder reaction, a reaction product wherein a substituent is present on the side opposite to the main bridge is defined as an Endo form, and a reaction product wherein a substituent is present on the same side as the main bridge is defined as an Exo form.

<<Production Method of Organic Semiconductor Film>>

The method of the present invention for producing an organic semiconductor film comprises coating the adduct compound-containing solution of the present invention on a substrate to form a film, and eliminating the double bond-containing compound (II) from the adduct compound and removing the double bond-containing compound (II) by depressurizing and/or heating the film to obtain an organic semiconductor film formed of the fused polycyclic aromatic compound of formula (I).

The coating of this solution on a substrate can be performed in any manner, and, for example, may be performed by a casting method, a spin coating method or a printing method. The coating of the solution on a substrate may be performed also by simply dropping the solution on a substrate.

In the case of eliminating and removing the compound (II) by heating and/or depressurization, any conditions causing substantially no decomposition of the fused polycyclic aromatic compound of formula (I) can be employed. Accordingly, the elimination and removal of the compound (II) can be performed, for example, by heating at a temperature of 80° C. or more, 100° C. or more, 120° C. or more, or 140° C. or more, and 200° C. or less, 220° C. or less, 240° C. or less, or 260° C. or less. Also, the elimination and removal of the compound (II) can be performed, for example, in a vacuum or under an atmospheric pressure. Furthermore, the elimination and removal of the compound (II) can be performed, for example, in a nitrogen atmosphere or an air atmosphere. In particular, the elimination and removal of the compound (II) is preferably performed in an air atmosphere under an atmospheric pressure, because production of the film formed of the fused polycyclic aromatic compound of formula (I) is facilitated.

In the method of the present invention for producing an organic semiconductor film, the elimination and removal of the double bond-containing compound (II) can be preformed by rapid heating, i.e., for example, by heating at a heating rate of more than 100° C./min, 200° C./min, 400° C./min, 600° C./min, 800° C./min, or 1,000° C./min. Such rapid heating can be achieved, for example, by bringing the substrate having a film into direct contact with a heated material such as heated electric heater, by introducing the substrate having a film into a heated region such as heated furnace, by radiating an electromagnetic wave such as microwave, or by simultaneously performing some of these operations. Also, the rapid heating can be performed to a temperature 3° C. or more, 5°

C. or more, or 10° C. or more, higher than the temperature at which the elimination and removal of the double bond-containing compound (II) starts.

In the case of performing the elimination of the double bond-containing compound (II) by rapid heating, an organic semiconductor film having a large crystal of the fused polycyclic aromatic compound of formula (I), for example, a crystal with a long axis diameter of more than 5 μm of the fused polycyclic aromatic compound of formula (I), can be formed.

It is believed that, in the case of performing the elimination and removal of the double bond-containing compound (II) by rapid heating, rearrangement due to thermal motion of the fused polycyclic aromatic compound of formula (I) occurs at the same time as the elimination of the double bond-containing compound (II), and in turn, due to the crystallinity of the fused polycyclic aromatic compound of formula (I), crystallization of the fused polycyclic aromatic compound of formula (I) is accelerated. On the other hand, in the case of eliminating of the double bond-containing compound (II) by slow heating, it is believed that, along with elimination of the double bond-containing compound (II) from the adduct compound, crystallization of the fused polycyclic aromatic compound of formula (I) proceeds at many sites to produce a large number of crystal nuclei, and thereby individual crystals of the fused polycyclic aromatic compound of formula (I) become small in the finally obtained organic semiconductor film.

<<Production Method of Organic Semiconductor Device>>

The method of the present invention for producing an organic semiconductor device comprises producing an organic semiconductor film by the method of the present invention for producing an organic semiconductor film. This method may optionally further comprise forming an electrode layer and/or a dielectric layer above or below the organic semiconductor film.

<<Organic Semiconductor Device>>

The organic semiconductor device of the present invention is an organic semiconductor device having an organic semiconductor film, wherein the organic semiconductor film is formed of a fused polycyclic aromatic compound of formula (I) having a structure wherein the double bond-containing compound (II) is eliminated from the adduct compound of the present invention, and the organic semiconductor film contains the adduct compound of the present invention.

The expression that the organic semiconductor film contains the adduct compound of the present invention means that the organic semiconductor film contains the adduct compound of the present invention in a detectable amount. Accordingly, for example, the molar ratio of the adduct compound of the present invention may be more than 1 ppm, more than 10 ppm, more than 100 ppm, more than 1,000 ppm, or more than 10,000 ppm (1%). Also, the proportion of the adduct compound of the present invention may be 10 mol % or less, 5 mol % or less, 3 mol % or less, 1 mol % or less, 0.1 mol % or less, or 0.01 mol % or less.

Such an organic semiconductor device of the present invention can have characteristics as an organic semiconductor device, despite containing the adduct compound of the present invention as well as the fused polycyclic aromatic compound of formula (I). That is, in the case of producing an organic semiconductor film of the organic semiconductor device of the present invention from the adduct compound of the present invention, even when the thermal elimination reaction of the adduct compound of the present invention does not proceed completely, the organic semiconductor device of the present invention can have characteristics as a semiconductor device. This is preferred to facilitate the production of the organic semiconductor device of the present invention or an organic semiconductor film thereof.

Another organic semiconductor device of the present invention is an organic semiconductor device having an organic semiconductor film, wherein the organic semiconductor film has a crystal with a long axis diameter of more than 5 μm, more than 10 μm, more than 20 μm, more than 30 μm, more than 40 μm, more than 50 μm, more than 60 μm, more than 70 μm, more than 80 μm, more than 90 μm, or more than 100 μm, of a fused polycyclic aromatic compound of the following formula (I):

$$Ar_1Ar_2Ar_3 \qquad (I)$$

(wherein $Ar_1$, $Ar_2$ and $Ar_3$ are as described above).

In this organic semiconductor device of the present invention, the organic semiconductor film has a large crystal, and thereby the semiconductor characteristics, for example, the carrier mobility and on/off ratio, of the organic semiconductor film can be improved.

The organic semiconductor film for these organic semiconductor devices can be obtained, for example, by the solution method, that is, by an organic semiconductor film forming method comprising coating a solution on a substrate and removing the solvent from the solution, and particularly by the method of the present invention for producing an organic semiconductor film.

Still another organic semiconductor device of the present invention is an organic semiconductor device having an organic semiconductor film, wherein the organic semiconductor film is formed of a fused polycyclic aromatic compound of formula (I) having a structure wherein the double bond-containing compound (II) is eliminated from the adduct compound of the present invention, the organic semiconductor film contains the adduct compound of the present invention, and the organic semiconductor film has a crystal with a long axis diameter of more than 5 μm of the fused polycyclic aromatic compound of formula (I).

In particular, the organic semiconductor device of the present invention is a thin-film transistor having a source electrode, a drain electrode, a gate electrode, a gate insulating film and the organic semiconductor film; and the thin-film transistor insulates the source electrode and the drain electrode from the gate electrode by the gate insulating film, and controls the current flowing through the organic semiconductor from the source electrode to the drain electrode by the voltage applied to the gate electrode. Also, particularly, the organic semiconductor device of the present invention is a solar cell having the organic semiconductor film as the active layer. Incidentally, the "organic semiconductor device" as used in the present invention means a device having an organic semiconductor film, and other layers such as electrode layer and dielectric layer may be formed of an inorganic material or an organic material.

<<<<Second Present Invention>>>>
<<Purification Method>>

The method of the present invention for purifying a fused polycyclic aromatic compound of the following formula (I) comprises the following steps (a) to (d):

$$Ar_1Ar_2Ar_3 \qquad (I)$$

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms);

(a) providing a crude product of the fused polycyclic aromatic compound of formula (I), (b) providing a double bond-containing compound (II) capable of being added in an eliminatable state to the fused polycyclic aromatic compound of formula (I), (c) mixing the fused polycyclic aromatic compound of formula (I) with the double bond-containing compound (II) to obtain a mixed solution containing an adduct compound of these compounds which is at least partially dissolved therein, and (d) separating and obtaining the purified fused polycyclic aromatic compound of formula (I) from the mixed solution.

<<Purification Method—Step (a)>>

In the step (a), a crude product of the fused polycyclic aromatic compound of formula (I) is provided. The crude product of the fused polycyclic aromatic compound of formula (I) provided can be obtained by any synthesis method. In general, the fused polycyclic aromatic compound of formula (I) is obtained by a synthesis method using a halogen element and/or a metal element or a compound thereof, and/or an aromatic compound, as a reaction medium, a raw material, a catalyst or the like (see, for example, Patent Documents 1 to 5 and Non-Patent Document 1, particularly Patent Document 2). Therefore, according to the purification method of the present invention, such an element or compound contained as an impurity in the crude product of the fused polycyclic aromatic compound of formula (I) can be at least partially removed.

Incidentally, the crude product of formula (I) used in the step (a) may be preferably purified in advance, for example, may be purified in advance by solvent washing, so as to accelerate the purification by the method of the present invention.

The fused polycyclic aromatic compound of formula (I) is illustrated more specifically below.

<<Purification Method—Step (b)>>

In the step (b), a double bond-containing compound (II) capable of being added in an eliminatable state to the fused polycyclic aromatic compound of formula (I), is provided. Incidentally, a double bond-containing compound (II) being added "in an eliminatable state" to a fused polycyclic aromatic compound of formula (I) means that the adduct compound of the fused polycyclic aromatic compound of formula (I) and the double bond-containing compound (II) can eliminate the double bond-containing compound (II), for example, by depressurization and/or heating without decomposing the fused polycyclic aromatic compound of formula (I).

The double bond-containing compound (II) is illustrated more specifically below.

<<Purification Method—Step (c)>>

In the step (c), the fused polycyclic aromatic compound of formula (I) is mixed with the double bond-containing compound (II) to obtain a mixed solution containing an adduct compound of these compounds which is at least partially dissolved therein. This adduct compound is illustrated more specifically below.

The double bond-containing compound (II) may be used together with a solvent, but the double bond-containing compound (II) may be used by itself. The solvent usable for this purpose includes any solvent capable of dissolving the adduct compound obtained in the step (c). For example, the usable solvent includes an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (that is, 1,3,5-trimethylbenzene); aliphatic hydrocarbons such as hexane and heptane; and a halogen-containing solvent such as dichloromethane, chloroform and dichloroethane.

Also, in order to accelerate removal of impurities from the crude product of the compound having formula (I), a radical scavenger such as hydroquinone may be used in combination for the purpose of preventing polymer formation due to self-polymerization by radical polymerization of the double bond-containing compound (II).

In the step (c), the addition-elimination reaction can be also accelerated by the heating and/or light irradiation at the time of mixing of the fused polycyclic aromatic compound of formula (I) and the double bond-containing compound (II). The temperature of the mixed solution of the step (c) can be determined by taking into consideration the addition reaction rate, the stability of component, the boiling point of component, and the like. The temperature may be, for example, 20° C. or more, 50° C. or more, or 100° C. or more, and 180° C. or less, 200° C. or less, or 220° C. or less. Also, the mixed solution can be stored over a predetermined period, for example, can be stored over a period of 1 minute or more, 10 minutes or more, 30 minutes or more, or 1 hour or more, and 1 day or less, 3 days or less, 5 days or less, or 10 days or less.

For reference, FIG. 1 illustrates a conceptual view of the scheme wherein, in the mixed solution of the step (c), impurities are separated from the crude product of the fused polycyclic aromatic compound of formula (I), but the present invention is not limited thereto.

Figure 14:
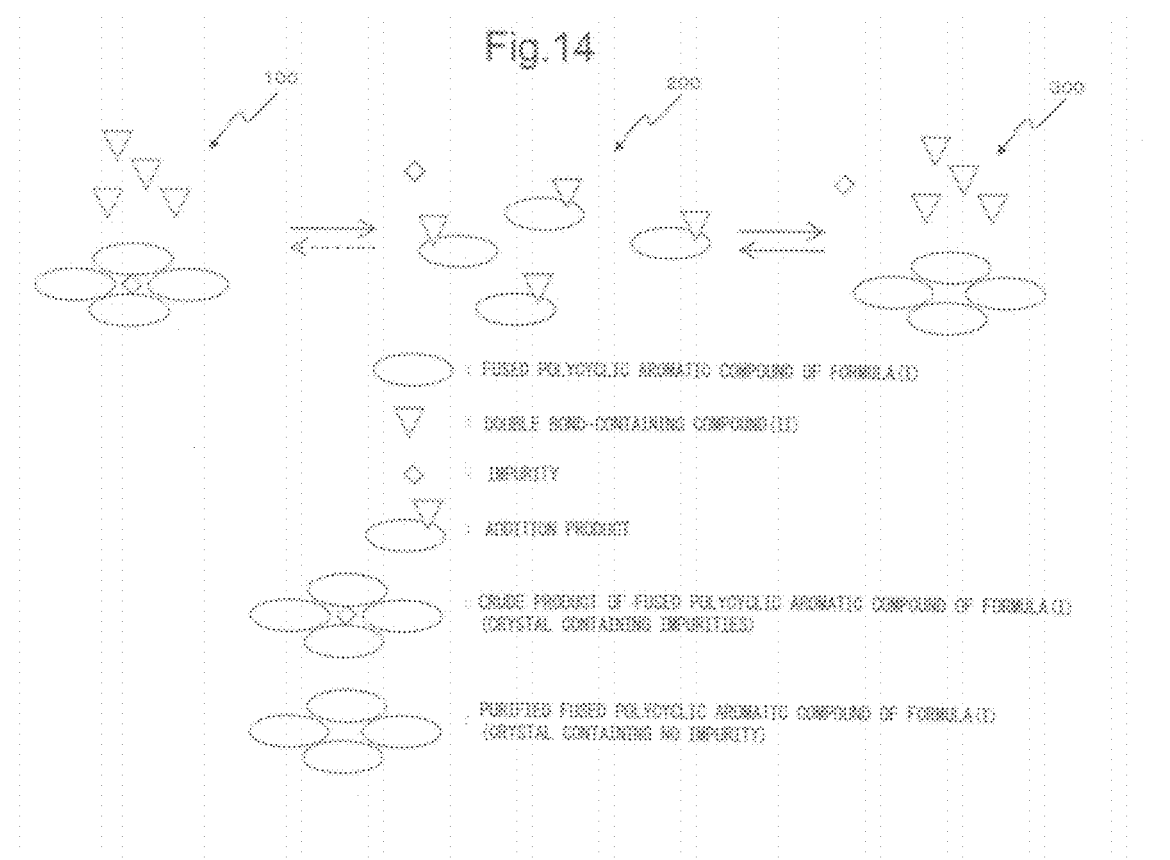
FIG. 14 is a view conceptually showing the scheme of the purification method of the present invention.

In the formula of FIG. 14, left side 100 illustrates the initial condition of the mixture of the fused polycyclic aromatic compound (crude product) of formula (I) in the state of a crystal containing impurities, and the double bond-containing compound (II). In such a mixture, as illustrated in middle side 200 of the formula of FIG. 14, the double bond-containing compound (II) is added in an eliminatable state to the fused polycyclic aromatic compound of formula (I) to decrease the crystallinity of the fused polycyclic aromatic compound of formula (I) and/or increase the polarity of the compound, and thereby the fused polycyclic aromatic compound of formula (I) is dissolved in the mixed solution.

The double bond-containing compound (II) is added in an eliminatable state to the fused polycyclic aromatic compound of formula (I), and therefore, in the formula of FIG. 14, the condition of left side 100, the condition of middle side 200 and the condition of right side 300 are in an equilibrium relationship with each other. However, since the amount of impurities is generally small compared with the double bond-containing compound (II) and the optional solvent, it is understood that the impurity is rarely captured during crystallization of the fused polycyclic aromatic compound of formula (I) from the condition of middle side 200 in the formula of FIG. 14, and therefore, the equilibrium is gradually shifted from the condition of left side 100 of FIG. 14 to the conditions of middle side 200 and right side 300 of FIG. 14.

<<Purification Method—Step (d)>>

In the step (d), the purified fused polycyclic aromatic compound of formula (I) is obtained by separating it from the mixed solution obtained in the step (c). The fused polycyclic aromatic compound of formula (I) in the purified crystal state of the condition of right side 300 of FIG. 14 has a low solubility in the mixed solution, and therefore can be separated by filtration or the like.

The adduct compound in the condition of middle side 200 of FIG. 14 can eliminate and remove the double bond-containing compound (II) from the fused polycyclic aromatic compound of formula (I), for example, by depressurization and/or heating, without decomposing the fused polycyclic aromatic compound of formula (I). This is possible because, as described above, the double bond-containing compound (II) is added in an eliminatable state to the fused polycyclic aromatic compound of formula (I).

In the case of eliminating and removing the compound (II) by heating and/or depressurization, any conditions causing substantially no decomposition of the fused polycyclic aromatic compound of formula (I) can be employed. Accordingly, the elimination of the compound (II) can be performed, for example, by heating at a temperature of 80° C. or more, 100° C. or more, 120° C. or more, or 140° C. or more, and 200° C. or less, 220° C. or less, 240° C. or less, or 260° C. or less. Also, the elimination and removal of the compound (II) can be performed, for example, in a vacuum or under an atmospheric pressure. Furthermore, the elimination and removal of the compound (II) can be performed, for example, in a nitrogen atmosphere or an air atmosphere.

The purified fused polycyclic aromatic compound of formula (I) obtained in the step (d) can be further purified, for example, can be further purified by the sublimation purification method.

<<Production Method 1 of Fused Polycyclic Aromatic Compound>>

The first method of the present invention for producing the fused polycyclic aromatic compound of formula (I) comprises purifying a crude product of the fused polycyclic aromatic compound of formula (I) by the method of the present invention.

<<Production Method 2 of Fused Polycyclic Aromatic Compound>>

The second method of the present invention for producing a fused polycyclic aromatic compound of formula (I) comprises eliminating the double bond-containing compound (II) from an adduct compound having a structure and removing the double bond-containing compound (II) wherein the compound (II) is added in an eliminatable state to the fused polycyclic aromatic compound of formula (I), and particularly eliminating and removing the compound (II) by heating and/or depressurization.

In the case of eliminating and removing the compound (II) by heating and/or depressurization, any conditions causing substantially no decomposition of the fused polycyclic aromatic compound of formula (I) can be employed. Accordingly, the elimination and removal of the compound (II) can be performed, for example, by heating at a temperature of 80° C. or more, 100° C. or more, 120° C. or more, or 140° C. or more, and 200° C. or less, 220° C. or less, 240° C. or less, or 260° C. or less. Also, the elimination and removal of the compound (II) can be performed, for example, in a vacuum or under an atmospheric pressure. Furthermore, the elimination and removal of the compound (II) can be performed, for example, in a nitrogen atmosphere or an air atmosphere. In particular, the elimination and removal of the compound (II) is preferably performed in an air atmosphere under an atmospheric pressure in order to facilitate the production of the fused polycyclic aromatic compound of formula (I).

In the first and second methods of the present invention for producing a fused polycyclic aromatic compound of formula (I), the fused polycyclic aromatic compound of formula (I) can be obtained as a powder. However, the form of the fused polycyclic aromatic compound of formula (I) obtained by these methods of the present invention is not limited to a powder.

<<Production Method of Organic Semiconductor Film>>

The method of the present invention for producing an organic semiconductor film comprises producing the fused polycyclic aromatic compound by the method of the present invention and obtaining an organic semiconductor film from the obtained fused polycyclic aromatic compound of formula (I), for example, by the vapor deposition method.

<<Production Method of Organic Semiconductor Device>>

The method of the present invention for producing an organic semiconductor device comprises producing an organic semiconductor film by the method of the present invention for producing an organic semiconductor film. This method may optionally further comprise forming an electrode layer and/or a dielectric layer above or below the organic semiconductor film.

<<Others>>

As for the adduct product, the fused polycyclic aromatic compound of formula (I), the double bond-containing compound (II), the organic semiconductor device and the like, the descriptions related to the first present invention can be referred to.

<<<<Third Present Invention>>>>

<<Organic Semiconductor Film-Forming Solution>>

The solution of the present invention for forming an organic semiconductor film contains an organic solvent, a first adduct compound dissolved in the organic solvent, and a crystallization inhibitor dissolved in the organic solvent and capable of inhibiting crystallization of the first adduct compound.

The first adduct compound has a structure wherein a first double bond-containing compound (II') is added in an eliminatable state to a fused polycyclic aromatic compound of the following formula (I) through the double bond:

$$Ar_1Ar_2Ar_3 \qquad (I)$$

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms).

Also, the crystallization inhibitor is at least one compound selected from the group consisting of the following (a) to (c):

(a) a second adduct compound having a structure wherein a second double bond-containing compound (II") is added in an eliminatable state to the fused polycyclic aromatic compound of formula (I) through the double bond, (b) the first double bond-containing compound (II'), which is a compound (II') capable of being added in an eliminatable state to the fused polycyclic aromatic compound of formula (I) through the double bond, and (c) the second double bond-containing compound (II"), which is a compound (II") capable of being added in an eliminatable state to the fused polycyclic aromatic compound of formula (I) through the double bond.

In the solution of the present invention for forming an organic semiconductor film, the first adduct compound has a structure wherein a first double bond-containing compound (II') is added in an eliminatable state to the fused polycyclic aromatic compound of formula (I), and thereby this adduct compound has an increased polarity and/or decreased crystallinity, as compared with the fused polycyclic aromatic compound of formula (I), and in turn, has relatively high solubility in the solvent. Therefore, according to the solution of the present invention, an organic semiconductor layer formed of a fused polycyclic aromatic compound can be formed by using the solution method. Specifically, for example, an organic semiconductor film formed of the fused polycyclic aromatic compound of formula (I) can be obtained by coating the solution of the present invention on a substrate to produce a film, and eliminating the double bond-containing first compound (II') from the first adduct compound and removing the double bond-containing compound (II) by depressurizing and/or heating the film.

Also, the solution of the present invention for forming an organic semiconductor film contains a crystallization inhibitor, and therefore crystallization can be suppressed at the time of forming an organic semiconductor film by the solution method, and thereby an excellent organic semiconductor film can be provided and/or an organic semiconductor film can be efficiently provided.

The organic semiconductor film-forming solution of the present invention may contain the first adduct compound in any concentration, and, for example, may contain the first adduct compound in a concentration of 0.01 to 20 mass %, from 0.05 to 10 mass %, or from 0.1 to 5 mass %.

The solvent usable in the organic semiconductor film-forming solution of the present invention includes any solvent capable of dissolving the first adduct compound. For example, the usable solvent includes an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane.

In the case where the first adduct compound has a stereoisomer, the solution of the present invention may comprise, for example, the first adduct compound and at least one stereoisomer thereof dissolved in a solvent, and the proportion of a stereoisomer having a lowest thermal elimination temperature based on the total amount of the adduct compound and a stereoisomer thereof [stereoisomer having a lowest thermal elimination temperature out of the adduct compound and a stereoisomer thereof/the adduct compound and a stereoisomer thereof] may be more than 50 mol %, more than 70 mol %, more than 90 mol %, or more than 95 mol %.

Also, in the case where the first adduct compound has an Exo and Endo forms as the stereoisomer, the solution of the present invention may comprise an Exo and Endo forms of the first adduct compound dissolved in a solvent, and the proportion of a stereoisomer having a lower thermal elimination temperature based on the total amount of the Exo and Endo forms of the first adduct compound {stereoisomer having a lower thermal elimination temperature out of the Exo and Endo forms/(Exo form+Endo form)} may be more than 50 mol %, more than 70 mol %, more than 90 mol %, or more than 95 mol %. Accordingly, for example, the solution of the present invention may comprises an Exo and Endo forms of the adduct compound of formula (III-6) dissolved in a solvent, and the proportion of the Exo form based on the total of the Exo and Endo forms of the adduct compound above {Exo form/(Exo form+Endo form)} may be more than 50 mol %, more than 70 mol %, more than 90 mol %, more than 95 mol %, or more than 99 mol %.

In the case where the first adduct compound-containing solution contains a stereoisomer having a relatively low thermal elimination temperature in a relatively large ratio, at the time of eliminating the double bond-containing compound (II) from the solution and removing the double bond-containing compound (II) by heating to obtain an organic semiconductor film formed of the fused polycyclic aromatic compound of formula (I), the elimination can be started at a relatively low temperature. Accordingly, in this case, an organic semiconductor film can be produced at a relatively low temperature.

Incidentally, in the Diels-Alder reaction, a reaction product wherein a substituent is present on the side opposite to the main bridge is defined as an Endo form, and a reaction product wherein a substituent is present on the same side as the main bridge is defined as an Exo form.

<<Organic Semiconductor Film-Forming Solution—Crystallization Inhibitor—Second Adduct Compound>>

In one embodiment, the crystallization inhibitor contained in the solution of the present invention is a second adduct compound having a structure wherein a second double bond-containing compound (II") is added in an eliminatable state to the fused polycyclic aromatic compound of formula (I) through the double bond.

The second adduct compound has the same fused polycyclic aromatic compound of formula (I) as the first adduct compound. That is, the second adduct compound is the same as the first adduct compound except that a second double bond-containing compound (II") is added in place of the first double bond-containing compound (II').

Accordingly, the moiety of the fused polycyclic aromatic compound of formula (I) in the second adduct compound has relatively large affinity to the first adduct compound, and particularly to the moiety of the fused polycyclic aromatic compound of formula (I) in the first adduct compound. However, the first adduct compound and the second adduct compound differ from each other in structure due to the difference in the first and second double bond-containing compounds (II') and (II"), and therefore relatively do not tend to crystallize at the time of forming an organic semiconductor film by the solution method.

Also, the first and second adduct compounds have a structure wherein the first and second double bond-containing compound (I') and (II'), respectively, are added in an eliminatable state to the fused polycyclic aromatic compound of formula (I) through the double bond. Accordingly, when the first and second double bond-containing compound (II') and (II") are eliminated and removed, for example, by heating and/or depressurization, both the first and second adduct compounds give the fused polycyclic aromatic compound of formula (I).

Therefore, for example, when the concentration of the first adduct compound contained in the solution is constant, the content of the fused polycyclic aromatic compound of formula (I) in the solution can be substantially increased by the solution's further containing the second adduct compound.

The organic semiconductor film-forming solution of the present invention can contain the second adduct compound as the crystallization inhibitor in any amount capable of being dissolved in the solution. For example, the molar ratio of the second adduct compound to the first adduct compound (second adduct compound/first adduct compound) may be 0.1 mol % or more, 1 mol % or more, 10 mol % or more, 30 mol % or more, or 50 mol % or more. The molar ratio of 100 mol % means that the molar number of the first adduct compound contained in the organic semiconductor film-forming solution is the same as the molar number of the second adduct compound contained in the solution.

<<Organic Semiconductor Film-Forming Solution—Crystallization Inhibitor—First and Second Compounds (II') and (II")>>

In another embodiment, the crystallization inhibitor contained in the solution of the present invention is a first double bond-containing compound (II'). The double first bond-containing compound (II') used as the crystallization inhibitor is the same as the first double bond-containing compound (II') constituting the first adduct compound by being added in an eliminatable state to the fused polycyclic aromatic compound of formula (I) through the double bond. Accordingly, the first double bond-containing compound (II') used as the crystallization inhibitor can be added in an eliminatable state to the fused polycyclic aromatic compound of formula (I) through the double bond.

In still another embodiment, the crystallization inhibitor is a second double bond-containing compound (II"), which is a compound (II") capable of being added in an eliminatable state to the fused polycyclic aromatic compound of formula (I) through the double bond. That is, the second double bond-containing compound (II") used as the crystallization inhibitor differs from the first double bond-containing compound (II') constituting the first adduct compound by being added in an eliminatable state to the fused polycyclic aromatic compound of formula (I) through the double bond. However, the second double bond-containing compound (II") used as the crystallization inhibitor can be added in an eliminatable state to the fused polycyclic aromatic compound of formula (I) through the double bond, similarly to the first double bond-containing compound (II').

By the same mechanism as the eliminable addition of the double bond-containing first compound (II') to the fused polycyclic aromatic compound of formula (I) through the double bond to form a first adduct compound, both the first and second double bond-containing compounds (II') and (II") used as the crystallization inhibitor are added in an eliminatable state to the fused polycyclic aromatic compound of formula (I) and/or exhibit affinity to the fused polycyclic aromatic compound of formula (I), and thereby, at the formation of an organic semiconductor film by the solution method, the polarity of the first adduct compound can be more increased and/or the first adduct compound can be prevented from crystallization with each other.

In the organic semiconductor film-forming solution of the present invention, the first and second double bond-containing compounds (II') and (II") as the crystallization inhibitor may be contained in any amount capable of being dissolved in a solvent. The molar ratio of the first and second compounds (II') and (II") to the first adduct compound (first and/or second compounds (II') and (II")/first adduct compound) may be 0.1 mol % or more, 1 mol % or more, 10 mol % or more, 30 mol % or more, or 50 mol % or more. The molar ratio of 100 mol % means that the molar number of the first adduct compound contained in the organic semiconductor film-forming solution is the same as the molar number of the first and/or second compounds (II') and (II") contained in the solution are the same.

<<Production Method of Organic Semiconductor Film>>

The method of the present invention for producing an organic semiconductor film comprises coating the organic semiconductor film-forming solution of the present invention on a substrate to form a film, and eliminating the double bond-containing compound (II) from the first adduct compound and optionally from the second adduct compound and removing the double bond-containing compound (II) by depressurizing and/or heating the film to obtain an organic semiconductor film formed of the fused polycyclic aromatic compound of formula (I).

The coating of this solution on a substrate can be performed in any manner, and, for example, may be performed by a casting method, a spin coating method or a printing method. The coating of the solution on a substrate may be performed also by simply dropping the solution on a substrate.

In the case of eliminating and removing the compound (II) by heating and/or depressurization, any conditions causing substantially no decomposition of the fused polycyclic aromatic compound of formula (I) can be employed. Accordingly, the elimination and removal of the compound (II) can be performed, for example, by heating at a temperature of 80° C. or more, 100° C. or more, 120° C. or more, or 140° C. or more, and 200° C. or less, 220° C. or less, 240° C. or less, or 260° C. or less. Also, the elimination and removal of the compound (II) can be performed, for example, in a vacuum or under an atmospheric pressure. Furthermore, the elimination of the compound (II) can be performed, for example, in a nitrogen atmosphere or an air atmosphere. In particular, the elimination of the compound (II) is preferably performed in an air atmosphere under an atmospheric pressure in order to facilitate the production of the fused polycyclic aromatic compound of formula (I).

<<Production Method of Organic Semiconductor Device>>

The method of the present invention for producing an organic semiconductor device comprises producing an organic semiconductor film by the method of the present invention for producing an organic semiconductor film. This method may optionally further comprise forming an electrode layer and/or a dielectric layer above or below the organic semiconductor film.

<<Organic Semiconductor Device>>

The organic semiconductor device of the present invention is an organic semiconductor device having an organic semiconductor film, wherein the organic semiconductor film is formed of an organic semiconductor compound having the following formula (I) and at the same time, the organic semiconductor film contains a first adduct compound having a structure wherein a first double bond-containing compound (II') is added in an eliminatable state to a fused polycyclic aromatic compound of the following formula (I) through said double bond, and at least one compound selected from the group consisting of the following (a) to (c):

$$Ar_1Ar_2Ar_3 \tag{I}$$

(wherein each of $Ar_1$ and $Ar_3$ is independently selected from the group consisting of substituted or unsubstituted fused aromatic ring moieties each formed of 2 to 5 aromatic rings fused together, $Ar_2$ is selected from the group consisting of substituted or unsubstituted aromatic ring moieties each formed of one aromatic ring, and substituted or unsubstituted fused aromatic ring moieties each formed of 2 to 5 aromatic rings fused together, $Ar_1$ and $Ar_2$ form a fused aromatic ring by sharing at least two carbon atoms, and $Ar_2$ and $Ar_3$ form a fused aromatic ring by sharing at least two carbon atoms);

(a) a second adduct compound having a structure wherein a second double bond-containing compound (II") is added in an eliminatable state to the fused polycyclic aromatic compound of formula (I) through the double bond, (b) the first double bond-containing compound (II') capable of being added in an eliminatable state to the fused polycyclic aromatic compound of formula (I) through the double bond, and (c) the second double bond-containing compound (II") capable of being added in an eliminatable state to the fused polycyclic aromatic compound of formula (I) through the double bond.

The expression that the "organic semiconductor film contains the first adduct compound and at least one compound selected from the group consisting of (a) to (c) means that the organic semiconductor film contains these compounds in a detectable amount. Accordingly, for example, the molar ratio of these compounds to the organic semiconductor compound having formula (I) may be more than 1 ppm, more than 10 ppm, more than 100 ppm, more than 1,000 ppm, or more than 10,000 ppm (1%). Also, the proportion of these compounds based on the organic semiconductor compound having formula (I) may be 10 mol % or less, 5 mol % or less, 3 mol % or less, 1 mol % or less, 0.1 mol % or less, or 0.01 mol % or less.

Such an organic semiconductor device of the present invention can have characteristics as an organic semiconductor device, despite containing the first adduct compound and at least one compound selected from the group consisting of (a) to (c), as well as the fused polycyclic aromatic compound of formula (I). That is, in the case of producing an organic semiconductor film of the organic semiconductor device of the present invention from the organic semiconductor film-forming solution of the present invention, even when the thermal elimination reaction of the adduct compound and removal of the crystallization inhibitor do not proceed completely, the organic semiconductor device of the present invention can have characteristics as a semiconductor device. This is preferred to facilitate the production of the organic semiconductor device of the present invention or an organic semiconductor film thereof.

In particular, the organic semiconductor device of the present invention is a thin-film transistor having a source electrode, a drain electrode, a gate electrode, a gate insulating film and the organic semiconductor film. The thin-film transistor insulates the source electrode and the drain electrode from the gate electrode by the gate insulating film, and controls the current flowing through the organic semiconductor from the source electrode to the drain electrode by the voltage applied to the gate electrode. Also, particularly, the organic semiconductor device of the present invention is a solar cell having the organic semiconductor film as the active layer.

<<Others>>

As for the addition product, the fused polycyclic aromatic compound of formula (I), the double bond-containing compound (II) and the like, the descriptions related to the first present invention can be referred to.

<<<<Fourth Present Invention>>>>

<<α-Diketone Compound>>

The α-diketone compound of the present invention has the following formula (I(a)-X):

$$Ar_{1X}Ar_{2(a)}Ar_{3X} \qquad (I(a)\text{-}X)$$

(wherein each of $Ar_{1X}$ and $Ar_{3X}$ is independently selected from the group consisting of substituted or unsubstituted fused aromatic ring moieties each formed of 2 to 5 aromatic rings fused together, and at least one of the aromatic rings is substituted by a bicyclo α-diketone moiety of the following formula (X):

[Chem. 31]

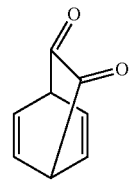

(X)

$Ar_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5 heteroaromatic rings fused together, $Ar_{1X}$ and $Ar_{2(a)}$ form a fused ring by sharing at least two carbon atoms, and $Ar_{2(a)}$ and $Ar_{3X}$ form a fused ring by sharing at least two carbon atoms}.

Regarding the α-ketone compound of the present invention, each of $Ar_{1X}$ and $Ar_{3X}$ is independently selected from the group consisting of substituted or unsubstituted fused aromatic ring moieties each formed of 2 to 5 aromatic rings fused together, particularly 2 to 4 aromatic ring fused together, and at least one of the aromatic rings is substituted by a bicyclo α-diketone moiety of the following formula (X):

[Chem. 32]

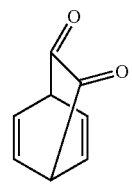

(X)

Also, for example, each of $Ar_{1X}$ and $Ar_{3X}$ is independently selected from the group consisting of fused benzene ring moieties each formed of 2 to 5 substituted or unsubstituted benzene rings fused together, particularly 2 to 4 substituted or unsubstituted benzene rings fused together, and at least one of the benzene rings is substituted by the bicyclo α-diketone moiety above. Incidentally, $Ar_{1X}$ and $Ar_{3X}$ may be the same or different.

Accordingly, each of $Ar_{1X}$ and $Ar_{3X}$ is independently selected from the group consisting of substituted or unsubstituted fused benzene ring moieties of the following (b1) to (b4), and at least one of the benzene rings is substituted with the bicyclo α-diketone moiety above.

[Chem. 33]

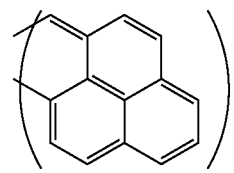

(b1)

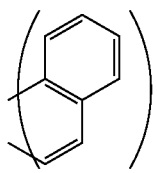
(b2)

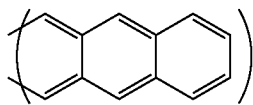
(b3)

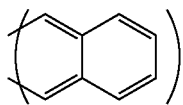
(b4)

Regarding the α-diketone compound of the present invention, $Ar_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5, particularly 2 to 3, heteroaromatic rings fused together. The heteroaromatic ring may be, for example, a heteroaromatic ring having the following structure:

[Chem. 34]

(wherein each Y is an element selected from the group consisting of chalcogens, particularly an element selected from the group consisting of oxygen (O), sulfur (S), selenium (Se) and tellurium (Te), more particularly sulfur).

Accordingly, $Ar_{2(a)}$ may be a substituted or unsubstituted fused heteroaromatic ring moiety selected from the group consisting of the following (a1), (a3) and (a4):

[Chem. 35]

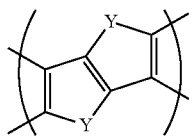
(a1)

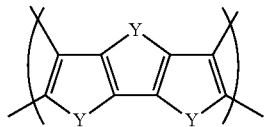
(a3)

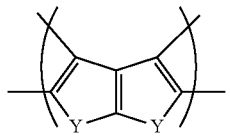
(a4)

(wherein Y is each independently an element selected from the group consisting of chalcogens, and may be all the same or may be partially different).

In the α-diketone compound of the present invention, the bicyclo α-diketone moiety is decomposed into a benzene ring moiety by light irradiation, and a fused polycyclic aromatic compound of the following formula (I(a)) is thereby produced:

$$Ar_1Ar_{2(a)}Ar_3 \qquad (I(a))$$

(wherein each of $Ar_1$ and $Ar_3$ is independently selected from the group consisting of substituted or unsubstituted fused aromatic ring moieties each formed of 2 to 5 aromatic rings fused together, $Ar_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5 heteroaromatic rings fused together, $Ar_1$ and $Ar_{2(a)}$ form a fused ring by sharing at least two carbon atoms, and $Ar_{2(a)}$ and $Ar_3$ form a fused ring by sharing at least two carbon atoms).

Regarding the fused polycyclic aromatic compound of formula (I(a)), each of $Ar_1$ and $Ar_3$ is independently selected from the group consisting of substituted or unsubstituted fused aromatic ring moieties each formed of 2 to 5 aromatic rings fused together, particularly 2 to 4 aromatic rings fused together. The aromatic ring is particularly a substituted or unsubstituted benzene ring. Also, $Ar_1$ and $Ar_3$ may be the same or different.

Accordingly, each of $Ar_1$ and $Ar_3$ may be independently a substituted or unsubstituted benzene ring moiety selected from the group consisting of (b1) to (b4).

Regarding the fused polycyclic aromatic compound of formula (I(a)), $Ar_{2(a)}$ is a substituted or unsubstituted heteroaromatic ring moiety formed of one heteroaromatic ring, or a substituted or unsubstituted fused heteroaromatic ring moiety formed of 2 to 5, and particularly 2 to 3, heteroaromatic rings fused together.

Accordingly, $Ar_{2(a)}$ may be a substituted or unsubstituted heteroaromatic ring moiety or fused heteroaromatic ring moiety selected from the group consisting of (a1), (a3) and (a4).

The fused polycyclic aromatic compound of formula (I(a)) is preferably an organic semiconductor compound, that is, an organic compound exhibiting properties as a semiconductor. Also, the fused polycyclic aromatic compound of formula (I(a)) can be selected from the group consisting of substituted or unsubstituted fused polycyclic aromatic compounds of the following formulae (I-1) to (I-5). These fused polycyclic aromatic compounds have high stability, and therefore at the production of the fused polycyclic aromatic compound of formula (I(a)) from the α-diketone compound of the present invention, the fused polycyclic aromatic compound of formula (I(a)) can be stably maintained. That is, in this case, even when heating is performed at the production of the fused polycyclic aromatic compound of formula (I(a)), the fused polycyclic aromatic compound of formula (I(a)) can be stably maintained. Accordingly, in this case, production of the fused polycyclic aromatic compound of formula (I(a)) from the α-diketone compound of the present invention can be performed at a high rate.

[Chem. 36]

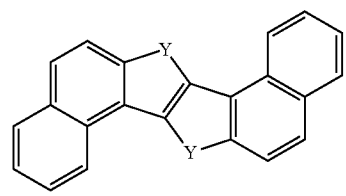
(I-1)

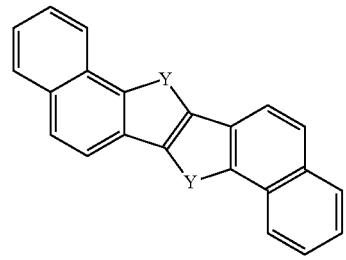
(I-2)

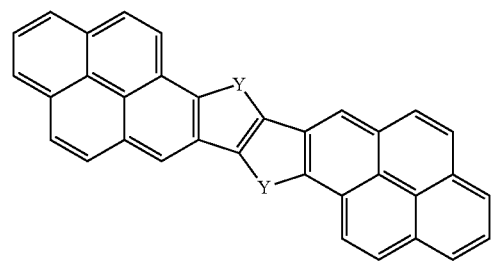
(I-3)

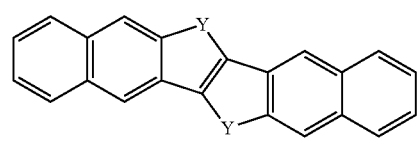
(I-4)

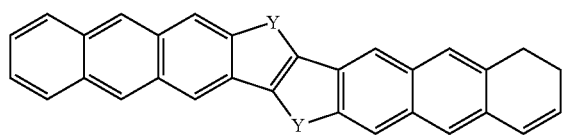
(I-5)

(wherein each Y is independently an element selected from the group consisting of chalcogens).

The fused polycyclic aromatic compound of formula (I(a)) and its synthesis are not particularly limited, but Patent Documents 1 to 5 and Non-Patent Document 1 may be referred to.

Specifically, the α-diketone compound of the present invention is, for example, a compound of the following formulae (I(a)-X1) to (I(a)-X5), or a stereoisomer thereof:

[Chem. 37]

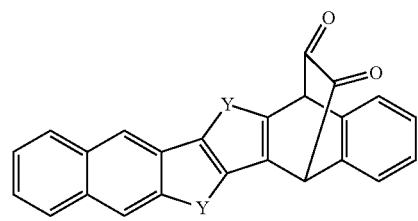
(I(a)-X1)

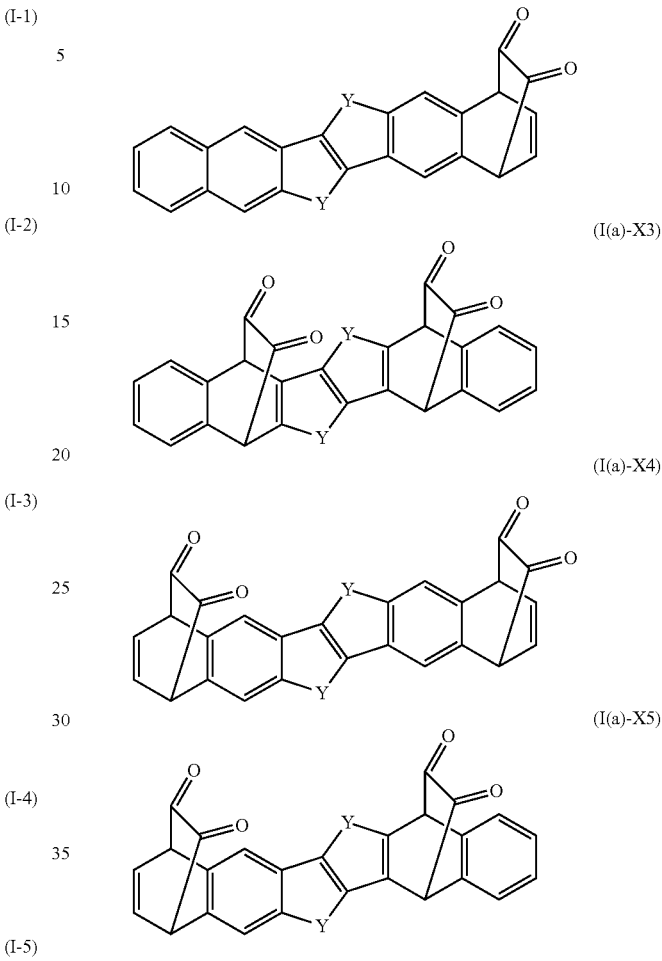
(I(a)-X2)
(I(a)-X3)
(I(a)-X4)
(I(a)-X5)

(wherein each Y is independently an element selected from the group consisting of chalcogens, and the fused benzene ring moiety is substituted or unsubstituted).

In these compounds of formulae (I(a)-X1) to (I(a)-X5) or stereoisomers thereof, the bicyclo α-diketone moiety is decomposed into a benzene ring moiety by light irradiation, and thereby a compound of the following formula (I-4) as an example of the fused polycyclic aromatic compound can be produced.

[Chem. 38]

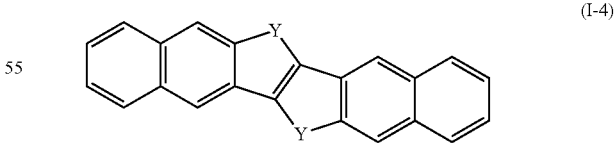
(I-4)

(wherein each Y is independently an element selected from the group consisting of chalcogens, and the fused benzene ring moiety is substituted or unsubstituted).

Incidentally, the aromatic ring or the like is substituted, for example, by a substituent selected from the group consisting of halogens, alkyl groups having from 1 to 20 carbon atoms, alkenyl groups having from 2 to 20 carbon atoms, alkynyl groups having from 2 to 20 carbon atoms, substituted or unsubstituted aromatic groups having from 4 to 20 carbon atoms, ester groups having from 2 to 10 carbon atoms, ether groups having from 1 to 20 carbon atoms, ketone groups having from 1 to 20 carbon atoms, amino groups having from 1 to 20 carbon atoms, amide groups having from 1 to 20 carbon atoms, imide groups having from 1 to 20 carbon atoms, and sulfide groups having from 1 to 20 carbon atoms.

<<First Synthesis Method of α-Diketone Compound>>

The α-diketone compound of the present invention can be synthesized by a method including the following steps (a) to (c):

(a) providing a vinylene carbonate-added fused polycyclic aromatic compound having a structure wherein vinylene carbonate is added in an eliminatable state to a fused polycyclic aromatic compound of the following formula (I(a)) through the double bond:

$$Ar_1Ar_{2(a)}Ar_3 \qquad (I(a))$$

(wherein each of $Ar_1$ and $Ar_3$ is independently selected from the group consisting of substituted or unsubstituted fused aromatic ring moieties each formed of 2 to 5 aromatic rings fused together, $Ar_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5 heteroaromatic rings fused together, $Ar_1$ and $Ar_{2(a)}$ form a fused ring by sharing at least two carbon atoms, and $Ar_{2(a)}$ and $Ar_3$ form a fused ring by sharing at least two carbon atoms);

(b) hydrolyzing the vinylene carbonate-added fused polycyclic aromatic compound to obtain an α-diol compound having a structure wherein the portion corresponding to the vinylene carbonate is converted into an α-diol moiety, (c) oxidizing the α-diol compound to convert the α-diol moiety into an α-diketone moiety.

The vinylene carbonate-added fused polycyclic aromatic compound used as a raw material in the step (a) of this method can be produced by a method comprising adding vinylene carbonate to the fused polycyclic aromatic compound of formula (I(a)), particularly adding these compounds by mixing these compounds together. At this time, vinylene carbonate may be used by dissolving it in a solvent, but may be also used by itself. As the solvent, any solvent capable of dissolving vinylene carbonate can be used. For example, the usable solvent includes an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (that is, 1,3,5-trimethylbenzene); aliphatic hydrocarbons such as hexane and heptane; and a halogen-containing solvent such as dichloromethane, chloroform and dichloroethane.

In the synthesis of the vinylene carbonate-added fused polycyclic aromatic compound, the reaction may be accelerated by heating and/or light irradiation when mixing the fused polycyclic aromatic compound of formula (I(a)) and vinylene carbonate. The reaction temperature at the synthesis of the vinylene carbonate-added fused polycyclic aromatic compound may be determined by taking into consideration the production rate, the stability of components, the boiling point of components, and the like, and the temperature may be 20° C. or more, 50° C. or more, or 100° C. or more, and 180° C. or less, 200° C. or less, or 220° C. or less. Also, the reaction time may be, for example, 1 minute or more, 10 minutes or more, 30 minutes or more, or 1 hour or more, and 1 day or less, 3 days or less, 5 days or less, or 10 days or less.

For example, dinaphthothienothiophene (DNTT) as the fused polycyclic aromatic compound, and vinylene carbonate are mixed in a mesitylene solvent, and while stirring under heating in nitrogen, vinylene carbonate is added to DNTT by the Diels-Alder addition reaction to obtain a vinylene carbonate-added dinaphthothienothiophene (compound of the following formula (1)) as the vinylene carbonate-added fused polycyclic aromatic compound. Thereafter, the vinylene carbonate-added dinaphthothienothiophene is obtained as a solid matter by filtration, and washed with chloroform.

[Chem. 39]

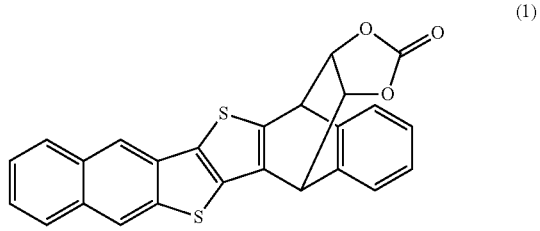

(1)

For the hydrolysis in the step (b) of this method, for example, the vinylene carbonate-added dinaphthothienothiophene (compound of formula (I)) provided in the step (b) is charged into ethanol, and after further adding sodium hydroxide, reflux is performed to obtain an α-diol compound (compound of the following formula (2)) wherein the portion corresponding to vinylene carbonate is converted into an α-diol moiety. Incidentally, as for the hydrolysis reaction of the step (b), Non-Patent Document 4 may be referred to.

[Chem. 40]

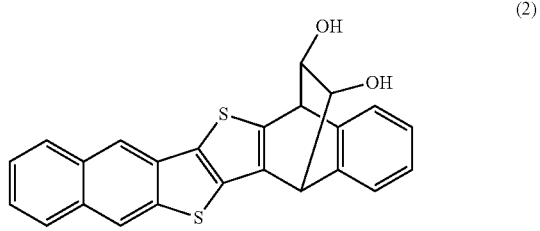

(2)

For the oxidation in the step (c) of this method, for example, the α-diol compound obtained in the step (b) is reacted in a mixed solution of dimethylsulfoxide, trifluoroacetic anhydride, triethylamine and methylene chloride while cooling to oxidize the α-diol compound and convert the α-diol moiety into an α-diketone moiety, and thereby an α-diketone compound (compound of the following formula (3)) is obtained. Incidentally, as for the oxidation reaction of the step (c), Non-Patent Document 4 may be referred to.

[Chem. 41]

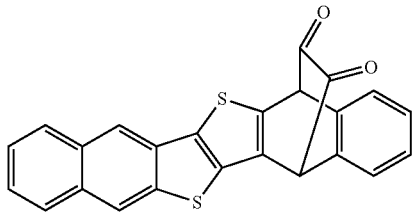
(3)

In another embodiment of this method, for providing vinylene carbonate-added dinaphthothienothiophene as an example of the vinylene carbonate-added fused polycyclic aromatic compound used as a raw material in the step (a), 2-methylthio-3-naphthoaldehyde obtained as indicated in Patent Document 5 is charged into a tetrahydrofuran solvent in a nitrogen stream and after adding vinylene carbonate thereto, the reaction is allowed to proceed at a reflux temperature to obtain an adduct (compound of the following formula (4) or (5)) wherein vinylene carbonate is added to 2-methylthio-3-naphthoaldehyde. This adduct is subjected to the procedure indicated in Example 1 of Patent Document 5 to combine two molecules of the adduct, and thereby obtain vinylene carbonate-added dinaphthothienothiophene.

[Chem. 42]

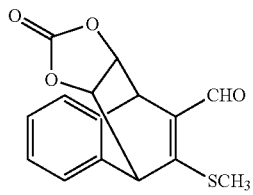
(4)

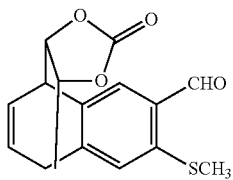
(5)

<<Intermediate α-Diketone Compound and Second Synthesis Method of α-Diketone Compound>>

The intermediate α-diketone compound of the present invention has the following formula (I(a)'):

Ar$_{1X}$Q  (I(a)')

{wherein Ar$_{1X}$ is selected from the group consisting of substituted or unsubstituted fused aromatic ring moieties each formed of 2 to 5 aromatic rings fused together, and at least one of the aromatic rings is substituted by a bicyclo α-diketone moiety of the following formula (X):

[Chem. 43]

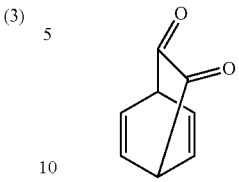
(X)

and

Q has the following formula and constitutes a part of the fused ring of Ar$_{1X}$:

[Chem. 44]

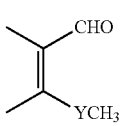

(wherein Y is an element selected from the group consisting of chalcogens)}.

For example, the compound of formula (I(a)') may be either one of the following formulae, or a stereoisomer thereof:

[Chem. 45]

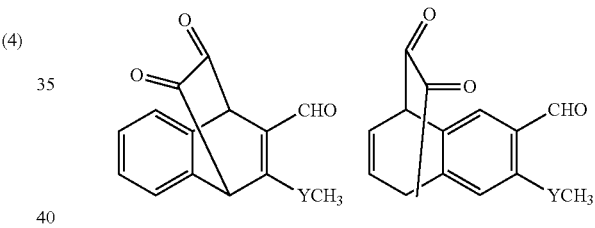

(wherein Y is an element selected from the group consisting of chalcogens, and the benzene ring moiety is substituted or unsubstituted).

The intermediate α-diketone compound of the present invention can be obtained by adding vinylene carbonate to a compound of the following formula (I'), and hydrolyzing and oxidizing the obtained compound:

Ar$_1$Q  (I')

{wherein Ar$_1$ is selected from the group consisting of substituted or unsubstituted fused aromatic ring moieties each formed of 2 to 5 aromatic rings fused together, and Q has the following formula and constitutes a part of the fused aromatic ring of Ar$_1$:

[Chem. 46]

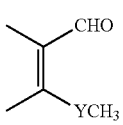

(wherein Y is an element selected from the group consisting of chalcogens)}.

As for the addition reaction, hydrolysis reaction and oxidation reaction to obtain the intermediate α-diketone compound, the descriptions related to the first synthesis method of the α-diketone compound may be referred to.

Specifically, for obtaining the intermediate α-diketone compound of the present invention, an adduct (compound of the above formula (4) or (5)) wherein vinylene carbonate is added to 2-methylthio-3-naphthoaldehyde is charged into ethanol, and after further adding sodium hydroxide, reflux is performed to obtain an α-diol compound (compound of the following formula (6) or (7)) wherein the portion corresponding to vinylene carbonate is converted into an α-diol moiety. Incidentally, as for this hydrolysis reaction, Non-Patent Document 4 may be referred to.

[Chem. 47]

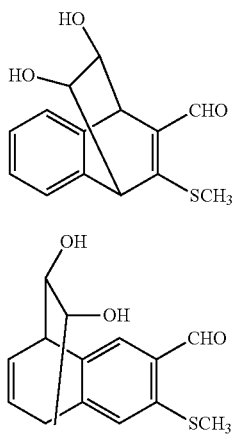

Thereafter, the α-diol compound (compound of the above formula (6) or (7)) is reacted in a mixed solution of dimethylsulfoxide, trifluoroacetic anhydride, triethylamine and methylene chloride while cooling to oxidize the α-diol compound and convert the α-diol moiety into an α-diketone moiety, and thereby the intermediate α-diketone compound (compound of the following formula (8) or (9)) is obtained. Incidentally, as for this oxidation reaction, Non-Patent Document 4 may be referred to.

[Chem. 48]

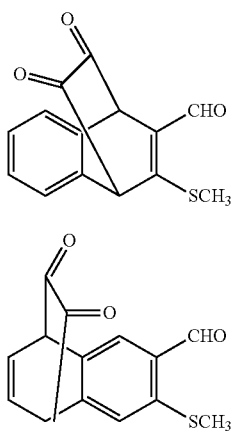

The method for synthesizing the α-diketone compound of the present invention from the intermediate α-diketone compound includes the following steps (a) and (b):

(a) reacting two molecules of the intermediate α-diketone compound of the present invention, or reacting one molecule of the intermediate α-diketone compound of the present invention and one molecule of a compound having a structure wherein the bicyclo α-diketone moiety of the intermediate α-diketone compound of the present invention is decomposed into a benzene ring moiety, to obtain a compound of the following formula:

$Ar_{1X}Q=QAr_{1X}$ 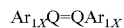

{wherein Q=Q represents the following structure:

[Chem. 49]

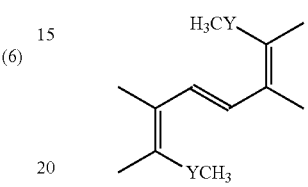

(wherein Y is an element selected from the group consisting of chalcogens)}; and (b) reacting the obtained compound of $Ar_{1X}Q=QAr_{1X}$ with iodine.

According to this method, the α-diketone compound of the following formula (I(a1)-X) of the present invention is synthesized:

$Ar_{1X}Ar_{2(a1)}Ar_{1X}$     (I(a1)-X) 

(wherein $Ar_{1X}$ is selected from the group consisting of substituted or unsubstituted fused aromatic ring moieties each formed of 2 to 5 aromatic rings fused together, and at least one of the aromatic rings is substituted by a bicyclo α-diketone moiety of the following formula (X):

[Chem. 50]

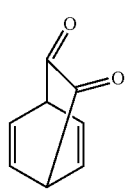

$Ar_{2(a1)}$ is a fused heteroaromatic ring moiety of the following formula (a1) (Y is an element selected from the group consisting of chalcogens),

[Chem. 51]

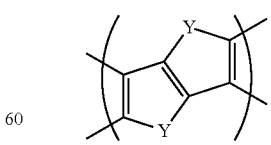

and $Ar_{1X}$ and $Ar_{2(a1)}$ form a fused ring by sharing at least two carbon atoms).

As for the conditions and the like of the method for synthesizing the α-diketone compound of the present invention from the intermediate α-diketone compound above, the descriptions in Non-Patent Document 1 can be referred to. That is, for example, the reaction of two molecules of the intermediate α-diketone compound in the step (a) is performed in tetrahydrofuran by using a tetrachlorotitanium/zinc (TiCl$_4$/Zn) catalyst. Also, the reaction of Ar$_{1X}$(Q=Q)Ar$_{1X}$ and iodine in the step (b) is performed in trichloromethane (i.e., chloroform) (CHCl$_3$).

Also, in this method, for example, the intermediate α-diketone compound (compound of the above formula (8) or (9)) of the present invention is subjected to the procedure indicated in Example 1 of Patent Document 5 to combine two molecules of the adduct, and thereby obtain vinylene carbonate-added dinaphthothienothiophene (any one of the following formulae (3-1) to (3-5)).

[Chem. 52]

(3-1)
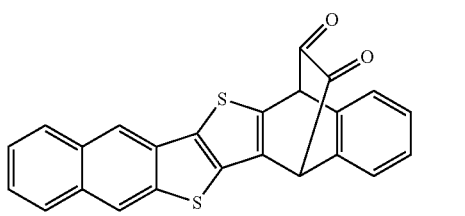

(3-2)
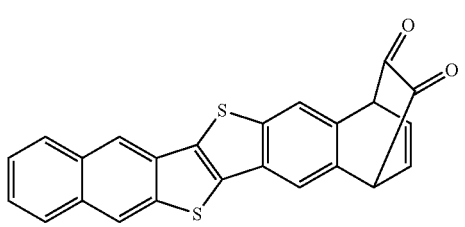

(3-3)
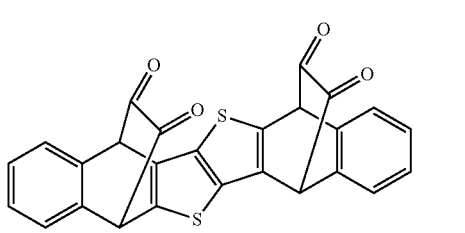

(3-4)
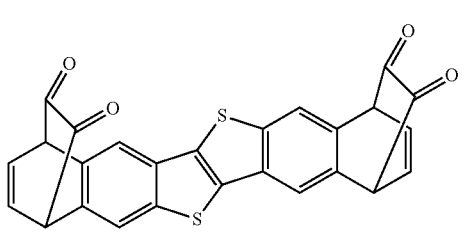

(3-5)
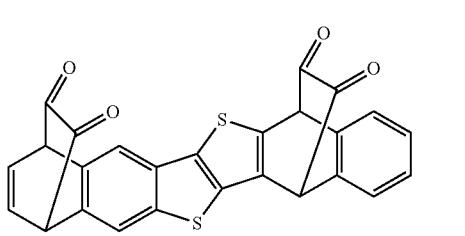

<<α-Diketone Compound-Containing Solution>>

The α-diketone compound-containing solution of the present invention comprises the α-diketone compound of the present invention dissolved in a solvent, particularly in an organic solvent.

The α-diketone compound-containing solution may contain the α-diketone compound of the present invention in any concentration, and, for example, may contain the α-diketone compound of the present invention in a concentration of 0.01 to 20 massa, from 0.05 to 10 mass %, or from 0.1 to 5 mass %.

The solvent which can be used in the α-diketone compound-containing solution includes any solvent capable of dissolving the α-diketone compound of the present invention. For example, the usable solvent includes an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane.

<<Production Method of Organic Semiconductor Film>>

The method of the present invention for producing an organic semiconductor film comprises the following steps (a) and (b):

(a) coating the α-diketone compound-containing solution of the present invention on a substrate to produce a film, and (b) irradiating the film with light to decompose the bicyclo α-diketone moiety of the α-diketone compound into a benzene ring moiety, and thereby an organic semiconductor film formed of a fused polycyclic aromatic compound of the following formula (I(a)) is obtained:

$$Ar_1Ar_{2(a)}Ar_3 \quad (I(a))$$

(wherein each of Ar$_1$ and Ar$_3$ is independently selected from the group consisting of substituted or unsubstituted fused aromatic ring moieties each formed of 2 to 5 aromatic rings fused together, Ar$_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5 heteroaromatic rings fused together, Ar$_1$ and Ar$_{2(a)}$ form a fused ring by sharing at least two carbon atoms, and Ar$_{2(a)}$ and Ar$_3$ form a fused ring by sharing at least two carbon atoms).

The coating of this solution on a substrate can be performed in any mode, and, for example, may be performed by a casting method, a spin coating method or a printing method. The coating of the solution on a substrate may be performed also by simply dropping the solution on a substrate.

In the irradiation with light to obtain the fused polycyclic aromatic compound of formula (I(a)) from the α-diketone compound, irradiation may be performed with light having any wavelength and/or intensity capable of achieving such decomposition. However, in general, the decomposition can be achieved using from visible light to light at an ultraviolet wavelength.

Incidentally, the method may further comprise performing depressurization and/or heating in combination with the light irradiation or after the light irradiation to remove impurities other than the fused polycyclic aromatic compound of formula (I(a)). In this case, any conditions causing substantially no decomposition of the fused polycyclic aromatic compound of formula (I(a)) can be employed. Accordingly, the heating can be performed, for example, at a temperature of 40° C. or more, 60° C. or more, 80° C. or more, 100° C. or more, 120° C. or more, or 140° C. or more, and 200° C. or less, 220° C. or less, 240° C. or less, or 260° C. or less. Also, the decomposition of the α-diketone compound of the present invention and/or the removal of impurities can be performed, for example, in a vacuum or under an atmospheric pressure. Furthermore, the decomposition of the α-diketone compound of the present invention and/or the removal of impurities can be performed, for example, in a nitrogen atmosphere or an air atmosphere. In particular, the decomposition of the α-diketone compound of the present invention and/or the removal of impurities are preferably performed in an air atmosphere under an atmospheric pressure in order to easily perform the process.

<<Production Method of Organic Semiconductor Device>>

The method of the present invention for producing an organic semiconductor device comprises producing an organic semiconductor film by the method of the present invention for producing an organic semiconductor film. This method may optionally further comprise forming an electrode layer and/or a dielectric layer above or below the organic semiconductor film.

<<Organic Semiconductor Device>>

The organic semiconductor device of the present invention is an organic semiconductor device having an organic semiconductor film. The organic semiconductor film is formed of a fused polycyclic aromatic compound of the following formula (I(a)), and the organic semiconductor film further contains the α-diketone compound of the present invention:

(wherein each of $Ar_1$ and $Ar_3$ is independently selected from the group consisting of substituted or unsubstituted fused aromatic ring moieties each formed of 2 to 5 aromatic rings fused together, $Ar_{2(a)}$ is selected from the group consisting of substituted or unsubstituted heteroaromatic ring moieties each formed of one heteroaromatic ring, and substituted or unsubstituted fused heteroaromatic ring moieties each formed of 2 to 5 heteroaromatic rings fused together, $Ar_1$ and $Ar_{2(a)}$ form a fused ring by sharing at least two carbon atoms, and $Ar_{2(a)}$ and $Ar_3$ form a fused ring by sharing at least two carbon atoms).

The expression that the organic semiconductor film contains the α-diketone compound of the present invention" means that the organic semiconductor film contains the α-diketone compound of the present invention in a detectable amount. Accordingly, for example, the molar ratio of the α-diketone compound of the present invention may be more than 1 ppm, more than 10 ppm, more than 100 ppm, more than 1,000 ppm, or more than 10,000 ppm (1%). Also, the proportion of the α-diketone compound of the present invention may be 10 mol % or less, 5 mol % or less, 3 mol % or less, 1 mol % or less, 0.1 mol % or less, or 0.01 mol % or less.

Such an organic semiconductor device of the present invention has characteristics as an organic semiconductor device, despite containing the α-diketone compound as well as the fused polycyclic aromatic compound of formula (I). That is, in the case of producing an organic semiconductor film of the organic semiconductor device of the present invention from the α-diketone compound of the present invention, even when the thermal elimination reaction of the α-diketone compound of the present invention does not proceed completely, the organic semiconductor device of the present invention has characteristics as a semiconductor device. This is preferred to facilitate the production of the organic semiconductor device of the present invention or an organic semiconductor film thereof.

In particular, the organic semiconductor device of the present invention is a thin-film transistor having a source electrode, a drain electrode, a gate electrode, a gate insulating film and the organic semiconductor film. The thin-film transistor insulates the source electrode and the drain electrode from the gate electrode by the gate insulating film, and controls the current flowing through the organic semiconductor from the source electrode to the drain electrode by the voltage applied to the gate electrode. Also, particularly, the organic semiconductor device of the present invention is a solar cell having the organic semiconductor film as the active layer.

EXAMPLES

In the following Examples and Comparative Examples, unless otherwise indicated, the structure of the target compound was determined as needed by 1H-NMR (1H-nuclear magnetic resonance spectrum), MS (mass spectrometry) and elemental analysis. The devices used are as follows.

$^1$H-NMR: JEOL ECA-500 (500 MHz)

MS: Shimazu QP-5050A

Elemental analysis: Parkin Elmer Model 2400CHN Elemental Analyzer

Also, the conditions in computer simulation performed for the addition reaction are as follows.

<Semi-Empirical Approach>

Program: MOPAC 3.0

Hamiltonian: AM1

Structure optimization: Structure optimization by EF process

<Non-Empirical Approach>

Program: Gaussian 03

Exchange-correlation function: B3LYP

Basis function system: 6-31G(d)

Structure optimization: Berny algorithm

In the computer simulation, the heat of formation of the raw material compounds and the heat of formation of the adduct compound of those compounds were determined, and based on the results, the feasibility for the reaction to produce the adduct compound was evaluated. When the value of difference (relative heat of formation) between the total heat of formation of raw material compounds and the heat of formation of the adduct compound of those compounds is more than −20 kcal/mol (endothermic), i.e., when the addition reaction is an exothermic reaction or a slightly endothermic reaction, the reaction to produce the adduct compound is considered to be feasible. Also, when the relative heat of formation is a relatively small value, for example, in the case of an endothermic reaction wherein the value of the relative heat of formation is more than −20 kcal/mol, or an exothermic reaction wherein the value is 20 kcal/mol or less, the addition reaction is considered to be reversible. Incidentally, when only carbon and hydrogen are taken into account of, reliability of MOPAC is very high, but when other elements are contained, Gaussian has high reliability.

Example 1-1A

After adding 20 g (47.66 mmol) of hexachlorocyclopentadiene (HCCPD, MW=272.77, the structural formula is shown below) to 100 mg (0.293 mmol) of dinaphthothienothiophene (DNTT, MW=340.46, the structural formula is shown below) synthesized by the method indicated in Patent Document 2, the reaction temperature was kept at 160° C. over 24 hours.

[Chem. 53]

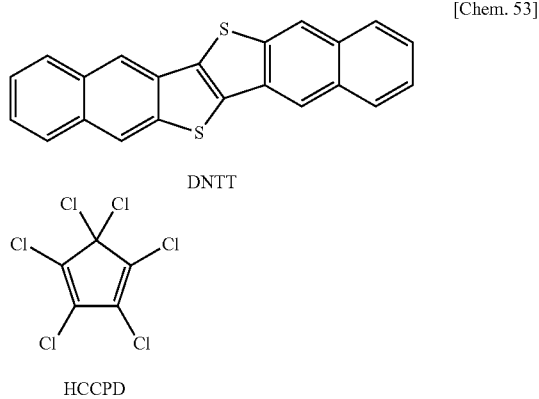

DNTT

HCCPD

Thereafter, the reaction product was allowed to cool, and thereby hexachlorocyclopentadiene 2-addition dinaphthothienothiophene (DNTT-2HCCPD(TTs), Mw: 886.00, 20 mg, 0.0225 mmol, yield=7.7%, the structural formula is shown below) was obtained.

[Chem. 54]

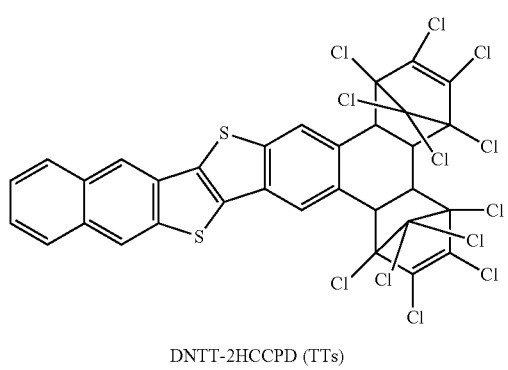

DNTT-2HCCPD (TTs)

The thus-obtained DNTT-2HCCPD(TTs) was purified by high-performance liquid chromatography (Agilent 1100 Series HPLC: High Performance Liquid Chromatography, SHISEIDO CAPCELL PAK C18 TYPE UG120, solvent: acetonitrile/water).

The analysis results of DNTT-2HCCPD(TTs) are shown below.

$^1$H-NMR (500 MHz, CDCl$_3$): δ 8.43 (s, 1H), 8.39 (s, 1H), 8.33 (s, 1H), 8.24 (s, 1H), 8.05 (m, 1H), 7.96 (m, 1H), 7.55 (m, 2H), 4.20 (d, J=9.5 Hz, 1H), 4.16 (d, J=9.5 Hz, 1H), 3.64 (d, J=8.9 Hz, 2H).

Anal. Calcd. for C$_{32}$H$_{12}$Cl$_{12}$S$_2$: C, 43.37; H, 1.37
Found: C, 41.9; H, 1.3
MS (70 eV, DI): 340 m/z The detected value (340 m/z) of the mass spectrometry (MS) coincides with DNTT (molecular weight: 340.46), revealing that when DNTT-2HCCPD(TTs) is exposed to the conditions of mass spectrometry (70 eV, DI), HCCPD is eliminated and DNTT is regenerated.

DNTT-2HCCPD(TTs) obtained in the synthesis above was dissolved in toluene to a concentration of 0.2 mass % to prepare a solution for the formation of a semiconductor device.

Next, an n-doped silicon wafer with an SiO$_2$ oxide film of 300 nm (surface resistance: 0.005 Ω·cm) was subjected to a UV ozone treatment over 20 minutes (Eye UV-Ozone Cleaning System OC-250615-D+A, Eye Graphics Co., Ltd.). Also, a toluene solution containing 10 mmol of octadecyltrichlorosilane (ODTS, LS-6495, Shin-Etsu Chemical Co., Ltd.) was prepared, and the silicon substrate subjected a UV ozone treatment was dipped in the solution for 24 hours. Thereafter, source/drain gold electrodes having a channel length of 50 μm and a channel width of 1.5 mm were produced on the silicon substrate by the vacuum deposition method (resistance heating-type vapor deposition apparatus: SVC-700 TM/700-2, Sanyu Electron Co., Ltd.).

While heating the silicon substrate at 40° C., the solution for the formation of a semiconductor device was dropped on the channel portion, and the solvent was vaporized to form a thin layer formed of DNTT-2HCCPD(TTs). The thus-produced device was heat-treated at 180° C. over 1 hour in a vacuum to produce an organic semiconductor device. FIG. 1 shows the outline of the obtained organic semiconductor device. In the organic semiconductor device shown in FIG. 1, a dielectric layer 5 of silicon oxide is formed on a substrate (gate electrode) 7 of the silicon wafer, and source and drain electrodes 2 and 3 and then an organic semiconductor 1 are stacked on the dielectric layer 5.

Figure 2:
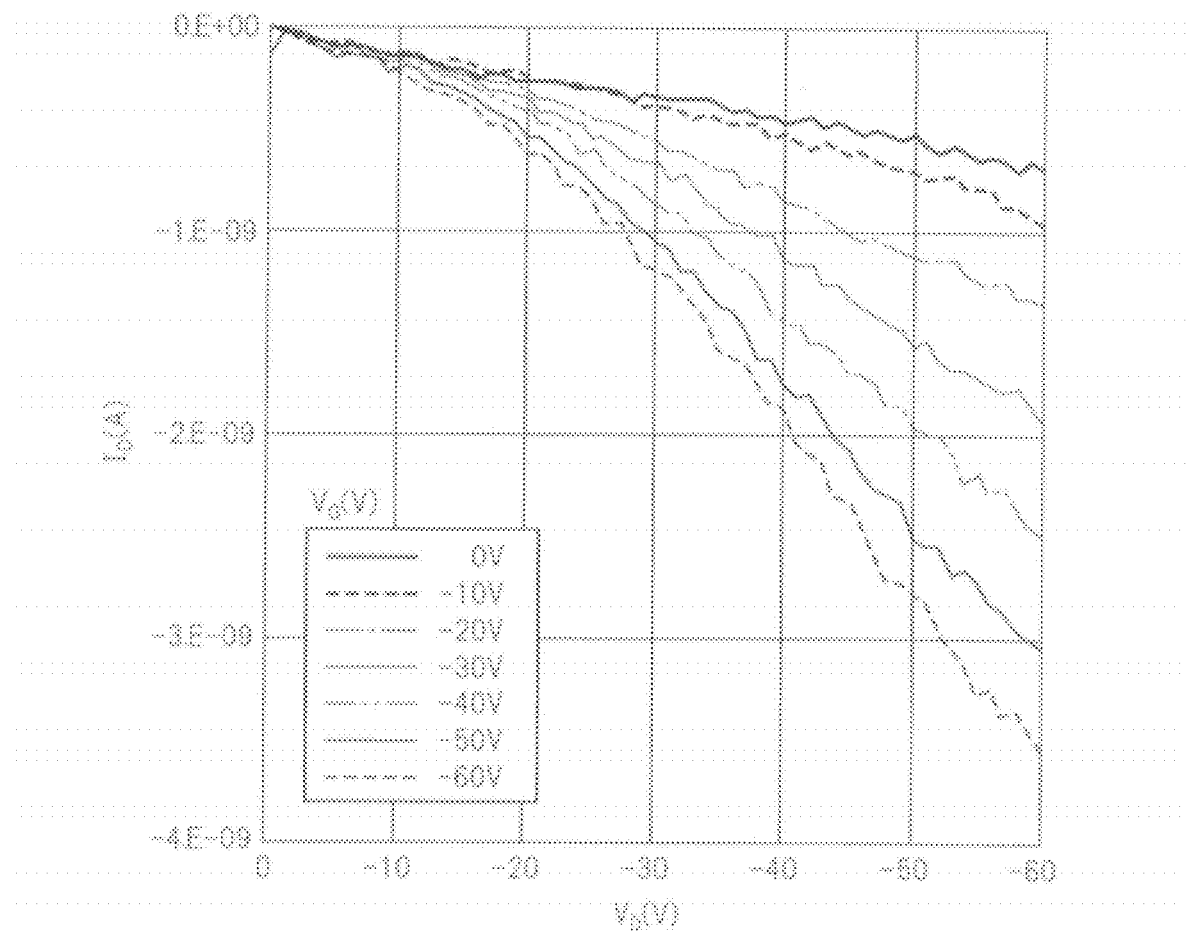
FIG. 2 is a view showing the output characteristics of the field effect transistor obtained in Example 1-1A.
Figure 3:
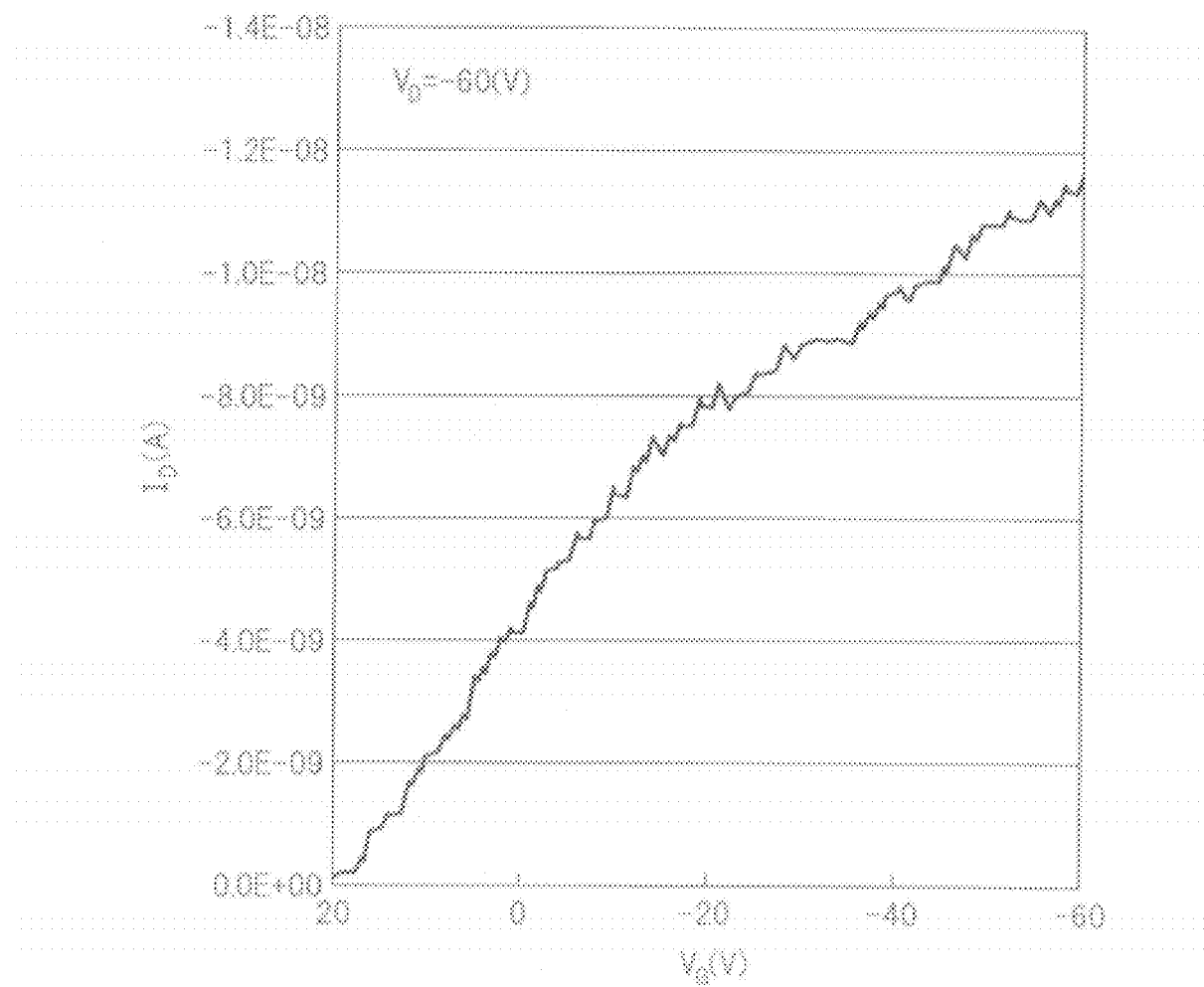
FIG. 3 is a view showing the transmission characteristics of the field effect transistor obtained in Example 1-1A.

The organic semiconductor was evaluated for the characteristics, and found to exhibit p-type semiconductor characteristics. The carrier mobility was 2×10$^{-5}$ cm$^2$/Vs, the on/off ratio was 113, and the threshold voltage was 14.4 V. FIGS. 2 and 3 show the output characteristics and the transmission characteristics, respectively, as a field effect transistor (FET). In FIG. 2, the vertical axis indicates the drain current (I$_D$(A)), and the horizontal axis indicates the drain voltage (V$_D$(V)). Also, in FIG. 3, the vertical axis indicates the drain current (I$_D$(A)), and the horizontal axis indicates the gate voltage (V$_G$(V)).

Comparative Example 1-1A

DNTT alone with no addition of HCCPD was added in toluene to a concentration of 0.2 mass %, but did not easily dissolve. Accordingly, DNTT alone could not be used in the solution method.

Example 1-1B

The addition reaction of dinaphthothienothiophene (DNTT) and hexachlorocyclopentadiene (HCCPD) was confirmed by computer simulation using the above-described semi-empirical approach (MOPAC).

The results are shown in the Table below. In the semi-empirical approach (MOPAC), the heat of formation of DNTT was set to 117.29 kcal/mol, and the heat of formation of HCCPD was set to 5.86 kcal/mol.

TABLE 1

| | State of Addition | | Relative Heat of Formation (kcal/mol) | MOPAC | | |
|---|---|---|---|---|---|---|
| | | | | Heat of Formation Relative to DNTT-1HCCPD(T) and DNTT-1HCCPD(Tb) | Heat of Formation Relative to DNTT-2HCCPD(TTs) | Heat of Formation Relative to DNTT-3HCCPD(TTTb) |
| | Number of Additions | Position of Addition | | | | |
| DNTT-1HCCPD(C) | 1 | c | −18.26 | — | — | — |
| DNTT-1HCCPD(T) | 1 | z | −7.67 | — | — | — |
| DNTT-1HCCPD(Tb) | 1 | e | −7.69 | — | — | — |
| DNTT-2HCCPD(TTs) | 2 | iso-anti | −10.92 | −3.24 | — | — |
| DNTT-2HCCPD(CT) | 2 | anti-cz | −28.07 | −20.39 | — | — |
| DNTT-2HCCPD(CTb) | 2 | anti-ce | −28.12 | −20.44 | — | — |
| DNTT-2HCCPD(TT) | 2 | anti-zz | −15.52 | −7.85 | — | — |
| DNTT-2HCCPD(TTb) | 2 | anti-ee | −15.51 | −7.84 | — | — |
| DNTT-2HCCPD(TTz) | 2 | anti-ze | −15.48 | −7.81 | — | — |
| DNTT-3HCCPD(CTT) | 3 | anti-zzc | −37.92 | — | −27.01 | — |
| DNTT-3HCCPD(TTT) | 3 | iso-anti-zze | −18.76 | — | −7.85 | — |
| DNTT-3HCCPD(TTTb) | 3 | iso-anti-eez | −18.73 | — | −7.81 | — |
| DNTT-4HCCPD(TTTT) | 4 | iso-anti | −21.98 | — | — | −3.25 |

As for the position of addition in Table 1 indicating the position at which HCCPD is added to DNTT, as shown in the following chemical formula, "c" indicates the center position, "z" indicates the terminal position on the same side (zusammen) as the adjacent sulfur (S) atom, and "e" indicates the terminal position on the opposite side (entgegen) to the adjacent sulfur (S) atom.

[Chem. 55]

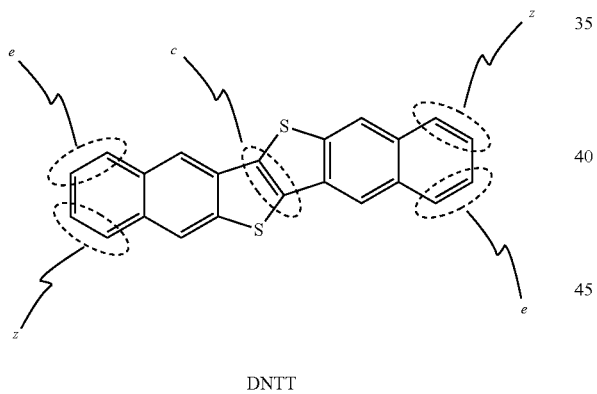

DNTT

Also, in Table 1, "anti" indicates that HCCPDS are added from the opposite sides to each other with respect to the conjugate plane of DNTT, and "iso" indicates that two HCCPD are added to the terminals on the same side of DNTT. Furthermore, when three or more HCCPD are added, "anti" indicates that the bond conformation is "anti" between HCCPD at adjacent opposite terminals.

It is understood from the results in Table 1 that when only one HCCPD is added to DNTT, HCCPD is added to DNTT at the terminal position on the same side as the adjacent sulfur (S) atom (position of addition: "z", code: "DNTT-1HCCPD (T)"), or at the terminal position on the opposite side to the adjacent sulfur (S) atom (position of addition: "e", code: "DNTT-1HCCPD(Tb)"). Also, it is understood that when another HCCPD is further added to the adduct compound above, HCCPD is further added to the same terminal (position of addition: "iso") as the terminal to which HCCPD is already added (code: "DNTT-2HCCPD(TTs)".

The result that, when two HCCPD are added to DNTT, HCCPD is further added to the same terminal (position of addition: "iso") as the terminal to which HCCPD is already added corresponds to the result obtained in Example 1-1A. Accordingly, application of computer simulation in the Diels-Alder reaction is understood to be proper.

Example 1-2A 1,750 mg (5.14 mmol) of dinaphthothienothiophene (DNTT, MW=340.46), 17.83 g (169.62 mmol, 3,300 mol %) of N-sulfonylacetamide (NSAA, MW: 105.12, the structural formula is shown below), and 12.81 mg (0.05 mmol) of metal catalyst reagent $CH_3ReO_3$ (ACROS A0245387, MW: 249.23) were mixed in a chloroform solvent, and the mixture was refluxed at 63° C. over 15.5 hours in nitrogen, and thereby the Diels-Alder addition reaction of DNTT and NSAA was performed.

[Chem. 56]

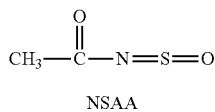

NSAA

Thereafter, the solid matter was collected by filtration and washed with chloroform. The obtained green solid (1.82 g) was confirmed to be impurities containing raw materials.

Hexane was added to the filtrate to effect recrystallization, and 0.2636 g of a yellow solid matter (31.5 mg) was obtained by filtration. This solid matter was separated by HPLC to obtain 31.5 mg of an adduct compound (DNTT-1NSAA, Mw=445.58, yield: 1.4 mol %) wherein one molecule of NSAA is added to DNTT. The structural formula of this adduct compound is shown below.

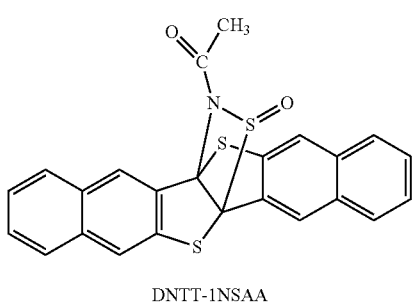

DNTT-1NSAA

The analysis results of the obtained DNTT-1NSAA are shown below.

$^1$H-NMR (600 MHz, CDCl$_3$): δ8.42 (s, 2H), 8.38 (s, 2H), 8.05 (m, 2H), 7.95 (m, 2H), 7.54 (m, 4H), 2.03 (s, 3H).

MS (70 eV, DI): 339.85 m/z

The detected value (339.85 m/z) of the mass spectrometry (MS) coincides with DNTT (molecular weight: 340.46), revealing that when DNTT-1NSAA is exposed to the conditions of mass spectrometry (70 eV, DI), NSAA is eliminated and DNTT is regenerated.

Example 1-2B

The addition reaction of dinaphthothienothiophene (DNTT) and N-sulfonylacetamide (NSAA) was confirmed by computer simulation using the above-described semi-empirical approach (MOPAC) and non-empirical approach (Gaussian).

The results are shown in the Table below. In the semi-empirical approach (MOPAC), the heat of formation of DNTT was set to 117.56 kcal/mol, and the heat of formation of NSAA was set to −49.27 kcal/mol.

TABLE 2

| Position of Addition | | Relative Heat of Formation (kcal/mol) | | |
|---|---|---|---|---|
| Nitrogen (N) | Sulfur (S) | MOPAC | Gaussian | Average |
| DNTT-1NSAA(1) | | | | |
| 12 | 13 | −8.70 | −11.94 | −10.32 |
| DNTT-1NSAA(2) | | | | |
| 12 | 14 | −59.40 | — | — |
| DNTT-1NSAA(2b) | | | | |
| 12 | 14 | −60.77 | — | — |
| DNTT-1NSAA(3) | | | | |
| 15 | 14 | −37.57 | — | — |
| DNTT-1NSAA(4) | | | | |
| 19 | 18 | decomposed | — | — |
| DNTT-1NSAA(5) | | | | |
| 23 | 24 | decomposed | — | — |
| DNTT-1NSAA(6) | | | | |
| 23 | 22 | decomposed | — | — |
| DNTT-1NSAA(7) | | | | |
| 9 | 13 | −60.33 | — | — |
| DNTT-1NSAA(7b) | | | | |
| 9 | 13 | −62.87 | — | — |
| DNTT-1NSAA(8) | | | | |
| 17 | 18 | −30.58 | — | — |
| DNTT-1NSAA(9) | | | | |
| 18 | 17 | −32.07 | — | — |
| DNTT-1NSAA(10) | | | | |
| 14 | 17 | −27.15 | — | — |
| DNTT-1NSAA(11) | | | | |
| 17 | 14 | −21.15 | — | — |

TABLE 2-continued

| Position of Addition | | Relative Heat of Formation (kcal/mol) | | |
|---|---|---|---|---|
| Nitrogen (N) | Sulfur (S) | MOPAC | Gaussian | Average |
| DNTT-1NSAA(12) | | | | |
| 19 | 20 | decomposed | — | — |
| DNTT-1NSAA(13) | | | | |
| 20 | 19 | −27.57 | — | — |
| DNTT-1NSAA(14) | | | | |
| 24 | 23 | decomposed | — | — |

As for the position of addition in Table 2, as shown in the chemical formula below, carbons of DNTT are numbered, and carbons coordinated with nitrogen (N) atom and sulfur (S) atom of NSAA are specified.

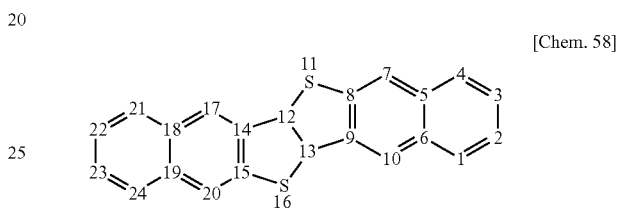

It is understood from the results in Table 2 that the reaction of adding NSAA to DNTT is feasible and in this case, NSAA is added to the center position of DNTT.

Example 1-3

The addition reaction of dinaphthothienothiophene (DNTT) and cyclopentadiene (CPD, the structural formula is shown below) was confirmed by computer simulation using the above-described semi-empirical approach (MOPAC) and non-empirical approach (Gaussian).

CPD

The results are shown in the Table below. In the semi-empirical approach (MOPAC), the heat of formation of DNTT was set to 117.56 kcal/mol, and the heat of formation of CPD was set to 37.97 kcal/mol.

TABLE 3

| Conditions of Addition | | Relative Heat of Formation (kcal/mol) | | |
|---|---|---|---|---|
| Number of Additions | Position of Addition | Gaussian | MOPAC | Average |
| DNTT-1CPD(T) | 1 | T | −6.05 | 5.09 | −0.48 |
| DNTT-1CPD(C) | 1 | C | −1.95 | −15.58 | −8.77 |
| DNTT-1CPD(M) | 1 | M | 0.14 | 18.28 | 9.21 |

TABLE 3-continued

| | Conditions of Addition | | Relative Heat of Formation (kcal/mol) | | |
|---|---|---|---|---|---|
| | Number of Additions | Position of Addition | Gaussian | MOPAC | Average |
| DNTT-1CPD(L) | 1 | L | −32.19 | −15.58 | −23.89 |
| DNTT-2CPD(TT) | 2 | T | 0.86 | 16.55 | 8.71 |
| DNTT-2CPD(MM) | 2 | M | −0.74 | 34.59 | 16.93 |
| DNTT-4CPD(TTTT) | 4 | T | 1.48 | 32.94 | 17.21 |
| CPD-CPD | 1 | — | 17.36 | 26.24 | 21.80 |

The positions of addition in Table 3 are illustrated below. Incidentally, the code "CPD-CPD" in Table 3 indicates an adduct compound wherein two CPD are added.

[Chem. 60]

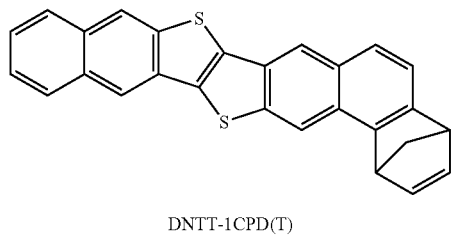

DNTT-1CPD(T)

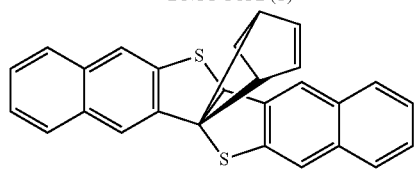

DNTT-1CPD(C)

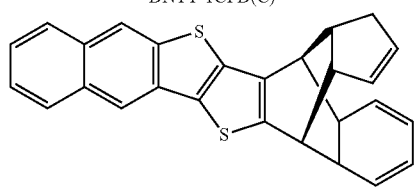

DNTT-1CPD(M)

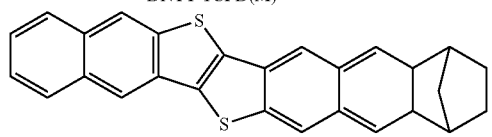

DNTT-1CPD(L)

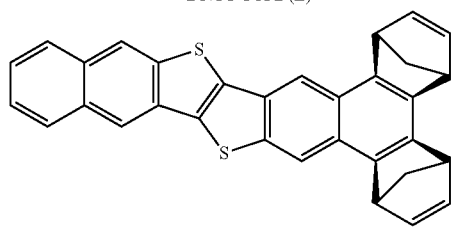

DNTT-2CPD(TT)

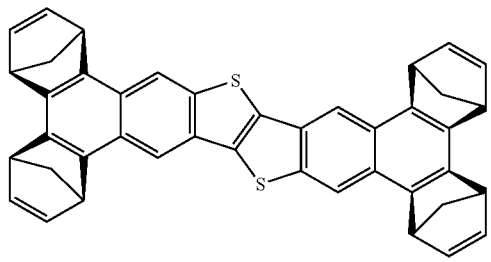

DNTT-4CPD(TTTT)

It is understood from the results in Table 3 that the addition reaction of adding CPD to DNTT is feasible.

Example 1-4

The addition reaction of dinaphthothienothiophene (DNTT) and furan (FRN, the structural formula is shown below) was confirmed by computer simulation using the above-described semi-empirical approach (MOPAC) and non-empirical approach (Gaussian).

[Chem. 61]

FRN

The results are shown in the Table below. In the semi-empirical approach (MOPAC), the heat of formation of DNTT was set to 117.56 kcal/mol, and the heat of formation of FRN was set to 2.96 kcal/mol.

TABLE 4

| | Conditions of Addition | | Relative Heat of Formation (kcal/mol) | | |
|---|---|---|---|---|---|
| | Number of Additions | Position of Addition | Gaussian | MOPAC | Average |
| DNTT-1FRN(T) | 1 | T | −22.51 | −6.07 | −14.29 |
| DNTT-1FRN(C) | 1 | C | −18.47 | −13.04 | −15.76 |
| DNTT-1FRN(M) | 1 | M | −12.31 | 9.53 | −1.39 |
| DNTT-2FRN(TT) | 2 | T | −30.34 | −4.67 | −17.51 |
| DNTT-2FRN(MM) | 2 | M | −25.38 | 17.28 | −4.05 |
| FRN-FRN | 1 | — | −11.31 | 6.70 | −2.31 |

The positions of addition in Table 4 are illustrated below. Incidentally, the code "FRN-FRN" in Table 4 indicates an adduct compound wherein two FRN are added.

[Chem. 62]

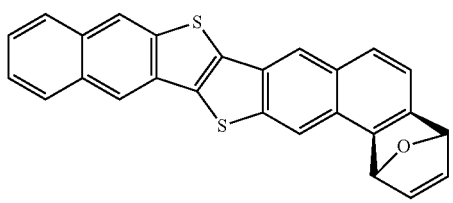

DNTT-1FRN(T)

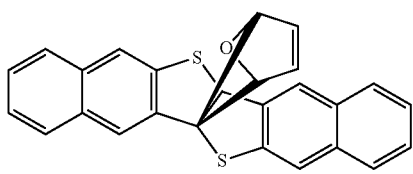

DNTT-1FRN(C)

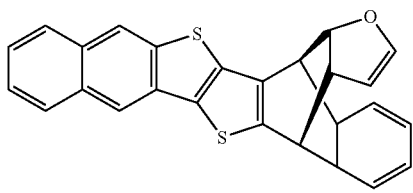

DNTT-1FRN(M)

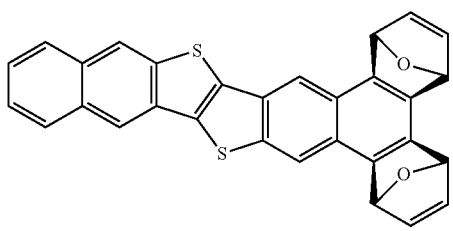

DNTT-2FRN(TT)

It is understood from the results in Table 4 that the addition reaction of adding FRN to DNTT is feasible.

Example 1-5

The addition reaction of dinaphthothienothiophene (DNTT) and anthracene (ANTH, the structural formula is shown below) was confirmed by computer simulation using the above-described semi-empirical approach (MOPAC) and non-empirical approach (Gaussian).

[Chem. 63]

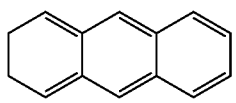

ANTH

The results are shown in the Table below. In the semi-empirical approach (MOPAC), the heat for formation of DNTT was set to 117.56 kcal/mol, and the heat for formation of ANTH was set to 62.92 kcal/mol.

TABLE 5

| | Conditions of Addition | | Relative Heat of Formation (kcal/mol) | | |
|---|---|---|---|---|---|
| | Number of Additions | Position of Addition | Gaussian | MOPAC | Average |
| DNTT-1ANTH | 1 | C | −10.44 | −1.50 | −5.97 |
| ANTH-ANTH | 1 | — | −10.37 | 6.61 | −1.88 |

The positions of addition in Table 5 are illustrated below.

[Chem. 64]

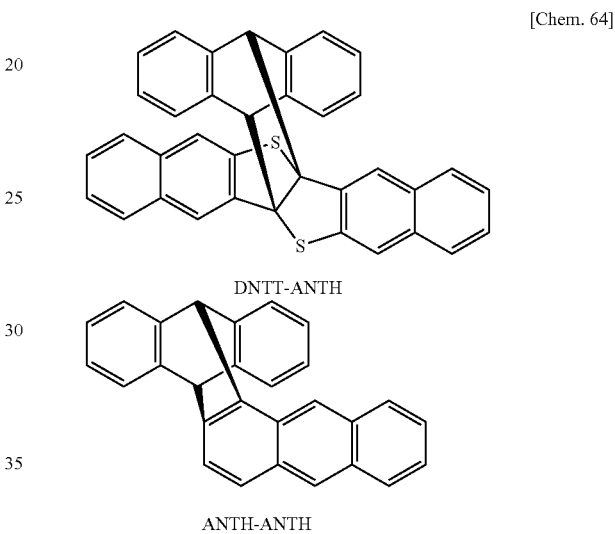

DNTT-ANTH

ANTH-ANTH

It is understood from the results in Table 5 that the addition reaction of adding ANTH to DNTT is feasible.

Example 1-6

The addition reaction of dinaphthothienothiophene (DNTT) and tricyanomethyl carboxylate-ethylene (TCPM, the structural formula is shown below) was confirmed by computer simulation using the above-described semi-empirical approach (MOPAC) and non-empirical approach (Gaussian).

[Chem. 65]

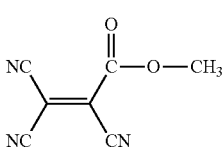

TCPM

The results are shown in the Table below. In the semi-empirical approach (MOPAC), the heat for formation of DNTT was set to 117.56 kcal/mol, and the heat for formation of TCPM was set to 40.24 kcal/mol.

TABLE 6

| | Conditions of Addition | | | Relative Heat of Formation (kcal/mol) | | |
|---|---|---|---|---|---|---|
| | Number of Additions | Position of Addition | Reaction | Gaussian | MOPAC | Average |
| DNTT-1TCPM(T) | 1 | T | light | −12.50 | −0.95 | −6.73 |
| DNTT-1TCPM(C) | 1 | C | light | −16.32 | −15.01 | −15.67 |
| DNTT-1TCPM(M) | 1 | M | heat | −12.87 | −1.08 | −6.98 |
| DNTT-1TCPM(L) | 1 | L | heat | −40.22 | −22.38 | −31.30 |
| DNTT-2TCPM(TT) | 2 | T | light | −11.10 | 4.07 | −3.52 |

Regarding the reaction conditions of addition reaction of Table 6, "light" and "heat" mean that the addition reaction can be proceed by light and heat, respectively. The positions of addition in Table 6 are illustrated below.

[Chem. 66]

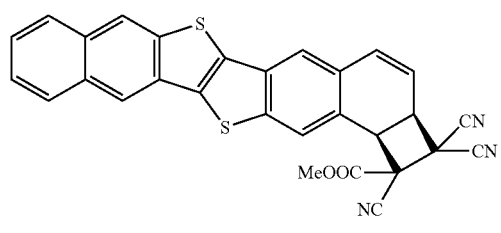

DNTT-1TCPM(T)

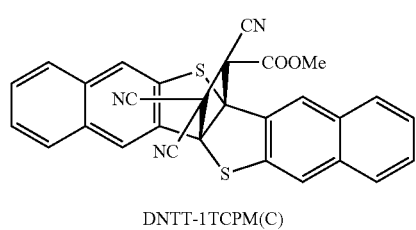

DNTT-1TCPM(C)

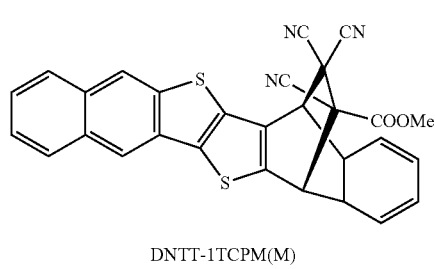

DNTT-1TCPM(M)

-continued

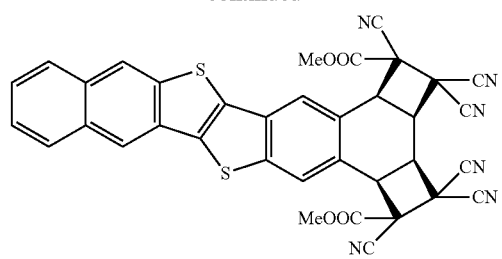

DNTT-2TCPM(TT)

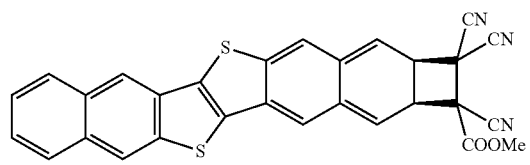

DNTT-1TCPM(L)

It is understood from the results in Table 6 that the addition reaction of adding TCPM to DNTT is feasible.

Example 1-7

The addition reaction of dinaphthothienothiophene (DNTT) and methylpyrrolecarboxylate (NMPC, the structural formula is shown below) was confirmed by computer simulation using the above-described semi-empirical approach (MOPAC) and non-empirical approach (Gaussian).

[Chem. 67]

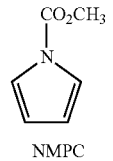

NMPC

The results are shown in the Table below. In the semi-empirical approach (MOPAC), the heat for formation of DNTT was set to 117.56 kcal/mol, and the heat of formation of NMPC was set to −30.46 kcal/mol.

TABLE 7

| | Conditions of Addition | | | Relative Heat of Formation (kcal/mol) | | |
|---|---|---|---|---|---|---|
| | Number of Additions | Position of Addition | Reaction | Gaussian | MOPAC | Average |
| DNTT-1NMPC(T) | 1 | T | heat | −29.50 | −15.76 | −22.63 |
| DNTT-1NMPC(C) | 1 | C | light | −24.73 | −23.47 | −24.10 |
| DNTT-1NMPC(M) | 1 | M | heat | −12.75 | 8.07 | −2.34 |
| DNTT-1NMPC(L) | 1 | L | heat | −50.58 | −19.32 | −34.95 |
| DNTT-2NMPC(TT) | 2 | T | heat | −42.29 | −24.87 | −33.58 |
| NMPC-NMPC | 1 | — | heat | −18.11 | −7.39 | −12.75 |

Regarding the reaction conditions of addition reaction of Table 7, "light" and "heat" mean that the addition reaction can be proceed by light and heat, respectively. The positions of addition in Table 7 are illustrated below.

[Chem. 68]

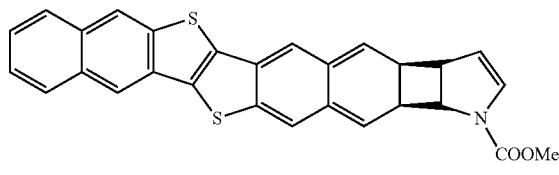

DNTT - 1NMPC(L)

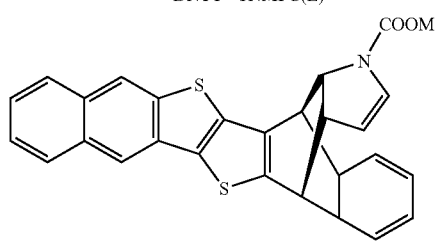

DNTT - 1NMPC(M)

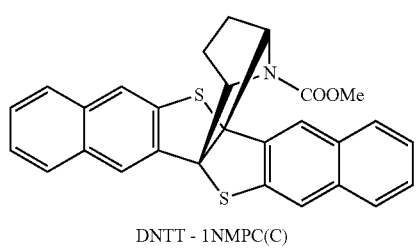

DNTT - 1NMPC(C)

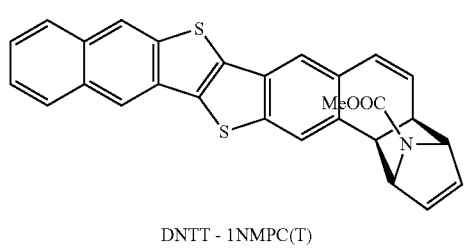

DNTT - 1NMPC(T)

-continued

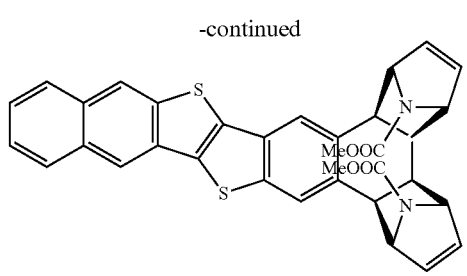

DNTT - 2NMPC(TT)

It is understood from the results in Table 7 that the addition reaction of adding NMPC to DNTT is feasible.

Example 1-8

The addition reaction of dinaphthothienothiophene (DNTT) and hydroxyphenyl-maleimide (HOPMI, the structural formula is shown below) was confirmed by computer simulation using the above-described semi-empirical approach (MOPAC) and non-empirical approach (Gaussian).

[Chem. 69]

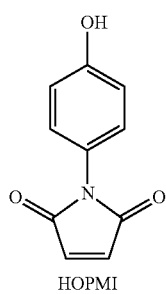

HOPMI

The results are shown in the Table below. In the semi-empirical approach (MOPAC), the heat for formation of DNTT was set to 117.56 kcal/mol, and the heat for formation of HOPMI was set to −38.13 kcal/mol.

TABLE 8

| | Conditions of Addition | | Relative Heat of Formation (kcal/mol) | | |
|---|---|---|---|---|---|
| | Number of Additions | Position of Addition | Reaction | Gaussian | MOPAC | Average |
| DNTT-1HOPMI(T) | 1 | T | light | −4.95 | 17.08 | 6.07 |
| DNTT-1HOPMI(C) | 1 | C | light | −3.38 | 6.91 | 1.77 |
| DNTT-1HOPMI(L) | 1 | L | heat | −32.54 | −4.59 | −18.57 |
| DNTT-1HOPMI(M) | 1 | M | heat | 6.60 | 24.88 | 15.74 |
| DNTT-2HOPMI(TT) | 2 | T | light | 6.43 | 42.00 | 24.22 |

Regarding the reaction conditions of addition reaction of Table 8, "light" and "heat" mean that the addition reaction can be proceed by light and heat, respectively. The positions of addition in Table 8 are illustrated below.

[Chem. 70]

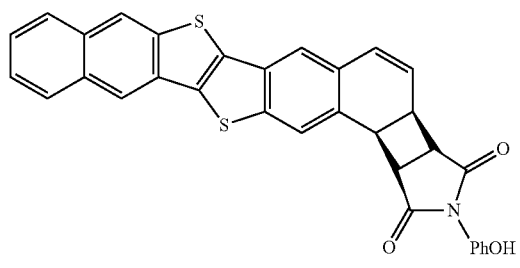

DNTT - 1HOPMI(T)

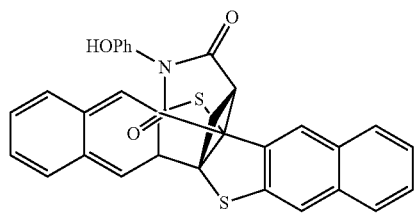

DNTT - 1HOPMI(C)

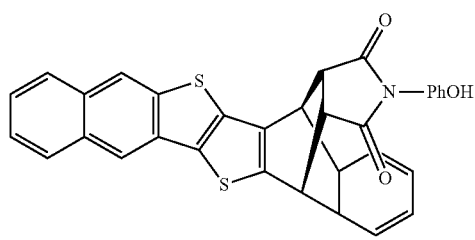

DNTT - 1HOPMI(M)

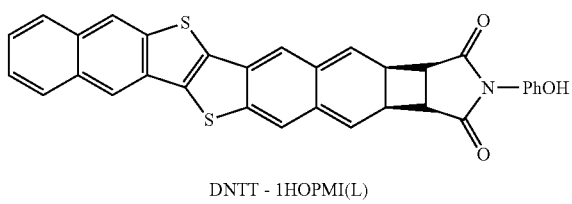

DNTT - 1HOPMI(L)

-continued

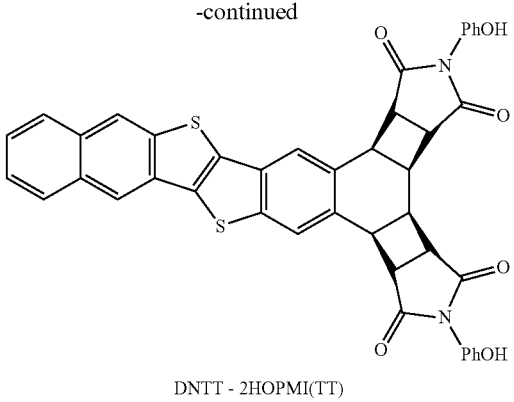

DNTT - 2HOPMI(TT)

It is understood from the results in Table 8 that the addition reaction of adding HOPMI to DNTT is feasible.

Example 1-9

The addition reaction of dinaphthothienothiophene (DNTT) and vinylene carbonate (VC (vinylene carbonate), the structural formula is shown below) was confirmed by computer simulation using the above-described semi-empirical approach (MOPAC) and non-empirical approach (Gaussian).

[Chem. 71]

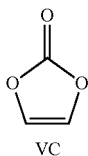

VC

The results are shown in the Table below. In the semi-empirical approach (MOPAC), the heat for formation of DNTT was set to 117.56 kcal/mol, and the heat for formation of VC was set to −59.30 kcal/mol.

TABLE 9

| | Conditions of Addition | | | Relative Heat of Formation (kcal/mol) | | |
|---|---|---|---|---|---|---|
| | Number of Additions | Position of Addition | Reaction | Gaussian | MOPAC | Average |
| DNTT-1VC(M) | 1 | M | heat | 9.73 | 49.34 | 29.54 |
| DNTT-1VC(L) | 1 | L | heat | −29.89 | 20.81 | −4.54 |
| DNTT-1VC(Z) | 1 | Z | heat | 7.61 | 47.69 | 27.65 |
| DNTT-1VC(T) | 1 | T | light | −2.62 | 42.43 | 19.91 |
| DNTT-1VC(C) | 1 | C | light | −1.42 | 30.88 | 14.73 |

Regarding the reaction conditions of addition reaction of Table 9, "light" and "heat" mean that the addition reaction can be proceed by light and heat, respectively.

The positions of addition in Table 9 are as shown in the following chemical formula.

[Chem. 72]

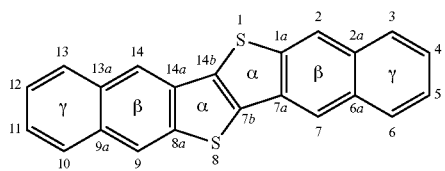

M-Position: 2-7
L-Position: 4-5
Z-Position: 3-6
T-Position: 3-4, or 5-6
C-Position: 7b-14b It is understood from the results in Table 9 that the addition reaction of adding VC to DNTT is feasible.

Example 1-10A 500 mg (1.47 mmol) of dinaphthothienothiophene (DNTT, MW=340.46) synthesized by the method indicated in Patent Document 2, 2.54 g (14.7 mmol, 1,000 mol % based on DNTT) of N-phenylmaleimide (PMI, MW=173.16, the structural formula is shown below), and 16.2 mg (1 mol % based on N-phenylmaleimide) of hydroquinone (MW: 110.1) as a radical scavenger were mixed in a mesitylene solvent, and the mixture was stirred at 160° C. over 2 hours in nitrogen, and thereby the Diels-Alder addition reaction of DNTT and PMI was performed.

[Chem. 73]

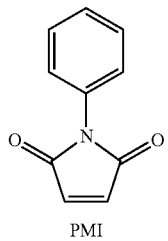

PMI

After the reaction, the solid matter was collected by filtration, and washed with chloroform. This solid matter was confirmed by NMR to be DNTT (raw material) (yielded amount: 422.3 mg, yield: 84.5 mol %).

The filtrate was separated by HPLC (high performance liquid chromatography, Agilent 1100 Series HPLC: High Performance Liquid Chromatography, SHISEIDO CAPCELL PAK C18 TYPE UG120, solvent: acetonitrile/water) to obtain 113.2 mg of an adduct compound wherein one molecule of PMI is added to DNTT (DNTT-1PMI, Mw=513.63, yield: 15.0 mol %).

The obtained DNTT-1PMI was a mixture of two kinds of stereoisomers (referred to as "stereoisomer A" and "stereoisomer B", respectively). The analysis results of these stereoisomers are shown below. Incidentally, from the results of NMR, it is estimated that the stereoisomer A is an endo form and the stereoisomer B is an exo form.

DNTT-1PMI (Stereoisomer A)
$^1$H-NMR (600 MHz, CDCl$_3$): δ 8.30 (S, 1H), 8.23 (S, 1H), 7.95 (m, 1H), 7.89 (m, 1H), 7.50 (m, 2H), 7.47 (m, 2H), 7.25 (m, 2H), 7.12 (t, J=7.3 Hz, 1H), 7.07 (dd, J=7.3 Hz, 7.7 Hz, 2H), 6.50 (d, J=7.7 Hz, 2H), 5.30 (d, J=3.3 Hz, 1H), 5.22 (d, J=3.3 Hz, 1H), 3.54 (dd, J=3.3 Hz, 8.1 Hz, 1H), 3.51 (dd, J=3.3 Hz, 8.1 Hz, 1H).
MS (70 eV, DI): 514.10 m/z DNTT-1PMI (Stereoisomer B)
$^1$H-NMR (600 MHz, CDCl$_3$): δ 8.33 (s, 1H), 8.25 (s, 1H), 7.97 (m, 1H), 7.90 (m, 1H), 7.49 (m, 2H), 7.42 (m, 1H), 7.40 (m, 1H), 7.31 (m, 1H), 7.30 (m, 2H), 7.26 (m, 2H), 6.53 (m, 2H), 5.22 (d, J=3.3 Hz, 1H), 5.18 (d, J=3.3 Hz, 1H), 3.59 (dd, J=3.3 Hz, 8.4 Hz, 1H), 3.56 (dd, J=3.3 Hz, 8.4 Hz, 1H).
MS (70 eV, DI): 513.05 m/z Both detected values of the mass spectrometry (MS) substantially coincide with DNTT-1PMI (Mw=513.63).

Figure 4:
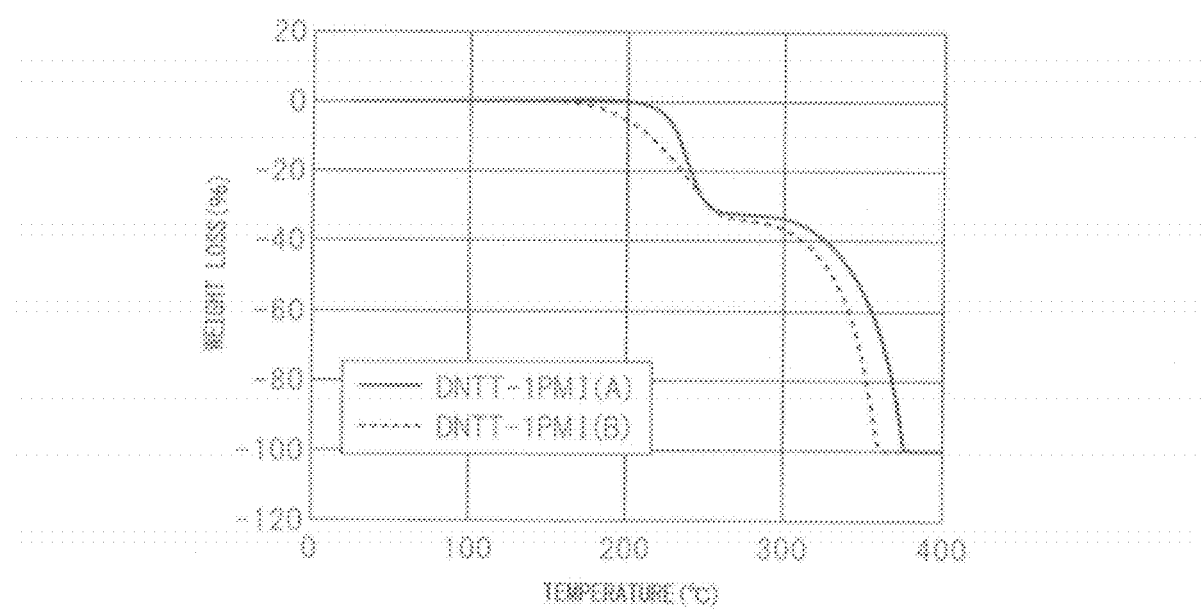
FIG. 4 is a view showing the thermal elimination characteristics of the adduct compound of Example 1-10A.

Using a differential thermal balance analysis (Rigaku TG-DTA TG8120), a temperature rise analysis was performed at 1° C./min in nitrogen to evaluate the thermal elimination characteristics of DNTT-1PMI (stereoisomers A and B). According to this analysis, the weight loss of DNTT-1PMI (stereoisomer A) was 31.9 wt % in the temperature range from 195° C. to 260° C. Also, the weight loss of DNTT-1PMI (stereoisomer B) was 32.7 wt % in the temperature range from 155° C. to 260° C. FIG. 4 shows the results. When PMI is thermally eliminated from DNTT-1PMI (MW=513.63) by the reverse Diels-Alder reaction, the weight loss is −33.7 wt % (calculated). Therefore the analysis results of DNTT-1PMI (stereoisomers A and B) reveal that PMI was eliminated by heating. Also, according to NMR, the sample after thermal elimination was confirmed to coincide with DNTT.

Using each of DNTT-1PMI (stereoisomers A and B), a bottom-contact bottom-gate FET (Field Effect Transistor) device was manufactured.

The substrate was obtained by producing source/drain gold electrodes having a channel length of 50 μm and a channel width of 1.5 mm on the SiO$_2$ oxide film of an n-doped silicon wafer (surface resistance: 0.005 Ω·cm) with an SiO$_2$ oxide film of 300 nm (bottom-contact).

While heating this substrate at 50° C., a chloroform 3 wt % solution of DNTT-1PMI (stereoisomer A or B) was dropped on the channel part of the substrate, and swiftly vaporized to obtain a film, and the film was heated to obtain an organic semiconductor device. For DNTT-1PMI (stereoisomer A), heating was performed at 200° C. for 2 hours by raising the temperature from room temperature at a heating rate of about 20° C./min in nitrogen. Also, for DNTT-1PMI (stereoisomer B), heating was performed at 160° C. for 2 hours by raising the temperature from room temperature at a heating rate of about 20° C./min in nitrogen or in the atmosphere.

Figure 5:
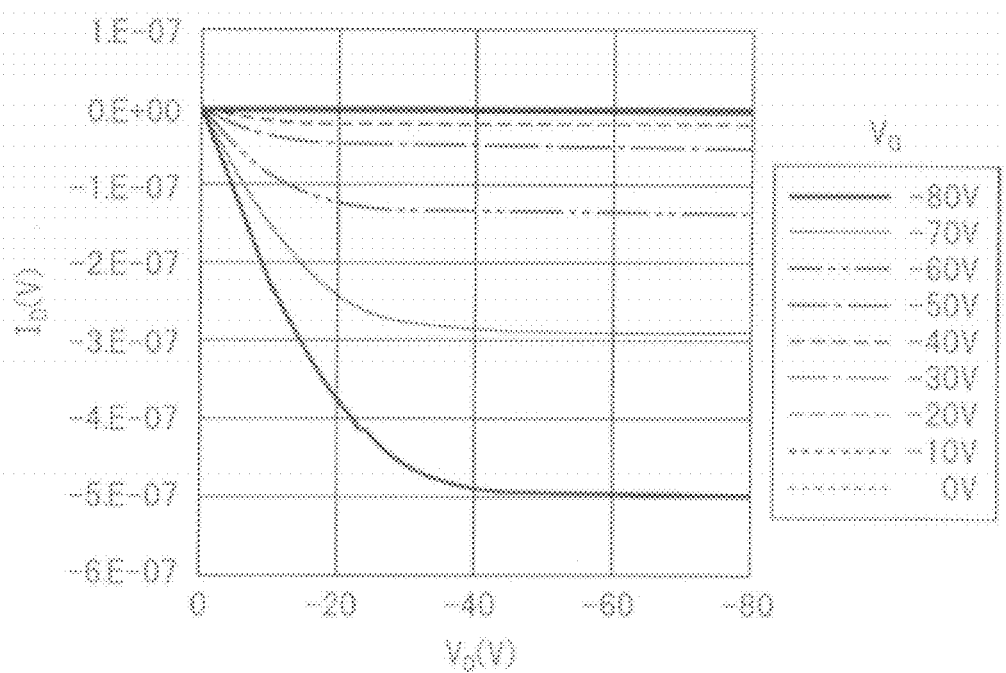
FIG. 5 is a view showing the output characteristics of the field effect transistor obtained in Example 1-10A.
Figure 6:
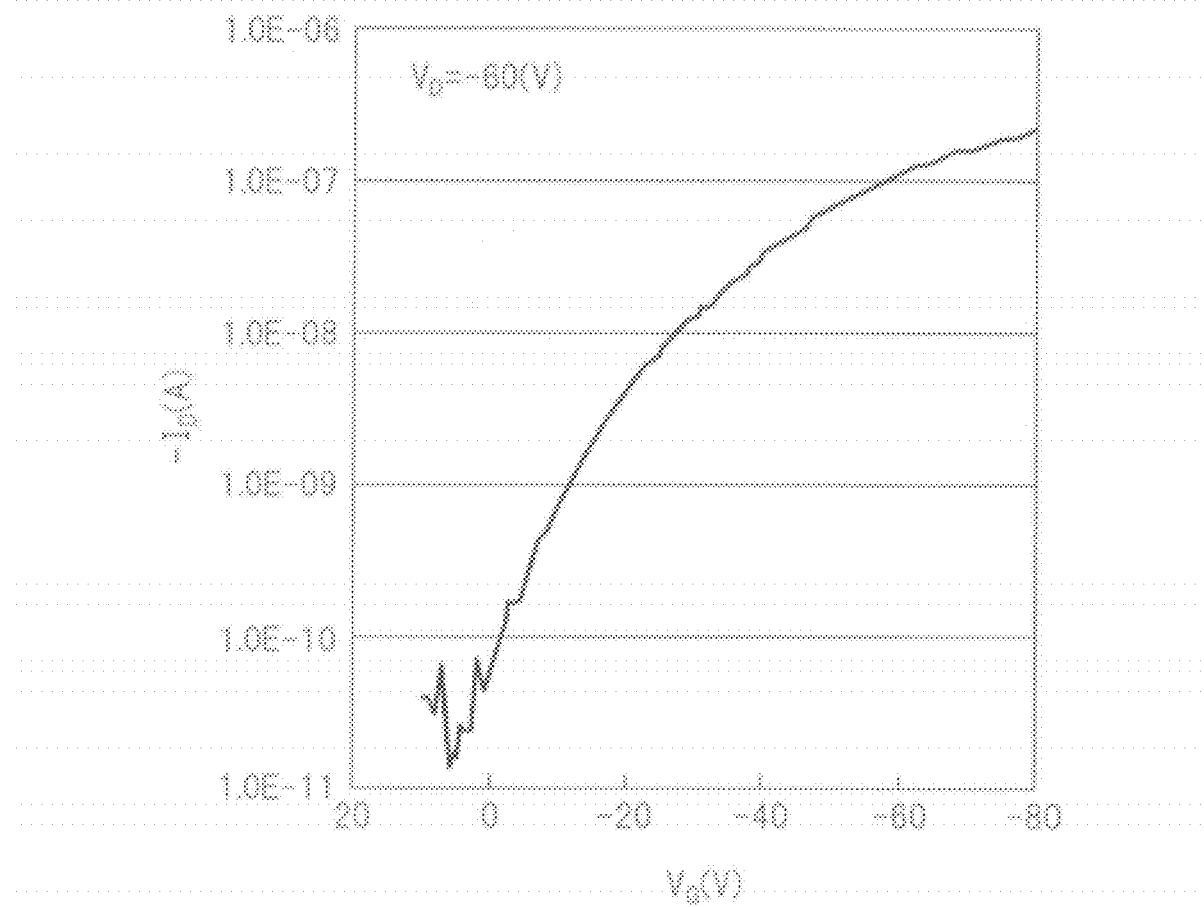
FIG. 6 is a view showing the transmission characteristics of the field effect transistor obtained in Example 1-10A.

Each of the organic semiconductor films obtained was evaluated for the characteristics, and found to exhibit p-type semiconductor characteristics. The carrier mobility was from 0.01 to 0.0001 cm$^2$/Vs, and the on/off ratio was from 10$^3$ to 10$^5$. That is, in case of DNTT-1PMI (stereoisomer B), semiconductor characteristics were obtained not only when performing the heating in nitrogen but also when performing the heating in the atmosphere. FIGS. 5 and 6 show the output characteristics and the transmission characteristics, respectively, as a field effect transistor (FET). In FIG. 5, the vertical axis indicates the drain current ($I_D(A)$), and the horizontal axis indicates the drain voltage ($V_D(V)$). Also, in FIG. 6, the vertical axis indicates the drain current ($I_D(A)$), and the horizontal axis indicates the gate voltage ($V_G(V)$).

Figure 8:
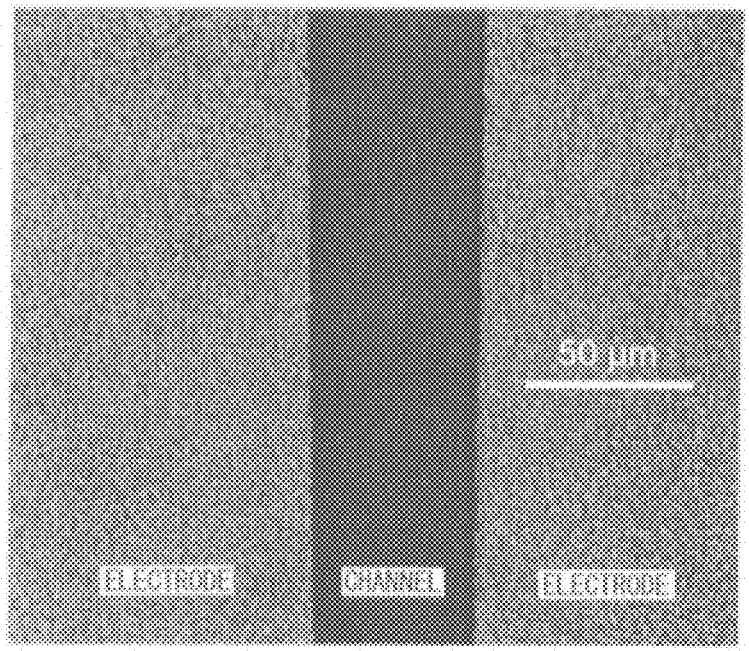
FIG. 8 is a micrograph showing the crystal state of DNTT in the channel part of the organic semiconductor film obtained in Example 1-10A.

Furthermore, the crystal state of DNTT in the channel part of the organic semiconductor film obtained using DNTT-1PMI (stereoisomer B) was observed by a polarizing microscope, and shown in FIG. 8. This observation of the channel part by the polarizing microscope revealed that, after the organic semiconductor film was obtained by heating, small crystal grains of about 1 μm were formed on the entire area of the organic semiconductor film. Accordingly, it was confirmed that PMI is eliminated from DNTT-1PMI by heating, and crystals of DNTT are produced.

Figure 7:
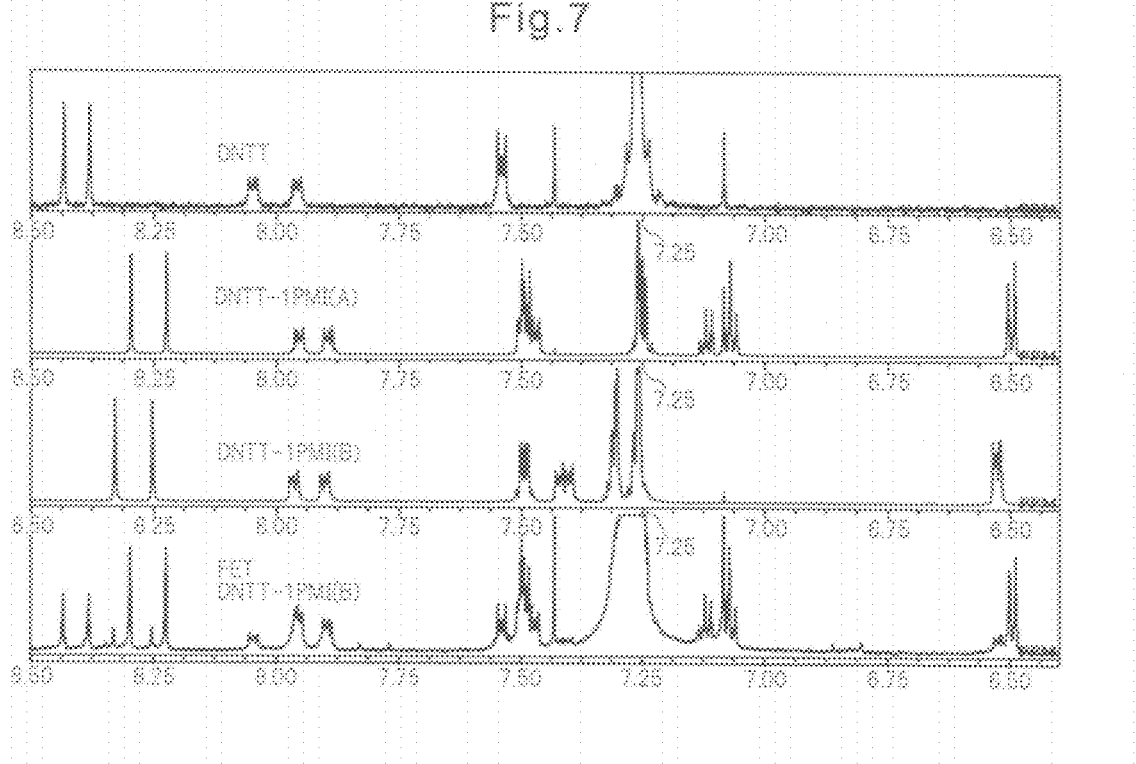
FIG. 7 is a view showing the NMR results of the residual adduct compound in the organic semiconductor film obtained in Example 1-10A.

With respect to the FET device having an organic semiconductor film obtained from DNTT-1PMI (stereoisomer B), the presence or absence of residual DNTT-1PMI (stereoisomers A and B) in the organic semiconductor film was confirmed by NMR. FIG. 7 shows the results. In FIG. 7, "DNTT", "DNTT-1PMI(A)", "DNTT-1PMI(B)", and "FET DNTT-1PMI(B)" indicate the analysis results of organic semiconductor films obtained from DNTT, DNTT-1PMI (stereoisomer A), DNTT-1PMI (stereoisomer B), and DNTT-1PMI (stereoisomer B), respectively.

According to FIG. 7, in the organic semiconductor film obtained from DNTT-1PMI (stereoisomer B), not only the NMR peak corresponding to DNTT but also the NMR peak corresponding to both DNTT-1PMI (stereoisomers A and B) are observed. That is, it was confirmed that even when DNTT-1PMI (stereoisomers A and B) remains in the organic semiconductor film, sufficient semiconductor characteristics can be provided.

DNTT has a low solubility, and therefore the peak tends not to be observed by NMR. On the other hand, DNTT-1PMI (stereoisomers A and B) has a high solubility, and therefore an NMR peak corresponding to the dissolved portion is observed. For this reason, the ratio between DNTT-1PMI and DNTT in the organic semiconductor film cannot be judged from the NMR results. Incidentally, as understood by the fact that the noise is increased, the peak of "DNTT" of FIG. 7 is shown by increasing the magnification compared with other peaks. Also, the size of the NMR peak of DNTT-1PMI (stereoisomers A and B) detected in the organic semiconductor film is in almost the same level as that of DNTT, revealing that the amount of the residual component DNTT-1PMI (stereoisomers A and B) is small.

Example 1-10B

The addition reaction of dinaphthothienothiophene (DNTT) and N-phenylmaleimide was confirmed by computer simulation using the above-described semi-empirical approach (MOPAC) and non-empirical approach (Gaussian).

The results are shown in the Table below. In the semi-empirical approach (MOPAC), the heat of formation of DNTT was set to 117.56 kcal/mol, and the heat of formation of PMI was set to 5.83 kcal/mol.

TABLE 10

| | Conditions of Addition | | Relative Heat of Formation (kcal/mol) | | | Heat of Formation Relative to DNTT-1PMI(M) or DNTT-1PMI(Z) (kcal/mol) | | |
|---|---|---|---|---|---|---|---|---|
| | Number of Additions | Position of Addition | Gaussian | MOPAC | Average | Gaussian | MOPAC | Average |
| DNTT-1PMI(M) | 1 | M | 6.39 | 24.77 | 15.58 | — | — | — |
| DNTT-1PMI(C) | 1 | C | −3.65 | 6.78 | 1.57 | — | — | — |
| DNTT-1PMI(Z) | 1 | Z | 3.96 | 22.72 | 13.34 | — | — | — |
| DNTT-2PMI(MM) | 2 | MM | 18.73 | 47.61 | 33.17 | 12.34 | 22.84 | 17.59 |
| DNTT-2PMI(ZZ) | 2 | ZZ | 13.98 | 45.64 | 29.81 | 10.02 | 22.92 | 16.47 |
| DNTT-2PMI(MZ) | 2 | NZ | 16.23 | 47.03 | 31.63 | 9.84 | 22.26 | 16.05 |
| DNTT-2PMI(ZM) | 2 | ZM | 16.29 | 47.03 | 31.66 | 12.33 | 24.31 | 18.32 |

The positions of addition in Table 10 are as shown in the following chemical formula.

[Chem. 74]

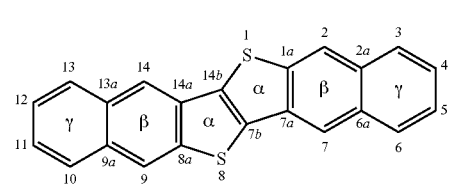

M-position: 2-7
C-position: 7b-14b
Z-position: 3-6
MM-position: 2-7 and 9-14
ZZ-position: 3-6 and 10-13
MZ-position and ZM-position: 2-7 and 10-13

It is understood from the results in Table 10 that the addition reaction of adding one molecule of PMI to one molecule of DNTT, and the addition reaction of adding two molecules of PMI to one molecule of DNTT are feasible.

Example 1-10C

The chloroform 1.5 wt % solution of DNTT-1PMI (stereoisomer A) synthesized in Example 1-10A was dropped on a substrate, and dried on a hot plate at 50° C. to form a thin film of DNTT-1PMI (stereoisomer A) on a substrate. The substrate was an n-doped silicon wafer (surface resistance: 0.005 Ω·cm, thickness: about 0.5 mm) with an $SiO_2$ oxide film of 300 nm.

This substrate with a DNTT-1PMI (stereoisomer A) thin film was placed by using tweezers on a hot plate heated at 210° C. in the atmosphere, rapidly heated and held for 3 minutes. By this rapid heating, phenylmaleimide was eliminated from DNTT-1PMI (stereoisomer A) and DNTT was deposited. It was observed with an eye that the thin film was changed from colorless to yellow in about 15 seconds by the rapid heating. Considering that the thermal elimination temperature of DNTT-1PMI (stereoisomer A) is 195° C., the temperature has reached about 200° C. in about 15 seconds, and this corresponds to a temperature rise rate of about 800° C./min.

Figure 9:
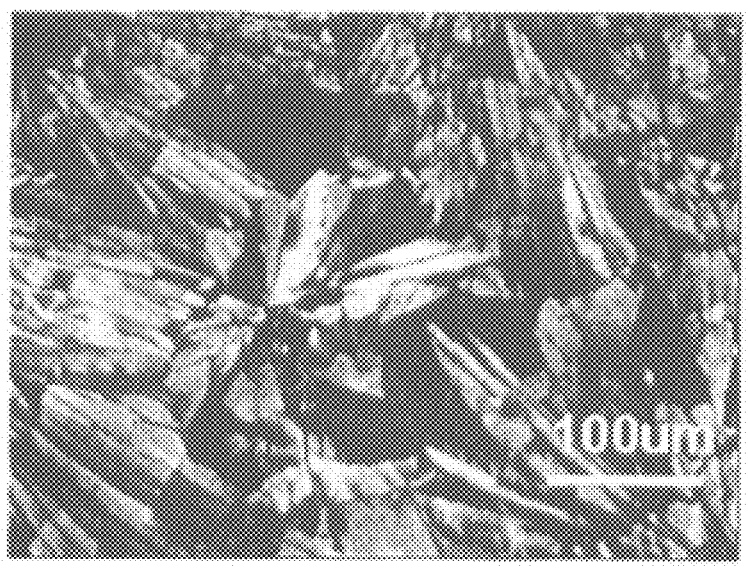
FIG. 9 is a polarized micrograph showing the crystal state of DNTT in the organic semiconductor film obtained in Example 1-10C.

DNTT deposited on the substrate was observed by a polarizing microscope, and shown in FIG. 9. As shown in FIG. 9, crystal grains of DNTT having a long axis diameter of more than 100 μm were deposited.

On the substrate having DNTT deposited thereon, source/drain gold electrodes having a channel length of 50 μm and a channel width of 1.5 mm was produced to manufacture an organic semiconductor device (bottom-gate top-contact). The obtained organic semiconductor film was evaluated for the characteristics, and found to exhibit p-type semiconductor characteristics. The carrier mobility was from 0.2 to 0.001 $cm^2/Vs$, and the on/off ratio was from $10^4$ to $10^6$.

Example 1-10D

DNTT was deposited in the same manner as in Example 1-10C, except that the substrate with a DNTT-1PMI (stereoisomer A) thin film was placed by using tweezers on a hot plate heated at 205° C., rapidly heated and held for 5 minutes. It was observed by eye that the thin film was changed from colorless to yellow in about 15 seconds by the rapid heating. Considering that the thermal elimination temperature of DNTT-1PMI (stereoisomer A) is 195° C., the temperature has reached about 200° C. in about 15 seconds, and this corresponds to a temperature rise rate of about 800° C./min.

Figure 10:
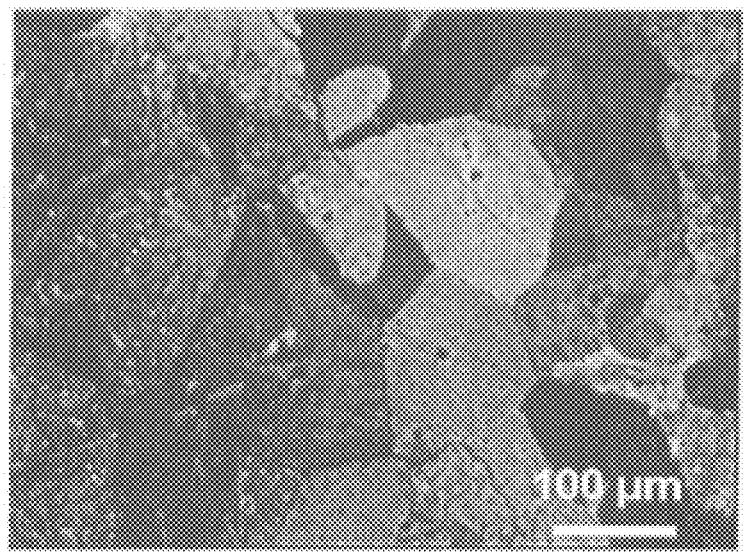
FIG. 10 is a polarized micrograph showing the crystal state of DNTT in the organic semiconductor film obtained in Example 1-10D.

DNTT deposited on the substrate was observed by a polarizing microscope, and shown in FIG. 10. As shown in FIG. 10, crystal grains of DNTT having a long axis diameter of more than 100 μm were deposited.

Example 1-10E

DNTT was deposited in the same manner as in Example 1-10C, except that the substrate with a DNTT-1PMI (stereoisomer A) thin film was placed by using tweezers on a hot plate at room temperature, the temperature was raised from room temperature to 210° C. in 10 minutes (heating rate of about 20° C./min) in the air atmosphere, and isothermally held at 210° C. over 3 minutes.

Figure 11:
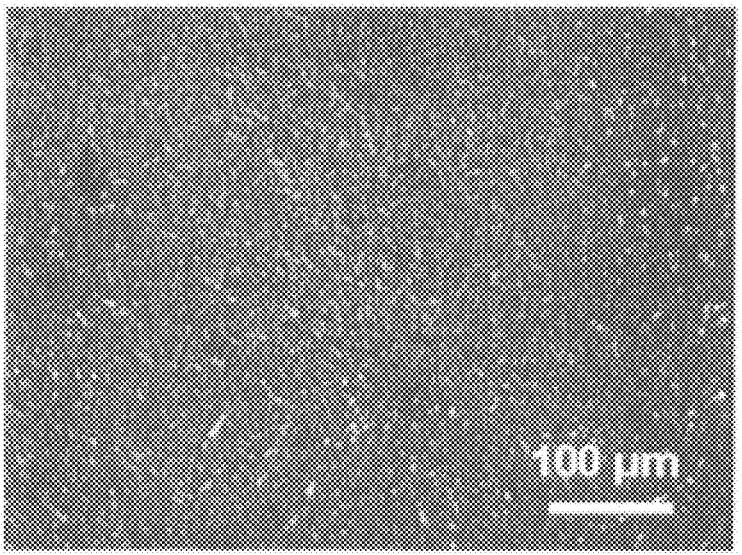
FIG. 11 is a polarized micrograph showing the crystal state of DNTT in the organic semiconductor film obtained in Example 1-10E.

DNTT deposited on the substrate was observed by a polarizing microscope, and shown in FIG. 11. As shown in FIG. 11, small crystal grains of DNTT of about 1 μm were deposited.

Example 1-10F

DNTT was deposited in the same manner as in Example 1-10C, except that DNTT-1PMI (stereoisomer B) synthesized in Example 1-10A was used in place of DNTT-1PMI (stereoisomer A), and the substrate with a DNTT-1PMI (stereoisomer B) thin film was placed by using tweezers on a hot plate heated at 170° C., rapidly heated and held for 15 minutes. It was observed by eye that the thin film was changed from colorless to yellow in about 15 seconds by the rapid heating. Considering that the thermal elimination temperature of DNTT-1PMI (stereoisomer B) is 155° C., the temperature has reached about 160° C. in about 15 seconds, and this corresponds to a temperature rise rate of about 640° C./min.

Figure 12:
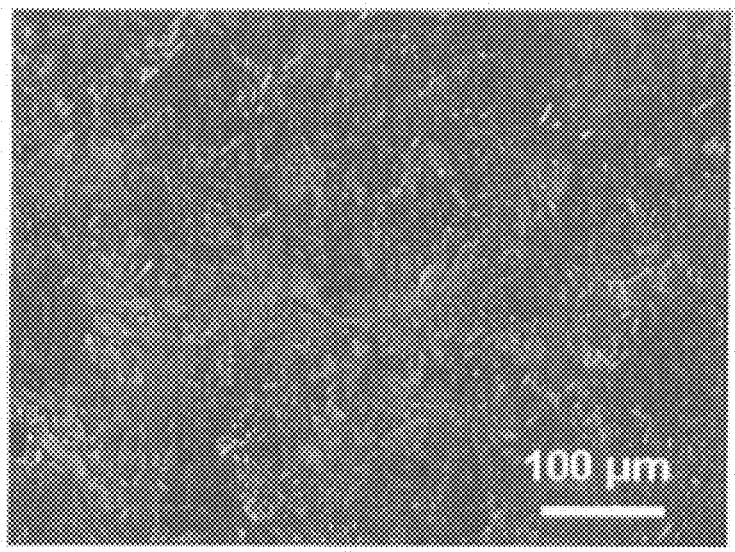
FIG. 12 is a polarized micrograph showing the crystal state of DNTT in the organic semiconductor film obtained in Example 1-10F.

DNTT deposited on the substrate was observed by a polarizing microscope, and shown in FIG. 12. As shown in FIG. 12, crystal grains of DNTT having a long axis diameter exceeding 20 μm were deposited.

Example 1-10G

DNTT was deposited in the same manner as in Example 1-10C, except that DNTT-1PMI (stereoisomer B) synthesized in Example 1-10A was used in place of DNTT-1PMI (stereoisomer A), and the substrate with a DNTT-1PMI (stereoisomer B) thin film was placed by using tweezers on a hot plate at room temperature, the temperature was raised from room temperature to 170° C. in 8 minutes (heating rate of about 20° C./min) in the air atmosphere, and isothermally held at 170° C. over 15 minutes.

Figure 13:
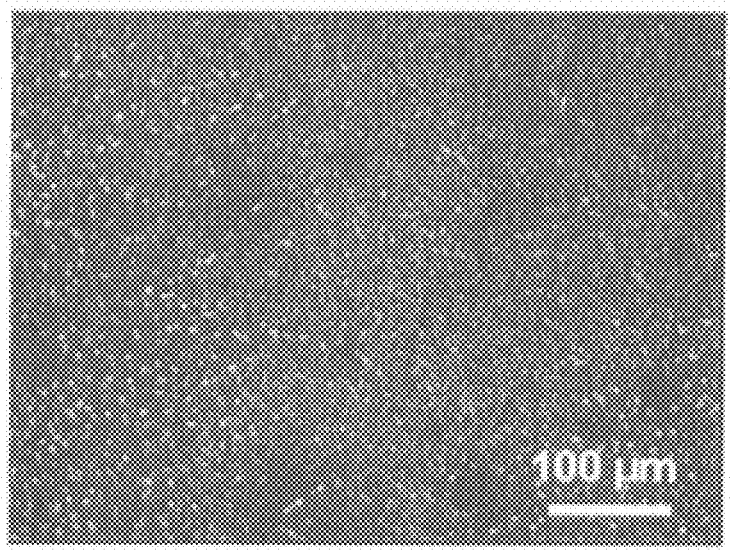
FIG. 13 is a polarized micrograph showing the crystal state of DNTT in the organic semiconductor film obtained in Example 1-10G.

DNTT deposited on the substrate was observed by a polarizing microscope, and shown in FIG. 13. As shown in FIG. 13, small crystal grains of DNTT of about 1 μm were deposited.

Example 1-11

The addition reaction of naphthoaldehyde (NAL, the structural formula is shown below) and N-phenylmaleimide (PMI, the structural formula is shown below) was confirmed by computer simulation using the above-described semi-empirical approach (MOPAC) and non-empirical approach (Gaussian).

[Chem. 75]

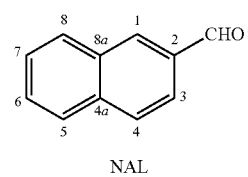

NAL

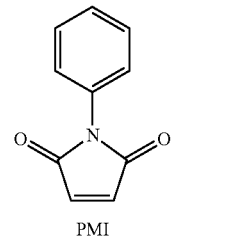

PMI

Similarly, the addition reaction of 3-methylthio-2-naphthoaldehyde (MTNAL, the structural formula is shown below) and N-phenylmaleimide (PMI, the structural formula is shown below) was confirmed by computer simulation.

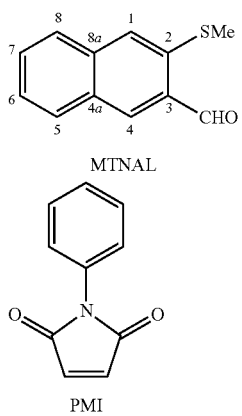

MTNAL

PMI

The results are shown in the Table below. In the semi-empirical approach (MOPAC), it was assumed that the heat of formation of NAL was set to 9.58 kcal/mol, the heat of formation of MTNAL was set to 12.28 kcal/mol, and the heat for formation of PMI was set to 5.83 kcal/mol.

TABLE 11

| | Conditions of Addition | | | Relative Heat of Formation (kcal/mol) | | |
|---|---|---|---|---|---|---|
| | Number of Additions | Position of Addition | Reaction | Gaussian | MOPAC | Average |
| NAL-1PMI(Z) | 1 | Z | heat | 2.91 | 20.27 | 11.59 |
| NAL-1PMI(M(Exo)) | 1 | M(Exo) | heat | 3.58 | 19.79 | 11.69 |
| NAL-1PMI(M(Endo)) | 1 | M(Endo) | heat | 3.85 | 19.61 | 11.73 |
| MTNAL-1PMI(Z) | 1 | Z | heat | 2.44 | 22.54 | 12.49 |
| MTNAL-1PMI(M(Exo)) | 1 | M(Exo) | heat | 8.31 | 24.68 | 16.50 |
| MTNAL-1PMI(M(Endo)) | 1 | M(Endo) | heat | 7.91 | 24.17 | 16.04 |

In the reaction conditions of addition reaction of Table 9, "heat" means that the addition reaction can be proceed by heat.

The positions of addition in Table 11 are as follows.

M-Position: 1-4

Z-Position: 8-5

It is understood from the results in Table 11 that the addition reaction of adding PMI to NAL, and the addition reaction of adding PMI to MTNAL are feasible. Also, it is understood from the results in Table 11 that both of the following Endo form and Exo form are formed.

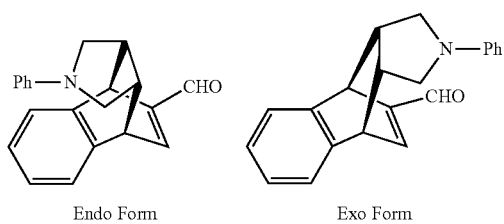

Endo Form    Exo Form

Example 1-12

500 mg (1.47 mmol) of dinaphthothienothiophene (DNTT, MW=340.46), 1.63 g (14.7 mmol, 1,000 mol % based on DNTT) of N-methylmaleimide (MMI, MW=111.1), and 16.2 mg (1 mol % based on N-methylmaleimide) of hydroquinone (MW: 110.1) as a radical scavenger were mixed in a mesitylene solvent, the mixture was stirred at 160° C. over 2 hours in nitrogen, and thereby the Diels-Alder addition reaction of DNTT and MMI was performed.

Thereafter, the solid matter was collected by filtration, and washed with chloroform. This solid matter was confirmed by NMR to be DNTT (raw material) (yielded amount: 343.5 mg, yield: 68.7 mol %).

The filtrate was separated by HPLC to obtain 113.2 mg of an adduct compound wherein one molecule of MMI is added to DNTT (DNTT-1MMI, Mw=451.56, yield: 28.5 mol %). The structural formula of this adduct compound is shown below.

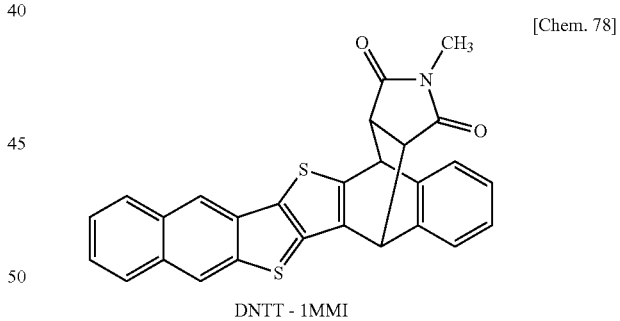

DNTT - 1MMI

The obtained DNTT-1MMP was a mixture of two kinds of stereoisomers (referred to as "stereoisomer A" and "stereoisomer B", respectively). The analysis results of these stereoisomers are shown below. Incidentally, from the results of NMR, it is estimated that the stereoisomer A is an endo form and the stereoisomer B is an exo form.

DNTT-1MMI (Stereoisomer A)

$^1$H-NMR (600 MHz, CDCl$_3$): δ 8.28 (s, 1H), 8.19 (s, 1H), 7.94 (m, 1H), 7.88 (m, 1H), 7.47 (m, 2H), 7.46 (m, 1H), 7.42 (m, 1H), 7.21 (m, 2H), 5.18 (d, J=2.9 Hz, 1H), 5.11 (d, J=2.9 Hz, 1H), 3.37 (dd, J=2.9 Hz, 7.7 Hz, 1H), 3.35 (dd, J=2.9 Hz, 7.7 Hz, 1H), 2.53 (s, 3H).

MS (70 eV, DI): 451.00 m/z

DNTT-1MMI (Stereoisomer B)

$^1$H-NMR (600 MHz, CDCl$_3$): δ 8.32 (s, 1H), 8.23 (s, 1H), 7.95 (m, 1H), 7.89 (m, 1H), 7.49 (m, 2H), 7.33 (m, 1H), 7.31 (m, 1H), 7.17 (m, 2H), 5.11 (d, J=3.3 Hz, 1H), 5.07 (d, J=3.3 Hz, 1H), 3.43 (dd, J=3.3 Hz, 8.4 Hz, 1H), 3.40 (dd, J=3.3 Hz, 8.4 Hz, 1H), 2.52 (s, 3H).

MS (70 eV, DI): 451.30 m/z

Both detected values of the mass spectrometry (MS) substantially coincide with DNTT-1MMI (Mw=451.56).

The thermal elimination characteristics of DNTT-1MMI were evaluated using a differential thermal balance analysis as in Example 1-10A. According to this evaluation, in DNTT-1MMI (stereoisomer A), thermal elimination occurred in the temperature range from 220° C. to 260° C. Incidentally, the amount of the sample of DNTT-1MMI (stereoisomer B) was small, and therefore evaluation of the thermal elimination characteristics could not be performed.

With respect to DNTT-1MMI (stereoisomer A), an organic semiconductor film was obtained as in Example 1-10A, and semiconductor characteristics thereof were evaluated. The heating for obtaining the organic semiconductor film was performed at 225° C. over 2 hours in nitrogen. The obtained organic semiconductor film was evaluated for the semiconductor characteristics, and found to exhibit p-type semiconductor characteristics. The carrier mobility was from 0.01 to 0.0001 cm$^2$/Vs, and the on/off ratio was from 10$^3$ to 10$^5$.

Example 1-13

500 mg (1.47 mmol) of dinaphthothienothiophene (DNTT, MW=340.46), 2.63 g (14.7 mmol, 1,000 mol % based on DNTT) of N-cyclohexylmaleimide (CHMI, MW=179.22), and 16.2 mg (1 mol % based on N-cyclohexylmaleimide) of hydroquinone (MW: 110.1) as a radical scavenger were mixed in a mesitylene solvent, the mixture was stirred at 160° C. over 2 hours in nitrogen, and thereby the Diels-Alder addition reaction of DNTT and CHMI was performed.

Thereafter, the solid matter was collected by filtration and washed with chloroform. This solid matter was confirmed by NMR to be DNTT (raw material) (yielded amount: 478.5 mg, yield: 95.7 mol %).

The filtrate was separated by HPLC to obtain 28.9 mg of an adduct compound wherein one molecule of CHMI is added to DNTT (DNTT-1CHMI, Mw=519.13, yield: 2.1 mol %). The structural formula of this adduct compound is shown below.

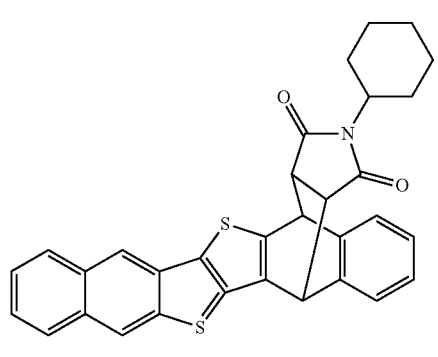

[Chem. 79]

DNTT - 1CHMI

The analysis results of the obtained DNTT-1CHMI are shown below. Incidentally, with respect to DNTT-1CHMI, a stereoisomer was not obtained.

$^1$H-NMR (600 MHz, CDCl$_3$): δ 8.31 (s, 1H), 8.23 (s, 1H), 7.95 (m, 1H), 7.89 (m, 1H), 7.48 (m, 2H), 7.33 (m, 1H), 7.32 (m, 1H), 7.17 (m, 2H), 5.08 (d, J=3.4 Hz, 1H), 5.05 (d, J=3.4 Hz, 1H), 3.51 (m, 1H), 3.33 (dd, J=3.4 Hz, 8.3 Hz, 1H), 3.30 (dd, J=3.4 Hz, 8.3 Hz, 1H), 1.68 (m, 4H), 1.58 (m, 1H), 1.09 (m, 3H), 0.84 (m, 2H).

MS (70 eV, DI): 519.20 m/z

The detected value of the mass spectrometry (MS) substantially coincides with DNTT-1CHMI (Mw=519.13).

The thermal elimination characteristics of DNTT-1CHMI were evaluated using a differential thermal balance analysis as in Example 1-10A. According to this evaluation, thermal elimination of DNTT-1CHMI occurred in the temperature range from 200° C. to 280° C.

An organic semiconductor film was obtained from DNTT-1CHMI as in Example 1-10A, and semiconductor characteristics thereof were evaluated. The heating for obtaining the organic semiconductor film was performed at 210° C. over 2 hours in nitrogen. The obtained organic semiconductor film was evaluated for the semiconductor characteristics, and found to exhibit p-type semiconductor characteristics. The carrier mobility was from 0.01 to 0.0001 cm$^2$/Vs, and the on/off ratio was from 10$^3$ to 10$^5$.

Example 1-14

2,000 mg (5.87 mmol) of dinaphthothienothiophene (DNTT, MW=340.46), 10.99 g (58.7 mmol, 1,000 mol % based on DNTT) of N-benzylmaleimide (BZMI, MW=187.19), and 64.8 mg (1 mol % based on N-benzylmaleimide) of hydroquinone (MW: 110.1) as a radical scavenger were mixed in a mesitylene solvent, the mixture was stirred at 160° C. over 4 hours in nitrogen, and thereby the Diels-Alder addition reaction of DNTT and BZMI was performed.

Thereafter, the solid matter was collected by filtration, and washed with chloroform. This solid matter was confirmed by NMR to be DNTT (raw material) (yielded amount: 980 mg, yield: 49.0 mol %).

The filtrate was separated by HPLC to obtain 659.2 mg of an adduct compound wherein one molecule of BZMI is added to DNTT (DNTT-1BZMI, Mw=527.10, yield: 21.3 mol %). The structural formula of this adduct compound is shown below.

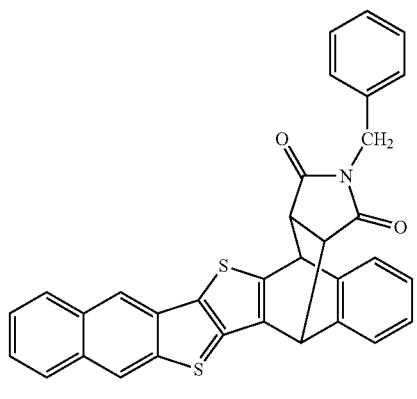

[Chem. 80]

DNTT - 1BZMI

The analysis results of the obtained DNTT-1BZMI are shown below. Incidentally, with respect to DNTT-1BZMI, a stereoisomer was not obtained.

$^1$H-NMR (600 MHz, CDCl$_3$): δ 8.31 (s, 1H), 8.22 (s, 1H), 7.95 (m, 1H), 7.89 (m, 1H), 7.48 (m, 2H), 7.23 (m, 2H), 7.18 (t, J=7.3 Hz, 1H), 7.14 (dd, J=7.3 Hz, 7.3 Hz, 2H), 6.99 (m, 2H), 6.75 (d, J=7.3 Hz, 2H), 5.08 (d, J=3.3 Hz, 1H), 5.05 (d, J=3.3 Hz, 1H), 4.28 (s, 2H), 3.44 (dd, J=3.3 Hz, 8.4 Hz, 1H), 3.41 (dd, J=3.3 Hz, 8.4 Hz, 1H).

MS (70 eV, DI): 527.95 m/z

The detected value of the mass spectrometry (MS) substantially coincides with DNTT-1BZMI (Mw=527.10).

The thermal elimination characteristics of DNTT-1BZMI were evaluated using a differential thermal balance analysis as in Example 1-10A. According to this evaluation, thermal elimination of DNTT-1BZMI occurred in the temperature range from 190° C. to 260° C.

An organic semiconductor film was obtained from DNTT-1BZMI as in Example 1-10A, and semiconductor characteristics thereof were evaluated. The heating for obtaining the organic semiconductor film was performed at 200° C. over 2 hours in nitrogen. The obtained organic semiconductor film was evaluated for the characteristics and found to exhibit p-type semiconductor characteristics. The carrier mobility was from 0.01 to 0.0001 cm$^2$/Vs, and the on/off ratio was from $10^3$ to $10^5$.

Example 1-15

500 mg (1.47 mmol) of dinaphthothienothiophene (DNTT, MW=340.46), 2.25 g (14.7 mmol, 1,000 mol % based on DNTT) of N-tert-butylmaleimide (TBMI, MW=153.18), and 16.2 mg (1 mol % based on N-tert-butylmaleimide) of hydroquinone (MW: 110.1) as a radical scavenger were mixed in a mesitylene solvent, the mixture was stirred at 160° C. over 4 hours in nitrogen, and thereby the Diels-Alder addition reaction of DNTT and TBMI was performed.

Thereafter, the solid matter was collected by filtration, and washed with chloroform. This solid matter was confirmed by NMR to be DNTT (raw material) (yielded amount: 486 mg, yield: 97.2 mol %).

The filtrate was separated by HPLC to obtain 2.1 mg of an adduct compound wherein one molecule of TBMI is added to DNTT (DNTT-1TBMI, Mw=493.64, yield: 0.29 mol %). The structural formula of this adduct compound is shown below.

[Chem. 81]

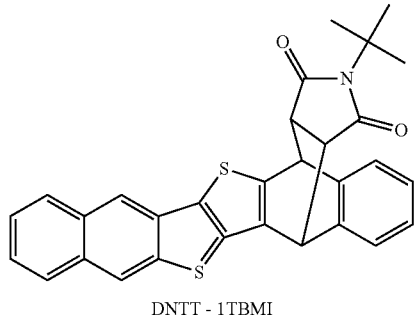

DNTT - 1TBMI

The analysis result of DNTT-1TBMI are shown below. Incidentally, with respect to DNTT-1TBMI, a stereoisomer was not obtained.

$^1$H-NMR (600 MHz, CDCl$_3$): δ 8.31 (s, 1H), 8.22 (s, 1H), 7.95 (m, 1H), 7.89 (m, 1H), 7.48 (m, 2H), 7.35 (m, 1H), 7.33 (m, 1H), 7.18 (m, 2H), 5.06 (d, J=3.3 Hz, 1H), 5.02 (d, J=3.3 Hz, 1H), 3.23 (dd, J=3.3 Hz, 8.8 Hz, 1H), 3.16 (dd, J=3.3 Hz, 8.8 Hz, 1H), 2.59 (s, 9H).

Example 1-16

500 mg (1.47 mmol) of dinaphthothienothiophene (DNTT, MW=340.46), 1.44 g (14.7 mmol, 1,000 mol % based on DNTT) of maleic anhydride (MA, MW=98.06), and 16.2 mg (1 mol % based on maleic anhydride) of hydroquinone (MW: 110.1) as a radical scavenger were mixed in a mesitylene solvent, the mixture was stirred at 160° C. over 4 hours in nitrogen, and thereby the Diels-Alder addition reaction of DNTT and MA was performed.

Thereafter, the solid matter was collected by filtration, and washed with chloroform. This solid matter was confirmed by NMR to be DNTT (raw material) (yielded amount: 472.2 mg, yield: 94.4 mol %).

The filtrate was separated by HPLC to obtain 32.2 mg of an adduct compound wherein one molecule of MA is added to DNTT (DNTT-1MA, Mw=438.52, yield: 5.0 mol %). The structural formula of this adduct compound is shown below.

[Chem. 82]

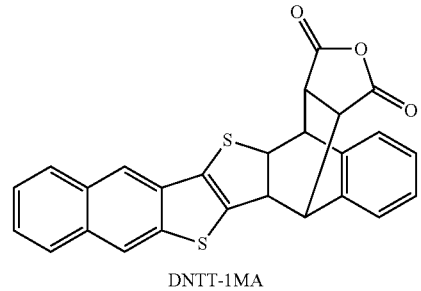

DNTT-1MA

The analysis results of the obtained DNTT-1MA are shown below.

$^1$H-NMR (600 MHz, CDCl$_3$): δ 8.31 (s, 1H), 8.22 (s, 1H), 7.95 (m, 1H), 7.89 (m, 1H), 7.48 (m, 2H), 7.23 (m, 2H), 7.00 (m, 2H), 5.09 (d, J=3.3 Hz, 1H), 5.05 (d, J=3.3 Hz, 1H), 3.44 (dd, J=3.3 Hz, 8.4 Hz, 1H), 3.41 (dd, J=3.3 Hz, 8.4 Hz, 1H).

MS (70 eV, DI): 341.31 m/z

The detected value of the mass spectrometry (MS) coincides with DNTT (molecular weight: 340.46), revealing that when DNTT-1MA is exposed to the conditions of mass spectrometry (70 eV, DI), MA is eliminated and DNTT is regenerated.

Example 2-1

In Example 2-1 to Comparative Example 2-2 below, the structure of the target compound was determined as needed by $^1$H-NMR (1H-nuclear magnetic resonance spectrum) and MS (mass spectrometry). The devices used are as follows.

$^1$H-NMR: JNM-A-600 (600 MHz)

MS: Shimazu QP-5050A (Production of DNTT)

In accordance with the method indicated in Supporting Information of Non-Patent Document 1, 4.03 g (11.8 mmol, yield: 38.56%) of dinaphthothienothiophene (DNTT) (MW=340.46, the structural formula is shown below) was obtained from 9.59 g (61.4 mmol) of 2-naphthoaledehyde (MW=156.18) as a starting material.

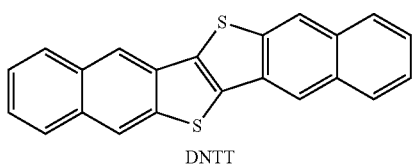

DNTT (Purification of DNTT by Solvent Washing)

Figure 15:
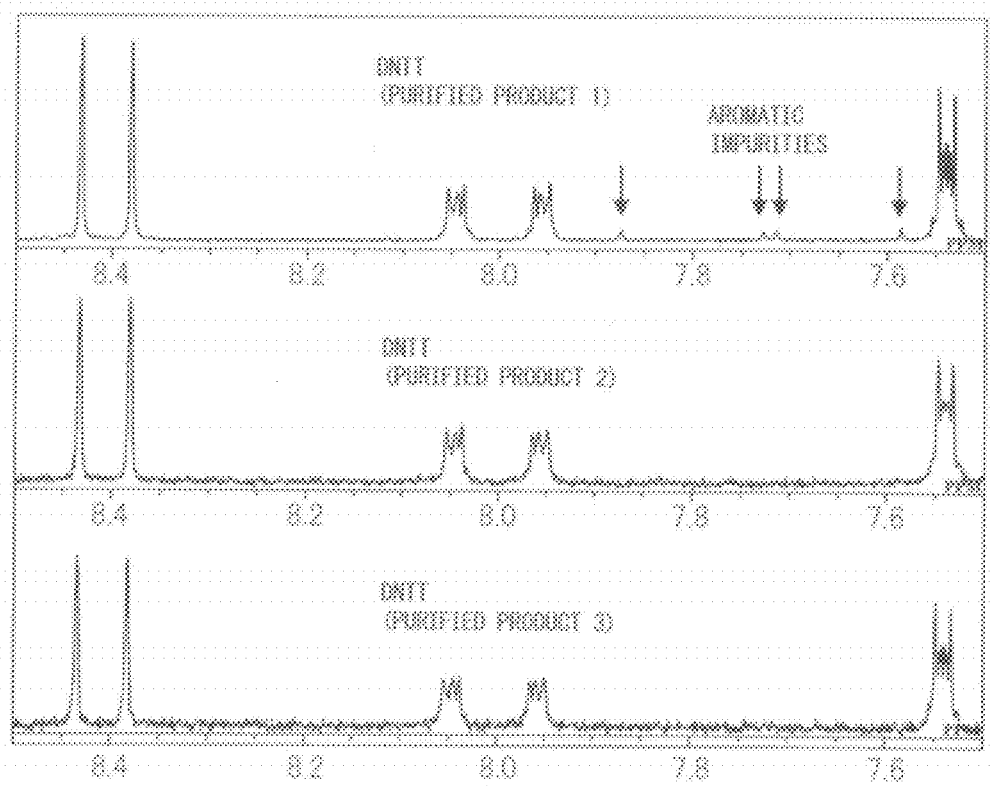
FIG. 15 is a view showing the NMR (nuclear magnetic resonance analysis) results of DNTT (Purification Products 1 to 3) of Example 2-1.

The thus-obtained DNTT was washed with chloroform and a hexane solvent, and filtered through a filter. At this time, the color of DNTT (Purified Product 1) was grayish yellow. Pure DNTT is yellow, and therefore the coloring in gray of this DNTT (Purified Product 1) is considered to be caused by the DNTT solid's embracement of iodine used during production of DNTT. Also, as shown in FIG. 15, according to NMR (nuclear magnetic resonance analysis), this DNTT (Purified Product 1) was confirmed to contain aromatic impurities. The impurity content of DNTT (Purified Product 1) was about 11 mol % as calculated based on the proton ratio of $^1$H-NMR data.

(Purification of DNTT by Method of the Present Invention)

To 500 mg of DNTT (Purified Product 1) above, 2.54 g (118.3 mmol, 1,000 mol % based on DNTT) of N-phenylmaleimide (PMI) (MW=173.16), 16.2 mg (1 mol % based on N-phenylmaleimide) of hydroquinone (MW: 110.1) as a radical scavenger, and a mesitylene solvent were added to obtain a mixed solution, this mixed solution was stirred at 160° C. over 2 hours in a nitrogen atmosphere, and thereby the Diels-Alder addition reaction of DNTT by N-phenylmaleimide was performed.

Thereafter, the solid matter of the mixed solution was collected by filtration, and the obtained solid matter was washed with chloroform. This solid matter was confirmed by NMR to be DNTT (Purified Product 2) (yielded amount: 422.3 mg, yield: 84.4 mol %). The DNTT (Purified Product 2) had a yellow color, revealing that the coloring component assumed to be iodine was removed. Also, as shown in FIG. 15, according to NMR (nuclear magnetic resonance analysis), it was also confirmed that in the DNTT (Purified Product 2), aromatic organic components as impurities observed in DNTT (Purified Product 1) were removed.

(Purification of DNTT by Sublimation)

For obtaining organic semiconductor characteristics by DNTT, higher purity is indispensable. Accordingly, the DNTT (Purified Product 2) obtained above was further purified three times by the sublimation purification method, and this product was designated as DNTT (Purified Product 3).

(Manufacture of FET Device)

A top-contact bottom-gate field effect transistor (FET: Field Effect Transistor) device was manufactured using DNTT (Purified Product 3) by the vapor deposition method. Specifically, an n-doped silicon wafer (surface resistance: 0.005 Ω·cm) with an SiO$_2$ oxide film of 300 nm was subjected to a UV ozone treatment over 20 minutes (Eye UV-Ozone Cleaning System OC-250615-D+A, Eye Graphics Co., Ltd.) to obtain a UV ozone-treated silicon substrate. Also, a toluene solution containing 10 mmol of octadecyltrichlorosilane (ODTS, LS-6495, Shin-Etsu Chemical Co., Ltd.) was prepared, and the UV ozone-treated silicon substrate was dipped in the solution for 24 hours. Thereafter, by the vacuum deposition method (resistance heating-type vapor deposition apparatus: SVC-700 TM/700-2, Sanyu Electron Co., Ltd.), a thin film of about 50 nm was produced using DNTT (Purified Product 3), and source/drain gold electrodes having a channel width of 50 μm and a channel length of 1.5 mm were produced on the DNTT (top-contact).

This FET device was evaluated for the semiconductor characteristics, and found to exhibit p-type semiconductor characteristics. The carrier mobility was 1.3 cm$^2$/Vs, and the on/off ratio was 10$^7$.

Example 2-2

The filtrate obtained in the purification of DNTT by the method of the present invention in Example 2-1 was separated by HPLC (high performance liquid chromatography, Agilent 1100 Series HPLC: High Performance Liquid Chromatography, SHISEIDO CAPCELL PAK C18 TYPE UG120, solvent: acetonitrile/water) to obtain a dinaphthothienothiophene-phenylmaleimide 1 adduct (DNTT-1PMI, stereoisomer: Endo form and Exo form, Mw=513.63, yielded amount: 113.2 mg, yield: 15.0 mol %) of the following formula.

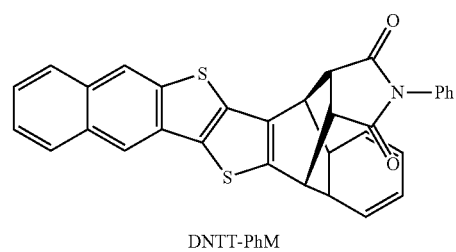

DNTT-PhM

The analysis results of DNTT-1PMI (Endo form and Exo form) are shown in the following (1) and (2), respectively.

(1) DNTT-1PMI (Endo Form)

$^1$H-NMR (600 MHz, CDCl$_3$): δ 8.30 (S, 1H), 8.23 (S, 1H), 7.95 (m, 1H), 7.89 (m, 1H), 7.50 (m, 2H), 7.47 (m, 2H), 7.25 (m, 2H), 7.12 (t, J=7.3 Hz, 1H), 7.07 (dd, J=7.3 Hz, 7.7 Hz, 2H), 6.50 (d, J=7.7 Hz, 2H), 5.30 (d, J=3.3 Hz, 1H), 5.22 (d, J=3.3 Hz, 1H), 3.54 (dd, J=3.3 Hz, 8.1 Hz, 1H), 3.51 (dd, J=3.3 Hz, 8.1 Hz, 1H). MS (70 eV, DI): 514.10 m/z (2) DNTT-1PMI (Exo Form) $^1$H-NMR (600 MHz, CDCl$_3$): δ 8.33 (s, 1H), 8.25 (s, 1H), 7.97 (m, 1H), 7.90 (m, 1H), 7.49 (m, 2H), 7.42 (m, 1H), 7.40 (m, 1H), 7.31 (m, 1H), 7.30 (m, 2H), 7.26 (m, 2H), 6.53 (m, 2H), 5.22 (d, J=3.3 Hz, 1H), 5.18 (d, J=3.3 Hz, 1H), 3.59 (dd, J=3.3 Hz, 8.4 Hz, 1H), 3.56 (dd, J=3.3 Hz, 8.4 Hz, 1H).

MS (70 eV, DI): 513.05 m/z

The detected values (514.10 m/z and 513.05 m/z) of the mass spectrometry (MS) coincided with DNTT-phenylmaleimide 1 adduct (DNTT-1PMI) (Mw=513.63).

Figure 16:
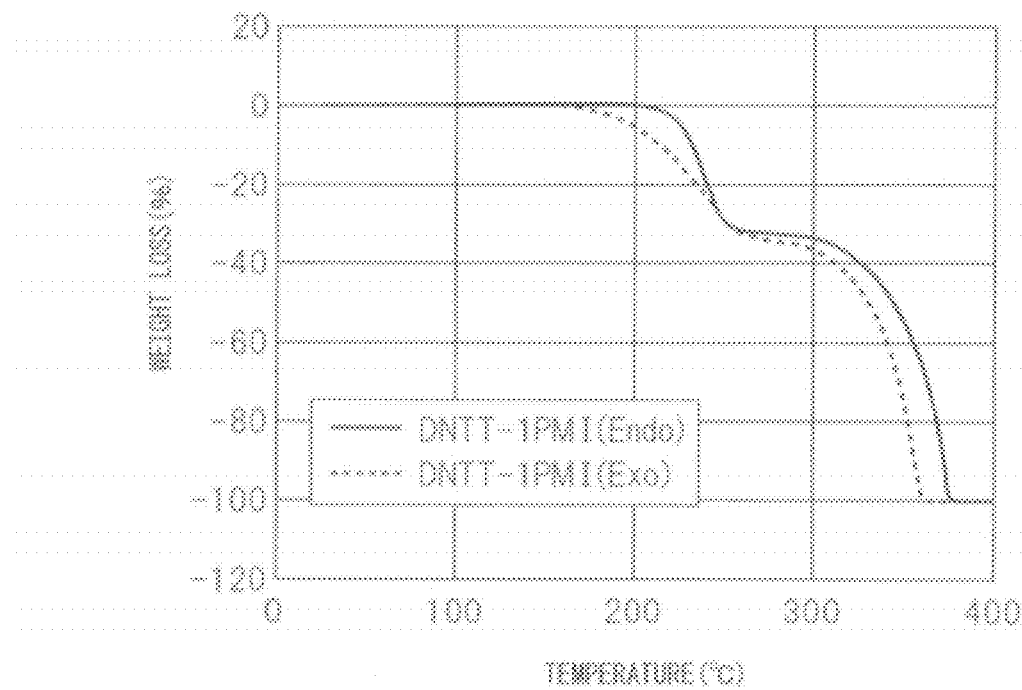
FIG. 16 is a view showing the elimination characteristics of the DNTT-phenylmaleimide 1 adduct (DNTT-1PMI) (Endo form, Exo form) obtained in Example 2-1.

With respect to the thermal elimination characteristics of DNTT-1PMI (Endo form and Exo form), it was confirmed by the differential thermal balance analysis (Rigaku TG-DTA TG8120, nitrogen atmosphere, temperature rise analysis of 1° C./min) that, as shown in FIG. 16, the weight loss in the range from 195° C. to 260° C. was 31.9 wt % in the Endo form, while the weight loss in the range from 155° C. to 260° C. was 32.7 wt % in the Exo form.

When PMI is thermally eliminated from DNTT-1PMI (MW=513.63) by the reverse Diels-Alder reaction, the weight loss as calculated is 33.7 wt %, and this coincides with the analysis result. Also, the sample after thermal elimination was confirmed by NMR to coincide with DNTT.

DNTT-1PMI (Endo form, Exo form) was heated to 260° C. in a nitrogen atmosphere to obtain 64.2 mg of purified DNTT (Purified Product 2'). This DNTT (Purified Product 2') had a yellow color, revealing that the coloring component assumed to be iodine was removed. Also, as shown in FIG. 15, according to NMR (nuclear magnetic resonance analysis), it was also confirmed that in the DNTT (Purified Product 2'), aromatic organic components as impurities observed in DNTT (Purified Product 1) were removed.

In total amount and yield of DNTT from the solid matter obtained by filtration (Purified Product 2 of Example 2-1) and DNTT obtained from DNTT-1PMI (Purified Product 2' of Example 2-2) were 486.5 mg and 97.3 mol %, respectively.

Comparative Example 2-1

DNTT (Purified Product 3') was obtained in the same manner as in Example 2-1, except that purification of DNTT by the method of the present invention was not performed. That is, DNTT (Purified Product 3') was obtained by purifying DNTT of Example 2-1 (Purified Product 1) three times by the sublimation purification method. In the DNTT after sublimation purification, the gray coloring was slightly lightened, but the gray component could not be removed.

Using the thus-obtained DNTT (Purified Product 3'), an FET device was manufactured by the vapor deposition method in the same manner as Example 2-1. This FET device was evaluated for the semiconductor characteristics, and found to exhibit p-type semiconductor characteristics. The carrier mobility was 0.023 cm$^2$/Vs, and the on/off ratio was 10$^4$. Accordingly, the FET device of Comparative Example 2-1 was significantly inferior to the FET device of Example 2-1.

Comparative Example 2-2

DNTT (Purified Product 1) of Example 2-1 was stirred in a mesitylene solvent at 160° C. over 2 hours in a nitrogen atmosphere. By this purification, the gray coloring of DNTT (Purified Product 1) was not changed and maintained. Accordingly, it is considered that by the purification above, iodine embraced in the DNTT (Purified Product 1) solid was not removed.

Example 3-1

In this Example, an organic semiconductor film-forming solution containing two kinds of adduct compounds were prepared, and the state of deposition as a solid matter was evaluated.

An adduct compound (DNTT-1PMI (stereoisomer A)) wherein one molecule of N-phenylmaleimide (PMI) was added to dinaphthothienothiophene (DNTT) was obtained as in Example 1-10A. According to the results of NMR, this DNTT-1PMI (stereoisomer A) was presumed to be an endo form. Also, an adduct compound (DNTT-1CHMI) wherein one molecule of N-cyclohexylmaleimide (CHMI) was added to dinaphthothienothiophene (DNTT) was obtained as in Example 1-13.

DNTT-1PMI and DNTT-1CHMI in a total amount of 1.0 mass % were added to chloroform to obtain an organic semiconductor film-forming solution. The molar ratio between DNTT-1PMI and DNTT-1CHMI was adjusted to 1:1.

<Evaluation of Crystallization>

The organic semiconductor film-forming solution obtained above was dropped on a silicon wafer, and chloroform as the solvent was volatilized in the atmosphere at ordinary temperature to deposit a solid matter. The state of deposition of the solid matter was observed by a microscope. FIG. 17 shows the result. FIG. 17(a) is a photograph showing the entirety of the solid matter, and FIG. 17(a) is an enlarged photograph (500 times) of the solid matter.

As understood from FIG. 17, the solid matter was deposited as a film, and substantially no crystallization had proceeded. It is believed that, because two kinds of adduct compounds were contained in the organic semiconductor film-forming solution, crystallization is inhibited at the time of volatilizing the solvent to deposit a solid matter.

<Manufacture of FET>

Using the organic semiconductor film-forming solution above, a bottom-contact bottom-gate FET (Field effect Transistor) device was manufactured as follows.

The substrate was obtained by producing source/drain gold electrodes having a channel length of 50 μm and a channel width of 1.5 mm on the SiO$_2$ oxide film of an n-doped silicon wafer (surface resistance: 0.005 Ω·cm) with an SiO$_2$ oxide film of 300 nm (bottom-contact).

The organic semiconductor film-forming solution was dropped on the channel part of the substrate at room temperature and swiftly volatilized to obtain a film, and the film was heated to obtain an organic semiconductor film. Thereafter, the film was heated at 210° C. over 2 hours in nitrogen to obtain an organic semiconductor film.

The film was observed before and after heating in nitrogen. FIG. 18 shows the results. FIG. 18(a) shows the observation result before heating (annealing), and FIG. 18(b) shows the observation result after heating. It is understood from FIG. 18 that fine crystal grains are deposited over the entire organic semiconductor film by heating.

The organic semiconductor film of the obtained FET was evaluated for the semiconductor characteristics, and found to exhibit p-type semiconductor characteristics. The carrier mobility was at most 0.01 cm$^2$/Vs, and the on/off ratio was at most 10$^5$.

Example 3-2

In this Example, an organic semiconductor film-forming solution containing an adduct compound and a compound constituting the adduct compound was prepared, and the state of deposition as a solid matter was confirmed.

An adduct compound (DNTT-1PMI (stereoisomer A)) wherein one molecule of N-phenylmaleimide (PMI) was added to dinaphthothienothiophene (DNTT) was obtained as in Example 1-10A. According to the results of NMR, this DNTT-1PMI (stereoisomer A) was presumed to be an endo form.

DNTT-1PMI in an amount of 1.0 mass % and PMI in an amount of 1 mol % based on DNTT-1PMI were added to chloroform to obtain an organic semiconductor film-forming solution.

<Evaluation of Crystallization>

The organic semiconductor film-forming solution obtained above was dropped on a silicon wafer, and chloroform as the solvent was volatilized in the atmosphere at ordinary temperature to deposit a solid matter. The state of deposition of the solid matter was observed by a microscope, as a result, the solid matter was deposited as a film, and substantially no crystallization had proceeded. It is believed that, because an adduct compound and a compound constituting the adduct compound were contained in the organic semiconductor film-forming solution, crystallization is inhibited at the time of volatilizing the solvent to deposit a solid matter.

<Manufacture of FET>

Using the organic semiconductor film-forming solution above, a bottom-contact bottom-gate FET device was manufactured as in Example 3-1. The organic semiconductor film of the obtained FET was evaluated for the semiconductor characteristics, and found to exhibit p-type semiconductor characteristics. The carrier mobility was at most 0.01 cm$^2$/Vs, and the on/off ratio was at most 10$^5$.

Example 3-3

In this Example, an organic semiconductor film-forming solution containing an adduct compound and a compound constituting the adduct compound was prepared, and the state of deposition as a solid matter was evaluated.

An adduct compound (DNTT-1CHMI) wherein one molecule of N-cyclohexylmaleimide (CHMI) was added to dinaphthothienothiophene (DNTT) was obtained as in Example 1-13.

DNTT-1CHMI in an amount of 1.0 mass % and PMI in an amount of 1 mol % based on DNTT-1CHMI were added to chloroform to obtain an organic semiconductor film-forming solution.

<Evaluation of Crystallization>

The organic semiconductor film-forming solution obtained above was dropped on a silicon wafer, and chloroform as the solvent was volatilized in the atmosphere at ordinary temperature to deposit a solid matter. The state of deposition of the solid matter was observed by a microscope, as a result, the solid matter was deposited as a film, and substantially no crystallization had proceeded. It is believed that, because an adduct compound and a compound constituting the adduct compound were contained in the organic semiconductor film-forming solution, crystallization is inhibited at the time of volatilizing the solvent to deposit a solid matter.

<Manufacture of FET>

Using the organic semiconductor film-forming solution above, a bottom-contact bottom-gate FET device was manufactured as in Example 3-1. The organic semiconductor film of the obtained FET was evaluated for the semiconductor characteristics, and found to exhibit p-type semiconductor characteristics. The carrier mobility was at most 0.01 cm$^2$/Vs, and the on/off ratio was at most 10$^5$.

Comparative Example 3-1

In this Comparative Example, an organic semiconductor film-forming solution containing only an adduct compound was prepared, and the state of deposition as a solid matter was evaluated.

An adduct compound (DNTT-1PMI (stereoisomer A)) wherein one molecule of N-phenylmaleimide (PMI) was added to dinaphthothienothiophene (DNTT) was obtained as in Example 1-10A. According to the results of NMR, this DNTT-1PMI (stereoisomer A) was presumed to be an endo form.

DNTT-1PMI in an amount of 1.0 mass % was added to chloroform to obtain an organic semiconductor film-forming solution.

<Evaluation of Crystallization>

Figure 19:
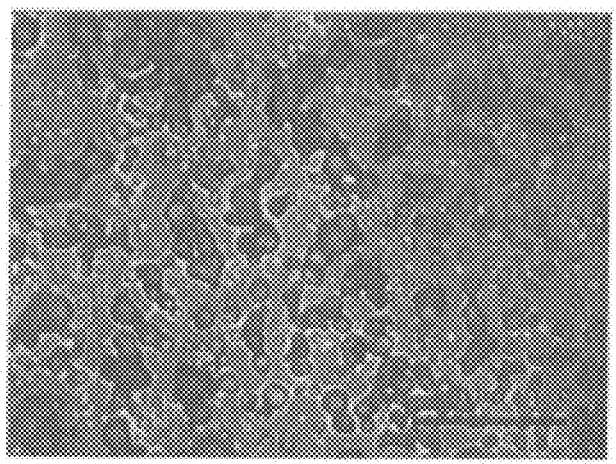
FIG. 19 is a photograph showing the solid matter obtained from the organic semiconductor film-forming solution of Comparative Example 3-1.

The organic semiconductor film-forming solution obtained above was dropped on a silicon wafer, and chloroform as the solvent was volatilized in the atmosphere at ordinary temperature to deposit a solid matter. FIG. 19 shows the result. FIG. 19 is an enlarged photograph (500 times) of the solid matter.

As understood from FIG. 19, the solid matter was deposited as particles, and a film of the solid matter was not obtained. It is believed that crystallization of DNTT-1PMI had proceeded in the course of the solvent volatilizing from the organic semiconductor film-forming solution.

<Manufacture of FET>

Figure 20:
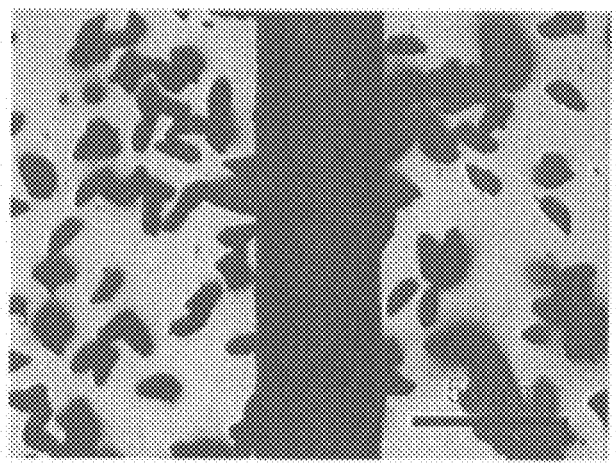
FIG. 20 is a photograph showing the organic semiconductor film of FET obtained from the organic semiconductor film-forming solution of Comparative Example 3-1.

Using the organic semiconductor film-forming solution above, a bottom-contact bottom-gate FET device was manufactured as in Example 3-1. Although the characteristics of the organic semiconductor film of the obtained FET were evaluated, characteristics as a semiconductor were not obtained. Also, the organic semiconductor film of the obtained FET was observed with a polarizing microscope. FIG. 20 shows the result. As understood from FIG. 20, the organic semiconductor forms particles, and a channel of the organic semiconductor film was not formed in the channel between electrodes.

Example 4-1

The addition reaction of dinaphthothienothiophene (DNTT) and vinylene carbonate (VC (vinylene carbonate), the structural formula is shown below) was evaluated by computer simulation using the above-described semi-empirical approach (MOPAC) and non-empirical approach (Gaussian).

[Chem. 85]

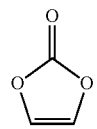

VC

The results are shown in the Table below. In the semi-empirical approach (MOPAC), the heat for formation of DNTT was set to 117.56 kcal/mol, and the heat for formation of VC was set to −59.30 kcal/mol.

TABLE 12

| | Conditions of Addition | | | Relative Heat of Formation (kcal/mol) | | |
|---|---|---|---|---|---|---|
| | Number of Additions | Position of Addition | Reaction | Gaussian | MOPAC | Average |
| DNTT-1VC(M) | 1 | M | heat | 9.73 | 49.34 | 29.54 |
| DNTT-1VC(L) | 1 | L | heat | −29.89 | 20.81 | −4.54 |
| DNTT-1VC(Z) | 1 | Z | heat | 7.61 | 47.69 | 27.65 |
| DNTT-1VC(T) | 1 | T | light | −2.62 | 42.43 | 19.91 |
| DNTT-1VC(C) | 1 | C | light | −1.42 | 30.88 | 14.73 |

Regarding the reaction conditions of addition reaction of Table 12, "light" and "heat" mean that the addition reaction occurs due to light and heat, respectively.

The positions of addition in Table 12 are as shown in the following chemical formula.

[Chem. 86]

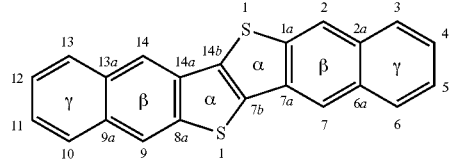

M-Position: 2-7
L-Position: 4-5
Z-Position: 3-6
T-Position: 3-4, or 5-6
C-Position: 7b-14b It is understood from the results in Table 12 that the addition reaction of adding VC to DNTT is realizable.

DESCRIPTION OF REFERENCE NUMERALS AND SIGNS

1 Organic semiconductor
2 Source electrode
3 Drain electrode
5 Dielectric layer (silicon oxide)
7 Silicon wafer substrate (gate electrode)
10 Organic semiconductor device

The invention claimed is:

1. An adduct compound, wherein said adduct compound has a structure wherein a double bond-containing compound (II) is added in an eliminatable state to a substituted or unsubstituted fused polycyclic aromatic compound of the following formula (I-4) through said double bond:

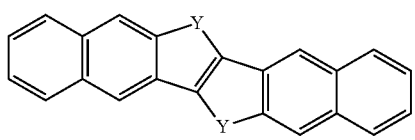 (I-4)

(wherein each Y is independently an element selected from the group consisting of chalcogens);
wherein said double bond-containing compound (II) has either one of the following formulae (II-1) to (II-12):

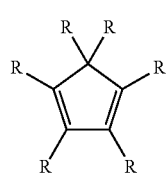 (II-1)

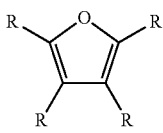 (II-2)

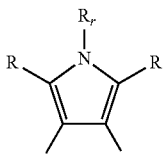 (II-3)

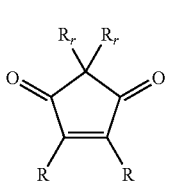 (II-4)

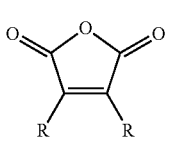 (II-5)

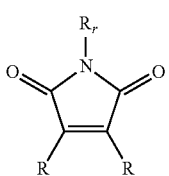 (II-6)

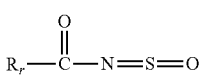 (II-7)

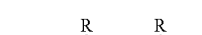

$$R_r-\overset{O}{\underset{}{C}}-N=S=O$$ (II-7)

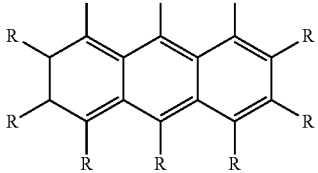 (II-8)

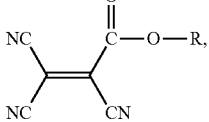 (II-9)

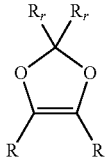 (II-10)

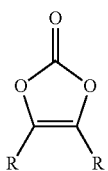 (II-11)

-continued

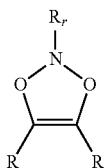
(II-12)

(wherein each of R and $R_r$ is independently selected from the group consisting of hydrogen, halogens, hydroxy group, amide groups, mercapto group, cyano group, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, substituted or unsubstituted aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms), wherein said substituted fused polycyclic aromatic compound of the formula (I-4) is substituted with a substituent each independently selected from the group consisting of halogens, alkyl groups having from 1 to 20 carbon atoms, alkenyl groups having from 2 to 20 carbon atoms, alkynyl groups having from 2 to 20 carbon atoms, substituted or unsubstituted aromatic groups having from 4 to 20 carbon atoms, ester groups having from 2 to 10 carbon atoms, ether groups having from 1 to 20 carbon atoms, ketone groups having from 1 to 20 carbon atoms, amino groups having from 1 to 20 carbon atoms, amide groups having from 1 to 20 carbon atoms, imide groups having from 1 to 20 carbon atoms, and sulfide groups having from 1 to 20 carbon atoms).

2. The adduct compound according to claim 1, wherein said double bond-containing compound (II) has the following formula (II-6):

(II-6)

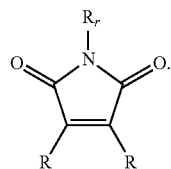

3. The adduct compound according to claim 1, wherein said double bond-containing compound (II) has the following formula (II-1):

(II-1)

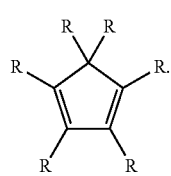

4. The adduct compound according to claim 1, wherein said double bond-containing compound (II) has the following formula (II-2):

(II-2)

5. The adduct compound according to claim 1, wherein said double bond-containing compound (II) has the following formula (II-3):

(II-3)

6. The adduct compound according to claim 1, wherein said double bond-containing compound (II) has the following formula (II-4):

(II-4)

7. The adduct compound according to claim 1, wherein said double bond-containing compound (II) has the following formula (II-5):

(II-5)

8. The adduct compound according to claim 1, wherein said double bond-containing compound (II) has the following formula (II-7):

(II-7)

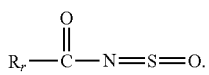

9. The adduct compound according to claim 1, wherein said double bond-containing compound (II) has the following formula (II-8):

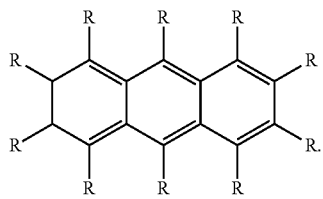

(II-8)

10. The adduct compound according to claim 1, wherein said double bond-containing compound (II) has the following formula (II-9):

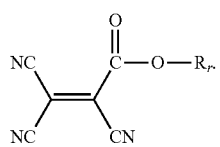

(II-9)

11. The adduct compound according to claim 1, wherein said double bond-containing compound (II) has the following formula (II-10):

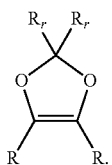

(II-10)

12. The adduct compound according to claim 1, wherein said double bond-containing compound (II) has the following formula (II-11):

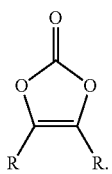

(II-11)

13. The adduct compound according to claim 1, wherein said double bond-containing compound (II) has the following formula (II-12):

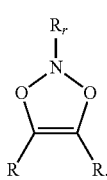

(II-12)

14. The adduct compound according to claim 1, which is a compound having the following formula (III-1) or a stereoisomer thereof:

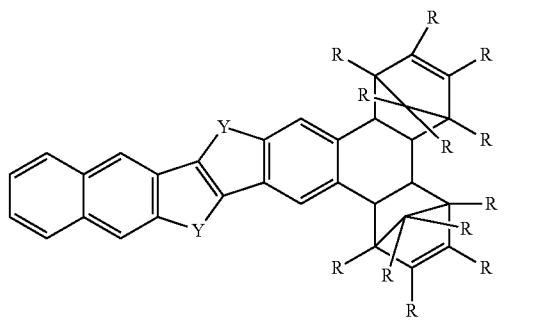

(III-1)

(wherein each Y is independently an element selected from the group consisting of chalcogens, each of R and $R_r$ is independently selected from the group consisting of hydrogen, halogens, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms, and the fused benzene ring moiety is substituted or unsubstituted).

15. The adduct compound according to claim 1, which is a compound having the following formula (III-6) or a stereoisomer thereof:

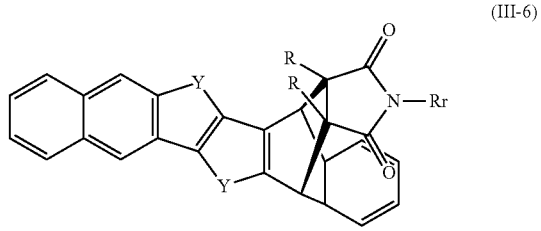

(III-6)

(wherein each Y is independently an element selected from the group consisting of chalcogens, each R is independently selected from the group consisting of hydrogen, halogens, alkyl groups having from 1 to 10 carbon atoms, alkenyl groups having from 2 to 10 carbon atoms, alkynyl groups having from 2 to 10 carbon atoms, alkoxy groups having from 1 to 10 carbon atoms, aromatic groups having from 4 to 10 carbon atoms, ester groups having from 1 to 10 carbon atoms, ether groups having from 1 to 10 carbon atoms, ketone groups having from 1 to 10 carbon atoms, amino groups having from 1 to 10 carbon atoms, amide groups having from 1 to 10 carbon atoms, imide groups having from 1 to 10 carbon atoms, and sulfide groups having from 1 to 10 carbon atoms, and the fused benzene ring moiety is substituted or unsubstituted).

16. The adduct compound according to claim 15, which is an Exo adduct.

17. An adduct compound-containing solution, comprising the adduct compound according to claim 1 dissolved in a solvent.

18. The solution according to claim 17, wherein the solution comprises the adduct compound according to claim 1 and at least one stereoisomer thereof dissolved in a solvent, and the proportion of a stereoisomer having a lowest thermal elimination temperature based on the total amount of said adduct compound and at least one stereoisomer thereof is more than 50 mol %.

19. The solution according to claim 18, wherein the solution comprises Exo and Endo forms of the adduct compound according to claim 1 dissolved in a solvent, and the proportion of a stereoisomer having a lower thermal elimination temperature based on the total amount of the Exo and Endo forms of said adduct compound is more than 50 mol %.

20. The solution according to claim 17, wherein the solution comprises Exo and Endo forms of the adduct compound according to claim 14 dissolved in a solvent, and the proportion of the Exo form based on the total amount of the Exo and Endo forms of said adduct compound is more than 50 mol %.

21. A method for producing an organic semiconductor film, comprising:
coating said adduct compound-containing solution according to claim 17 on a substrate to form a film, and
eliminating said double bond-containing compound (II) from said adduct compound and removing the double bond-containing compound (II) by depressurizing and/or heating said film to obtain an organic semiconductor film formed of said fused polycyclic aromatic compound of formula (I-4).

22. The method according to claim 21, wherein the elimination and removal of said double bond-containing compound (II) is performed by heating at a heating rate of more than 100° C./min.

23. The method according to claim 21, wherein said heating is performed by bringing said substrate having said film into direct contact with a heated material, introducing said substrate having said film into a heated region, and/or radiating an electromagnetic wave to the film side or the substrate side of said substrate having said film.

24. The method according to claim 22, wherein said organic semiconductor film has a crystal with a long axis diameter of more than 5 μm of said fused polycyclic aromatic compound of formula (I-4).

25. The method according to any one of claim 21, wherein said elimination and removal is performed under an air atmosphere.

26. A method for producing an organic semiconductor device, comprising producing an organic semiconductor film by the method according to claim 21.

27. An organic semiconductor device having an organic semiconductor film, wherein said organic semiconductor film is formed of said substituted or non-substituted fused polycyclic aromatic compound of formula (I-4), and said organic semiconductor film contains the adduct compound according to claim 1.

28. The organic semiconductor device according to claim 27, wherein the device is a thin-film transistor having a source electrode, a drain electrode, a gate electrode, a gate insulating film and said organic semiconductor film; and the thin-film transistor insulates said source electrode and said drain electrode from said gate electrode by said gate insulating film, and controls the current flowing through said organic semiconductor from said source electrode to said drain electrode by the voltage applied to said gate electrode.

29. A method for synthesizing the adduct compound according to claim 1, comprising mixing said fused polycyclic aromatic compound of formula (I-4) with said double bond-containing compound (II).

30. A method for synthesizing the adduct compound according to claim 1, comprising the following steps (a) to (c):
(a) providing an adduct compound, the adduct compound having a structure wherein a double bond-containing compound (II) is added to a compound of the following formula (P) through said double bond:

$$Ar_1Q \qquad (I')$$

{wherein $Ar_1$ is a substituted or unsubstituted fused aromatic ring moieties of the following formula (b4):

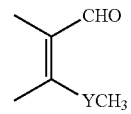

(b4)

and
Q has the following formula and constitutes a part of the fused aromatic ring of $Ar_1$:

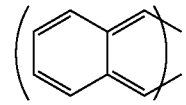

(wherein Y is an element selected from the group consisting of chalcogens), and
said substituted fused aromatic ring moieties (b4) is substituted with a substituent each independently selected from the group consisting of halogens, alkyl groups having from 1 to 20 carbon atoms, alkenyl groups having from 2 to 20 carbon atoms, alkynyl groups having from 2 to 20 carbon atoms, substituted or unsubstituted aromatic groups having from 4 to 20 carbon atoms, ester groups having from 2 to 10 carbon atoms, ether groups having from 1 to 20 carbon atoms, ketone groups having from 1 to 20 carbon atoms, amino groups having from 1 to 20 carbon atoms, amide groups having from 1 to 20 carbon atoms, imide groups having from 1 to 20 carbon atoms, and sulfide groups having from 1 to 20 carbon atoms);
(b) reacting two molecules of the adduct compound to obtain a compound of the following formula:

$$Ar_1Q=QAr_1 \qquad \text{Formula:}$$

(wherein Q=Q represents the following structure:

[Chem. 11]

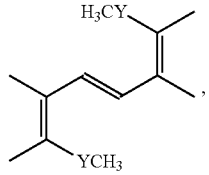

and
(b) reacting the obtained compound of said formula $Ar_1Q=QAr_1$ with iodine.

* * * * *